United States Patent
Kalamkar et al.

(10) Patent No.: US 10,565,849 B2
(45) Date of Patent: Feb. 18, 2020

(54) DETERMINING USE OF MEDICATION THROUGH RADIO FREQUENCY PASSIVE MODULATION

(71) Applicant: Kali Care, Inc., Mountain View, CA (US)

(72) Inventors: Abhijit Kalamkar, Sunnyvale, CA (US); Sina Fateh, Sunnyvale, CA (US)

(73) Assignee: KALI CARE, INC., Santa Clara, CA (US)

( * ) Notice: Subject to any disclaimer, the term of this patent is extended or adjusted under 35 U.S.C. 154(b) by 0 days.

(21) Appl. No.: 16/025,919

(22) Filed: Jul. 2, 2018

(65) Prior Publication Data

US 2020/0005620 A1   Jan. 2, 2020

(51) Int. Cl.
| | | |
|---|---|---|
| G08B 1/08 | (2006.01) | |
| G08B 21/18 | (2006.01) | |
| G16H 40/67 | (2018.01) | |
| G16H 20/13 | (2018.01) | |

(52) U.S. Cl.
CPC ............. *G08B 21/18* (2013.01); *G16H 20/13* (2018.01); *G16H 40/67* (2018.01)

(58) Field of Classification Search
CPC ......... G08B 21/18; G16H 40/67; G16H 20/13
USPC .................................................... 340/539.14
See application file for complete search history.

(56) References Cited

U.S. PATENT DOCUMENTS

| | | | | |
|---|---|---|---|---|
| 6,150,921 A * | 11/2000 | Werb | ...................... | G01S 13/84 340/10.1 |
| 6,353,406 B1 * | 3/2002 | Lanzl | ...................... | G01S 13/84 340/10.1 |
| 8,013,744 B2 * | 9/2011 | Tsai | .................... | G06K 19/0717 235/439 |
| 8,525,677 B2 * | 9/2013 | Scharfeld | ......... | G06K 19/07749 340/572.8 |
| 9,471,817 B1 * | 10/2016 | Alhazme | .......... | G06K 19/07345 |
| 9,495,851 B1 * | 11/2016 | Russell | .................. | G06Q 10/00 |
| 2004/0008123 A1 * | 1/2004 | Carrender | ......... | G06K 19/07749 340/8.1 |
| 2006/0273902 A1 * | 12/2006 | Shafer | ................ | G08B 13/2417 340/572.1 |
| 2007/0096906 A1 * | 5/2007 | Lyons | ................ | G06K 19/0717 340/572.1 |
| 2007/0210173 A1 * | 9/2007 | Nagel | ................ | G06K 19/0739 235/492 |

(Continued)

*Primary Examiner* — Zhen Y Wu
(74) *Attorney, Agent, or Firm* — Perkins Coie LLP

(57) ABSTRACT

An RF signal is provided by a base such as a smart phone. A remote is engaged with a medication container. The remote includes an RFPM, RF signal receiver, LO signal generator, and IF signal emitter. An energizer on the remote provides power only as medication is dispensed. While energized, the RFPM modulates the RF signal with an LO signal to produce an IF signal. The existence of the IF signal (characteristic of the RFPM, RF signal, and LO signal) thus indicates medication has been dispensed. The IF signal is detected in the base, and registered (recorded, displayed, communicated, etc.) as an indication that medication has been dispensed. The remote may be configured as a label applied to or a sleeve engaged with an otherwise "non-smart" container. This provides authenticated data regarding medication adherence, transparent to the user and requiring no additional user actions to register the data.

30 Claims, 23 Drawing Sheets

(56) References Cited

U.S. PATENT DOCUMENTS

| | | | | |
|---|---|---|---|---|
| 2008/0001737 | A1* | 1/2008 | Metry | B32B 7/02 |
| | | | | 340/540 |
| 2008/0061153 | A1* | 3/2008 | Hickle | A61M 16/183 |
| | | | | 235/492 |
| 2010/0188211 | A1* | 7/2010 | Brommer | G06K 19/0675 |
| | | | | 340/539.32 |
| 2012/0008714 | A1* | 1/2012 | Rizwan | A61B 5/0031 |
| | | | | 375/295 |
| 2012/0025981 | A1* | 2/2012 | Marcovici | B65D 83/04 |
| | | | | 340/540 |
| 2012/0154120 | A1* | 6/2012 | Alloro | G06F 19/3462 |
| | | | | 340/10.1 |
| 2013/0044007 | A1* | 2/2013 | Paavilainen | G09F 3/0292 |
| | | | | 340/945 |
| 2016/0001936 | A1* | 1/2016 | Rap | B65D 43/16 |
| | | | | 222/490 |
| 2017/0046501 | A1* | 2/2017 | Coleman | A61J 1/035 |
| 2017/0163357 | A1* | 6/2017 | Cordier | G06K 7/0095 |
| 2017/0300659 | A1* | 10/2017 | Ziv | G06F 19/326 |
| 2018/0308571 | A1* | 10/2018 | Tupler | A61J 7/00 |
| 2018/0330315 | A1* | 11/2018 | Gurumohan | H04W 76/14 |
| 2018/0373904 | A1* | 12/2018 | Malarky | G06K 7/0008 |

* cited by examiner

DETERMINING USE OF MEDICATION THROUGH RADIO FREQUENCY PASSIVE MODULATION

FIELD OF THE INVENTION

Various embodiments concern acquisition of information indicating the use of medication. More particularly, various embodiments relate to providing a positive indication that medication is being taken, dispensed, prepared for use, etc., in a manner that does not require directed signaling action on the part of the user, by utilizing a radio frequency passive modulator (RFPM) in/on the medication container but without necessarily requiring smart functionality and/or a power source in/on the medication container.

BACKGROUND

A substantial portion of medications are not taken as prescribed. By some estimates, in clinical practice up to 50% or more of medications either may not be taken at all or may be taken with significant deviations from what is prescribed for the patient. For example, doses of a medication may be skipped, the medication may not be taken at the right intervals, at the right times, in the right dose, applied in the correct manner, etc. Such deviation from a prescribed medication regimen may be referred to broadly as "nonadherence". Nonadherence to prescribed medication regimens may have dramatic negative effects on health and/or healthcare costs, whether considering individuals or societies collectively.

Nonadherence may be even more common in clinical research, wherein some estimates indicate nonadherence of up to 70% or more. Nonadherence in a research context also presents other potential concerns. For example, testing of new medications typically may include efforts to determine the effectiveness of the medication, what side effects occur, how severe those side effects may be, in what fraction of the population those side effects occur, etc. Thus nonadherence in a research setting may distort the basic understanding of a medication, e.g., if a medication is in fact highly effective if taken as prescribed but ineffective or dangerous if not taken properly, poor adherence within a clinical trial may result in data showing that the medication is not effective (when the actual problem is that it was not taken correctly).

One matter complicating issues related to nonadherence is that reliable data on the existence, degree, and form(s) of nonadherence present may be difficult to acquire. Whether for an individual, a larger population, or even a carefully selected and/or monitored group such as the subjects in a clinical trial, authentic data on how much nonadherence is taking place, among whom, and in what forms (e.g., missing doses, taking the medication incorrectly, etc.) may not be available through conventional sources. Without such authenticated data it may not even be known how much nonadherence is taking place (beyond estimates), much less what the specific impacts of nonadherence may be in a given case.

At least in principle, it may be possible to detect, record, and/or report the use of a medication through making medication containers "smart". However, such an approach also presents challenges. For example, medication containers that are handled and/or carried regularly may be subject to various environmental hazards, e.g., the container may get wet, be dropped, be sat upon (for example if kept in a pocket), be exposed to extreme temperatures (for example if left in a car on a hot day or kept in an outer coat pocket in very cold weather), be bumped or compressed by other objects in a pocket or bag, etc. In addition to potential issues of fragility, sensors, processors, a data stores, communicators, power sources, etc., as may be adequate to provide smart functionality may add significant cost, weight, bulk, etc. to a container.

In addition, even if a medication container is smart in itself, it may be useful to communicate data acquired thereby to some other entity. This typically may require either a physical connection, or a wireless connection. Neither is without concerns. A requirement to regularly make a physical connection to download data may simply "kick the can down the road", in that if a patient cannot be relied upon to take a medication regularly then that patient also may not download data regularly, either. On the other hand wireless communication may require additional power, additional components for wireless communication, etc., and may present challenges regarding reliability, interference with/from other electronic devices, etc.

It is also noted that medication containers may be designed only to be used for limited periods, e.g., for 30 days until empty, for a single application of medication, after which the containers—and smart components thereon—may be discarded. Thus it may be particularly useful if components in or on the container (whether for smart functionality or otherwise) are simple, robust, inexpensive, easily recycled, etc.

BRIEF SUMMARY OF THE INVENTION

This disclosure contemplates a variety of systems, apparatus, methods, and paradigms for determining use of medication through radio frequency passive modulation.

In one embodiment an apparatus is provided, including a remote physically engaged with an eye drop medication squeeze container, and a base distal from the container. The remote includes a membrane adhered to the container, a radio frequency passive modulator disposed in the membrane and adapted to apply a frequency modification to an RF signal by frequency mixing an LO signal therewith so as to produce an IF signal characteristic of the radio frequency passive modulator, the RF signal, and the LO signal, an RF receiver disposed in the membrane and adapted to wirelessly receive the RF signal and provide the RF signal to an RF port of the radio frequency passive modulator, an LO generator disposed in the membrane and adapted to generate an LO signal and provide the LO signal to an LO port of the radio frequency passive modulator, an IF emitter disposed in the membrane and adapted to receive the IF signal from an IF port of the radio frequency passive modulator and wirelessly emit the IF signal, a flexible region defined in the membrane and adapted to be deformed by a user squeezing the medication container so as to dispense an eye drop medication therefrom, and a piezoelectric element engaged with the flexible region and in communication with the radio frequency passive modulator, the RF receiver, the LO generator, and the IF emitter such that when the flexible region is deformed the piezoelectric element deforms therewith and energizes the radio frequency passive modulator, the RF receiver, the LO generator, and the IF emitter. The base includes a processor adapted to execute executable instructions, an RF receiver adapted to wirelessly receive the RF signal and communicate the RF signal to the processor, an IF receiver adapted to wirelessly receive the IF signal and communicate the IF signal to the processor, a data store in communication with the processor, a wireless communicator in communication with the processor, a graphical display in communication with the processor, a clock in communication with the processor, and a base electrical supply adapted to energize the processor, the RF receiver, the IF receiver, the data store, the communicator, the display, and the clock. The processor is adapted to compare the IF signal to an IF signal standard instantiated thereon. The processor is also adapted to register a dispersal of the eye drop medication if the IF signal satisfies the IF standard, registering the dispersal including storing the dispersal and a dispersal time in the data store, wirelessly communicating the dispersal and the dispersal time to an external entity via the wireless communicator, and outputting the dispersal and the dispersal time via the graphical display.

In another embodiment an apparatus is provided, including a remote engaged with a container, and a base distal from the container. The remote includes a radio frequency passive modulator adapted to apply a frequency modification to an RF signal by frequency mixing an LO signal therewith so as to produce an IF signal characteristic of radio frequency passive modulator, the RF signal, and the LO signal, an RF receiver adapted to wirelessly receive the RF signal and provide the RF signal to an RF port of the radio frequency passive modulator, an LO generator adapted to generate an LO signal and provide the LO signal to an LO port of the radio frequency passive modulator, an IF emitter adapted to receive the IF signal from an IF port of the radio frequency passive modulator and wirelessly emit the IF signal, an initiator adapted to be initiated by an action associated with dispensing a contents from the container, and an energizer engaged with the initiator and in communication with the radio frequency passive modulator, the RF receiver, the LO generator, and the IF emitter such that when the initiator is initiated the energizer energizes the radio frequency passive modulator, the RF receiver, the LO generator, and the IF emitter. The base includes a processor adapted to execute executable instructions, and an RF assembly. The RF assembly may include an RF generator adapted to generate the RF signal therein and an RF emitter adapted to receive the RF signal from the RF generator and wirelessly emit the RF signal, and/or an RF receiver adapted to wirelessly receive the RF signal. The base also includes an IF receiver adapted to wirelessly receive the IF signal and provide the IF signal to the processor, and a registerer. The registerer may be a data store, a communicator, and/or an outputter. The base also includes a clock in communication with the processor, and a base electrical supply adapted to energize the processor, the RF assembly, the IF receiver, the registerer, and the clock. The processor is adapted to compare the IF signal to an IF signal standard, and to register via the registerer a contextual event associated with dispensing the contents if the IF signal satisfies the IF standard. Registering includes storing a presence of the contextual event and a time of the contextual event in the data store, communicating the presence of the contextual event and the time of the contextual event to an external entity via the communicator, and/or outputting the presence of the contextual event and the time of the contextual event via the outputter.

The base may include the RF generator and the RF emitter, wherein the IF signal standard is characteristic of the RF signal as generated and emitted in the base, the LO signal as generated in the remote, and the frequency mixing in the radio frequency passive modulator. The base may include the RF receiver, wherein the IF signal standard is characteristic of the RF signal as generated externally from the base and the remote, the LO signal as generated in the remote, and the frequency mixing in the radio frequency passive modulator.

The RF signal may be an ambient signal. The RF signal may be an electromagnetic wave, including mains electricity, transmission electricity, data line emissions, fluorescent lighting, broadcast radio, broadcast television, cellular communication, Wi-Fi®, BLUETOOTH®, and astronomical radio waves.

The IF signal standard may include the RF signal, the LO signal, and at least one frequency mixing parameter for the radio frequency passive modulator. The IF signal standard may be instantiated on the processor, stored in the data store, and/or obtained via the communicator. The IF signal standard may address multiple IF signals characteristic with multiple respective RF signals.

The base data store may be a hard drive, a solid state drive, an optical drive, a removable memory card, a removable optical disc, and/or a removable magnetic disc. The base communicator may include a hard-wired communicator, a Wi-Fi® communicator, BLUETOOTH® communicator, a cellular network communicator, an infrared communicator, and/or a radio communicator. The base outputter may include a graphical display, an audio speaker, visual telltales, an LCD display, an LED display, a CRT display, and/or an electronic paper display.

The base may include a user interface. The user interface may include a keypad, a touch screen, a voice input, and/or at least one discrete mechanical control.

The base may be a portable electronic device. The base may be a smart phone, a tablet computer, a laptop computer, a desktop computer, a game console, a smart watch, a PDA, and/or a head mounted display.

The container may be a medication container, and the contents may include a medication. The container may be a squeeze bottle, a squeeze tube, a hypodermic syringe, an auto-injector, a syrette, a twist-cap bottle, a flip-top bottle, an inhaler, and/or a single-use cartridge.

The initiator may include a flexible region defined adapted to be deformed by a user squeezing the container so as to dispense the contents therefrom, a rotary cap for the container adapted to be rotated by the user so as to open the container, a movable cap for the container adapted to be translated by the user so as to open the container, a frangible element adapted to be broken by the user so as to open the container, an optical window adapted to pass light therethrough, and/or an RF window adapted to pass radio frequency waves therethrough.

The energizer may include a piezoelectric element, a plunger generator, a rotary generator, a photovoltaic element, a radio frequency power harvester, a triboelectric element, and/or a fractoelectric element.

The remote may include a control gate with a negative state and a positive state. If the control gate is in the negative state the control gate inhibits the energizer from energizing at least one of the radio frequency passive modulator, the RF receiver, the LO generator, and the IF emitter. If the control gate is in the positive state the control gate does not inhibit the energizer.

The control gate may include a cap sensor for a cap for the container, such that if the cap is engaged with the container the control gate is in a negative state, and if the cap is not engaged with the container the control gate is in a positive state. The control gate may include a short circuit within the cap, such that if the cap is engaged with the container the short circuit bypasses the energizer from energizing the at least one of the radio frequency passive modulator, the RF receiver, the LO generator, and the IF emitter, and if the cap is not engaged with the container the short circuit does not bypass the energizer.

The remote may be integral to the container.

The initiator may include a flexible region defined in a wall of the container. The energizer may include a piezoelectric element engaged with a flexible region of the container. The radio frequency passive modulator, the RF receiver, the LO generator, and the IF emitter are disposed in a wall of the container.

The remote may be fixedly engaged with the container.

The remote may include a membrane fixedly adhered to the container. The initiator may include a flexible region defined in the membrane. The energizer may include a piezoelectric element engaged with the flexible region. The radio frequency passive modulator, the RF receiver, the LO generator, and the IF emitter may be disposed in the membrane.

The remote may be adapted to be removably engaged with the container.

The remote may include a sleeve with the container removably disposed therein. The initiator may include a flexible region defined in the sleeve. The energizer may include a piezoelectric element engaged with the flexible region. The radio frequency passive modulator, the RF receiver, the LO generator, and the IF emitter may be disposed in the sleeve.

In another embodiment an apparatus is provided, including a remote adapted to be engaged with a container. The remote includes a radio frequency passive modulator adapted to apply a frequency modification to an RF signal by frequency mixing an LO signal therewith so as to produce an IF signal characteristic of the radio frequency passive modulator, the RF signal, and the LO signal, an RF receiver adapted to wirelessly receive the RF signal and provide the RF signal to an RF port of the radio frequency passive modulator, an LO generator adapted to generate an LO signal and provide the LO signal to an LO port of the radio frequency passive modulator, an IF emitter adapted to receive the IF signal from an IF port of the radio frequency passive modulator and wirelessly emit the IF signal, an initiator adapted to be initiated by an action associated with dispensing a contents from the container, and an energizer engaged with the initiator and in communication with the radio frequency passive modulator, the RF receiver, the LO generator, and the IF emitter such that when the initiator is initiated the energizer energizes the radio frequency passive modulator, the RF receiver, the LO generator, and the IF emitter.

In another embodiment an apparatus is provided, including a base. The base includes a processor adapted to execute executable instructions and an RF assembly. The RF assembly includes at least one of an RF generator adapted to generate an RF signal for a radio frequency passive modulator therein and an RF emitter adapted to receive the RF signal from the RF generator and wirelessly emit the RF signal, and an RF receiver adapted to wirelessly receive the RF signal. The base includes an IF receiver adapted to wirelessly receive an IF signal from the radio frequency passive modulator characteristic of the radio frequency passive modulator, the RF signal, and the LO signal and to provide the IF signal to the processor, and a registerer. The registerer includes a data store, a communicator, and/or an outputter. The base also includes a clock and a base electrical supply adapted to energize the processor, the RF assembly, the IF receiver, the registerer, and the clock. The processor is adapted to compare the IF signal to an IF signal standard, and to register via the registerer an event associated with the radio frequency passive modulator if the IF signal satisfies the IF standard. Registering includes storing a presence of the contextual event and a time of the contextual event in the data store, communicating the presence of the contextual event and the time of the contextual event to an external entity via the communicator, and/or outputting the presence of the contextual event and the time of the contextual event via the outputter.

In another embodiment a method is provided, including engaging a remote with a container, and establishing a base distal from the container. The remote includes a radio frequency passive modulator adapted to apply a frequency modification to an RF signal by frequency mixing an LO signal therewith so as to produce an IF signal characteristic of the radio frequency passive modulator, the RF signal, and the LO signal. The remote also includes an RF receiver adapted to wirelessly receive the RF signal and provide the RF signal to an RF port of the radio frequency passive modulator, an LO generator adapted to generate an LO signal and provide the LO signal to an LO port of the radio frequency passive modulator, and an IF emitter adapted to receive the IF signal from an IF port of the radio frequency passive modulator and wirelessly emit the IF signal. The remote further includes an initiator adapted to be initiated by an action associated with dispensing a contents from the container, and an energizer engaged with the initiator and in communication with the radio frequency passive modulator, the RF receiver, the LO generator, and the IF emitter such that when the initiator is initiated the energizer energizes the radio frequency passive modulator, the RF receiver, the LO generator, and the IF emitter. The base includes a processor adapted to execute executable instructions, and an RF assembly. The RF assembly includes an RF generator adapted to generate the RF signal therein and an RF emitter adapted to receive the RF signal from the RF generator and wirelessly emit the RF signal, and/or an RF receiver adapted to wirelessly receive the RF signal. The base also includes an IF receiver adapted to wirelessly receive the IF signal and provide the IF signal to the processor, and a registerer. The registerer includes a data store, a communicator, and/or an outputter. The base also includes a clock in communication with the processor, and a base electrical supply adapted to energize the processor, the RF assembly, the IF receiver, the registerer, and the clock. The processor is adapted to compare the IF signal to an IF signal standard, and to register via the registerer a contextual event associated with dispensing the contents if the IF signal satisfies the IF standard. Registering includes storing a presence of the contextual event and a time of the contextual event in the data store, communicating the presence of the contextual event and the time of the contextual event to an external entity via the communicator, and/or outputting the presence of the contextual event and the time of the contextual event via the outputter.

The base may include a portable electronic device, with the processor, the RF assembly, the IF receiver, the registerer, the clock, and the base electrical supply disposed within the portable electronic device. Establishing the base may include instantiating executable instructions onto the processor adapted to compare the IF signal to the IF signal standard, determine whether the IF signal satisfies the IF signal standard, and register the contextual event if the IF signal satisfies the standard.

In another embodiment a method is provided, including initiating an initiator of a remote engaged with a container through an action associated with dispensing a contents from the container. The initiator is engaged with an energizer of the remote, the energizer being in communication with a radio frequency passive modulator, an RF receiver, an LO generator, and an IF emitter of the remote such that when the initiator is initiated the energizer energizes the radio frequency passive modulator, the RF receiver, the LO generator, and the IF emitter. The radio frequency passive modulator is adapted to apply a frequency modification to an RF signal by frequency mixing an LO signal therewith so as to produce an IF signal characteristic of the radio frequency passive modulator, the RF signal, and the LO signal. The RF receiver being adapted to wirelessly receive the RF signal and provide the RF signal to an RF port of the radio frequency passive modulator. The LO generator is adapted to generate an LO signal and provide the LO signal to an LO port of the radio frequency passive modulator. The IF emitter is adapted to receive the IF signal from an IF port of the radio frequency passive modulator and wirelessly emit the IF signal. Such that, when the initiator is initiated the characteristic IF signal is produced by the radio frequency passive modulator and emitted by the IF emitter.

The method may include establishing a base distal from the container. The base may include a processor adapted to execute executable instructions and an RF assembly. The RF assembly may include an RF generator adapted to generate the RF signal therein and an RF emitter adapted to receive the RF signal from the RF generator and wirelessly emit the RF signal, and/or an RF receiver adapted to wirelessly receive the RF signal. The base may include an IF receiver adapted to wirelessly receive the IF signal and provide the IF signal to the processor, and a registerer. The registerer may include a data store, a communicator, and/or an outputter. The base may include a clock in communication with the processor, and a base electrical supply adapted to energize the processor, the RF assembly, the IF receiver, the registerer, and the clock. The processor may be adapted to compare the IF signal to an IF signal standard, and to register via the registerer a contextual event associated with dispensing the contents if the IF signal satisfies the IF standard. Registering may include storing a presence of the contextual event and a time of the contextual event in the data store, communicating the presence of the contextual event and the time of the contextual event to an external entity via the communicator, and outputting the presence of the contextual event and the time of the contextual event via the outputter.

In another embodiment a method is provided, including establishing an RF signal n a base distal from a container, establishing the RF signal including generating the RF signal in an RF signal generator and wirelessly emitting the RF signal from an RF signal emitter, and/or wirelessly receiving the RF signal in an RF signal receiver. In a remote engaged with the container, initiating an initiator responsive to an action associated with dispensing a contents from a container, such that initiating the initiator causes an energizer of the remote to energize a radio frequency passive modulator, an RF receiver, an LO generator, and an IF emitter in the remote. The method includes, when energized, wirelessly receiving the RF signal in the RF receiver, communicating the RF signal to the radio frequency passive modulator, generating an LO signal in the LO generator, modulating the RF signal and the LO signal in the radio frequency passive modulator to produce an IF signal, communicating the IF signal to the IF emitter, and wirelessly emitting the IF signal from the IF emitter. The method includes, in the base, receiving the IF signal in an IF receiver, comparing the IF signal to an IF signal standard, and if the IF signal satisfies the IF signal standard registering an event associated with the contents of the container. Registering includes at least one of storing the event and an event time thereof in a data store, communicating the event and the event time via a communicator, and outputting the event and the event time from an outputter.

In another embodiment a method is provided, including establishing an RF signal in a base distal from a container. Establishing the RF signal includes generating the RF signal and wirelessly emitting the RF signal from the base, and/or wirelessly receiving the RF signal in the base. The method includes, in a remote engaged with the container, initiating an initiator responsive to an action associated with dispensing a contents from a container, such that initiating the initiator causes an energizer of the remote to energize the remote. The method includes, while the remote is energized, wirelessly receiving the RF signal in the remote, generating an LO signal in the remote, modulating the RF signal and the LO signal in the remote, and wirelessly emitting the IF signal from remote. The method also includes, in the base, receiving the IF signal, comparing the IF signal to an IF signal standard, and if the IF signal satisfies the IF signal standard registering an event associated with the contents of the container. Registering includes at least one of storing the event and an event time thereof in the base, communicating the event and the event time from the base, and outputting the event and the event time from the base.

In another embodiment an apparatus is provided, including RF modifying means for applying a frequency modification to an RF signal by frequency mixing an LO signal therewith so as to produce an IF signal, first RF receiving means for wirelessly receiving the RF signal, LO generating means for generating the LO signal, and IF emitting means for wirelessly emitting the IF signal. The apparatus also includes energizing means for energizing the RF modifying means, the RF receiving means, the LO generating means, and the IF emitting means, initiating means for initiating the energizing means responsive to an action associated with dispensing a contents from a container, and engaging means for engaging the RF modifying means, the RF receiving means, the LO generating means, the IF emitting means, the energizing means, and the initiating means with the container. RF provision means include RF generating means for generating the RF signal and RF emitting means for wirelessly emitting the RF signal, and/or second RF receiving means for wirelessly receiving the RF signal. The apparatus includes IF receiving means for wirelessly receiving the IF signal, comparing means for comparing the IF signal to an IF standard, and certifying means for certifying the IF signal as corresponding with an event associated with the contents of the container if the IF signal satisfies the IF standard. The apparatus further includes timing means for determining an event time of the event, and registering means for registering the event. The registering means include storing means for storing the event and the event time, communicating means for communicating the event and the event time, and/or outputting means for outputting the event and the event time. The RF provision means, the IF receiving means, the comparing means, the certifying means, the timing means, and the registering means are distal from the container.

BRIEF DESCRIPTION OF THE SEVERAL VIEWS OF THE DRAWINGS

Various objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

Figure 1A:
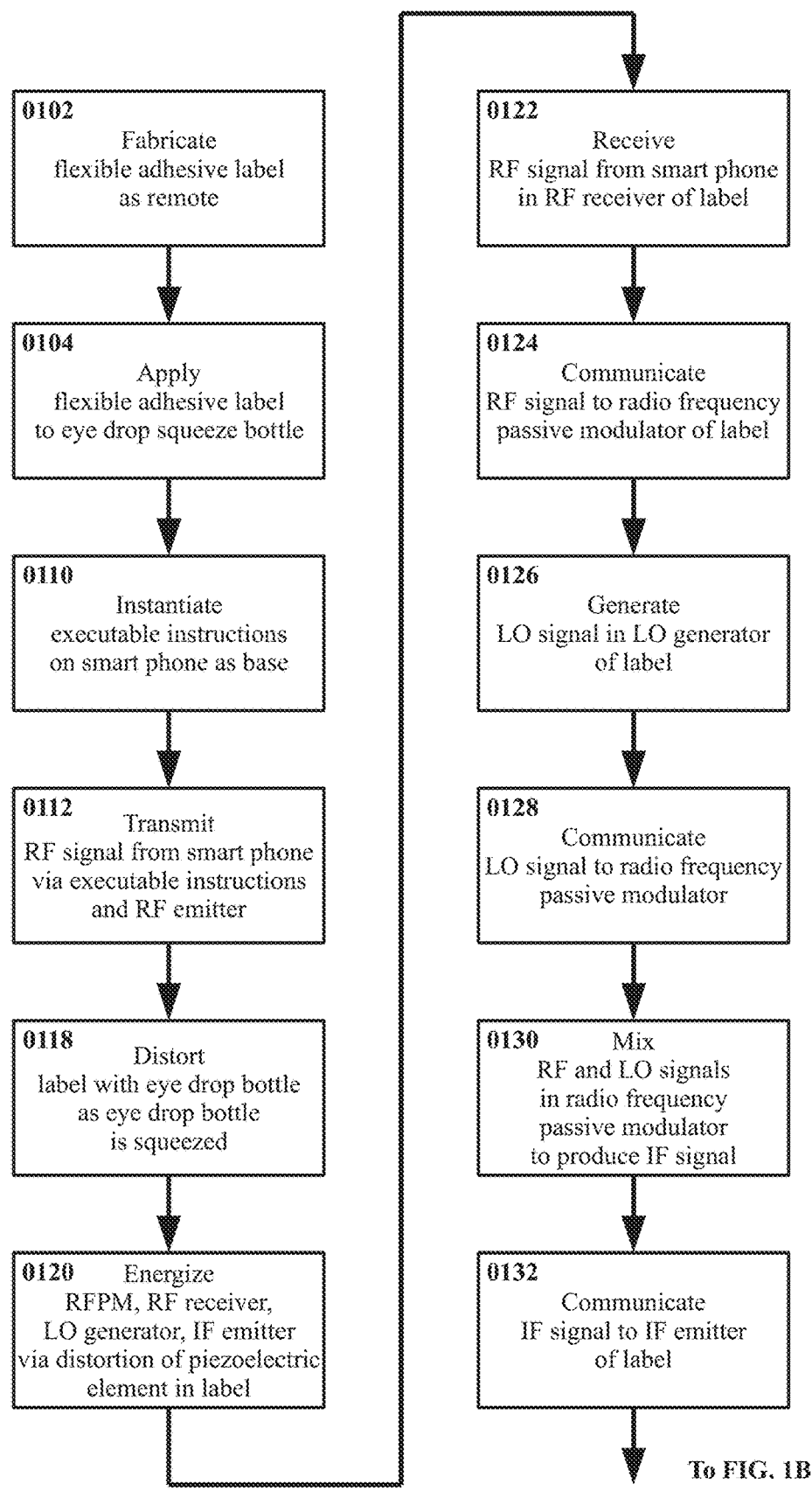
FIG. 1A and FIG. 1B depict an example method for determining the use of medication through radio frequency passive modulation, in flow chart form.

The figures depict various embodiments described throughout the Detailed Description for the purposes of illustration only. While specific embodiments have been shown by way of example in the drawings and are described in detail below, the technology is amenable to various modifications and alternative forms. The intention is not to limit the technology to the particular embodiments described. Accordingly, the claimed subject matter is intended to cover all modifications, equivalents, and alternatives falling within the scope of the technology as defined by the appended claims.

DETAILED DESCRIPTION OF THE INVENTION

Various embodiments are described herein that relate to determining use of medication through radio frequency passive modulation.

Figure 1B:
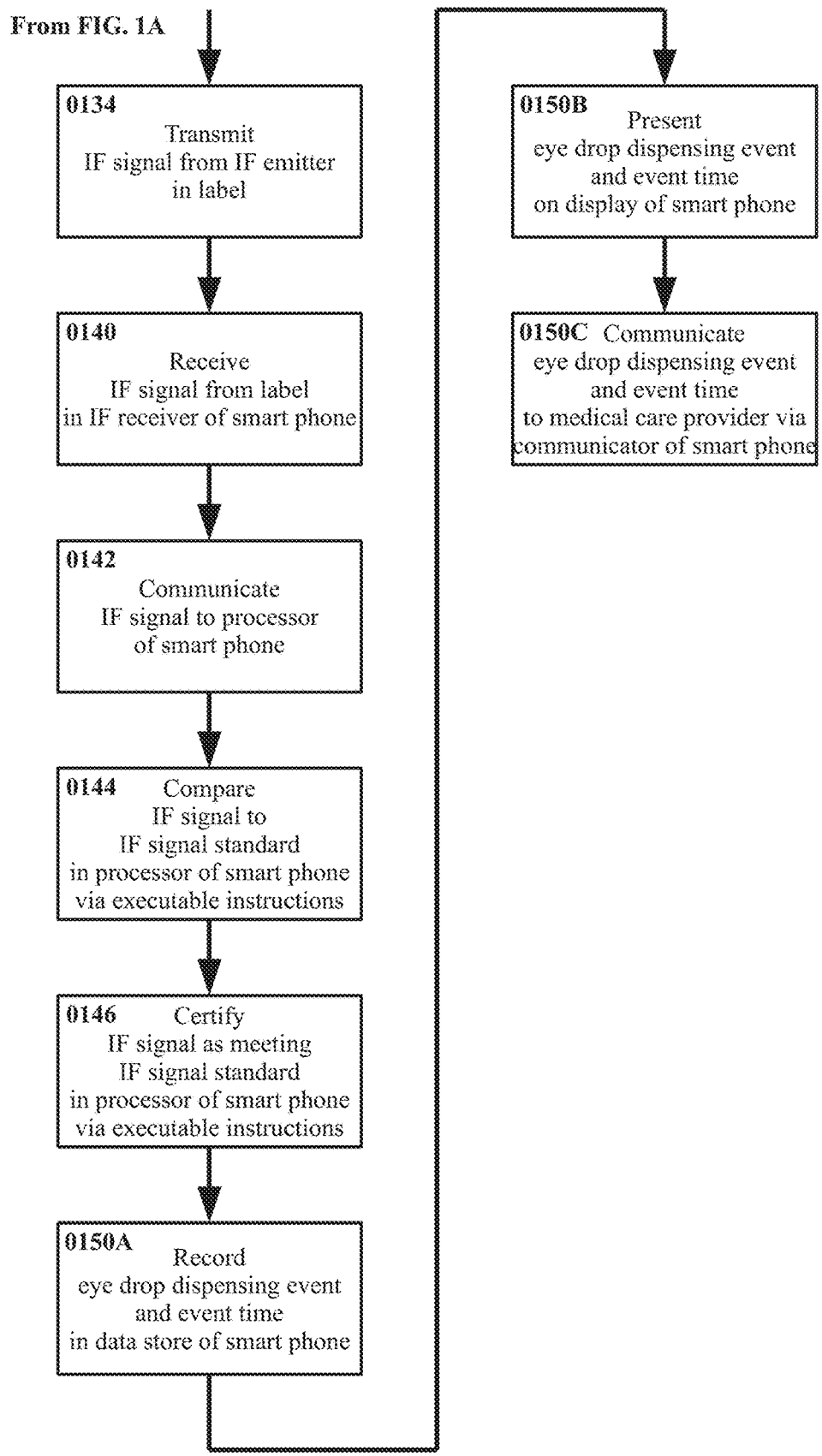

With reference now to FIG. 1A and FIG. 1B, an example method for determining the use of medication through radio frequency passive modulation is presented in flow chart form. For purposes of explanation, the arrangement in FIG.

1A and FIG. 1B (and in certain other examples herein) refers specifically to a remote in the form of an adhesive label as applied to an eye drop medication squeeze drop bottle, and to a base in the form of a smart phone with executable instructions instantiated thereon. However, these are examples only, and are not limiting; other configurations may be equally suitable.

As an initial colloquial (and non-limiting) summary, in FIG. 1A and FIG. 1B a smart phone broadcasts an RF signal. Dispensing medication from the bottle activates electronic components on the label of the bottle that mix the RF signal with an LO signal, producing an IF signal that is broadcast by the label. That IF signal is then detected by the smart phone, and is logged as an indication that the medication has been dispensed.

More particularly in FIG. 1A, an adhesive label is fabricated 0102 for use as a remote. The remote includes a radio frequency passive modulator ("RFMP"), an RF signal receiver, an LO signal generator, an IF signal emitter, and a piezoelectric element. It is noted that "RF", "LO", and "IF" are terms referring to signals as may be associated with an RFMP. Typically, though not necessarily, RF may refer to "Radio Frequency" (or, though not an acronym, "Signal Input"), LO to "Local Oscillator", and IF to "Intermediate Frequency".

At least some portion of the adhesive label is flexible. Typically, though not necessarily, the RFPM, RF receiver, LO generator, IF emitter, and piezoelectric element maybe be incorporated into the label, such as being laminated or printed onto a base sheet, cast within a base sheet, etc. However, other arrangements, including but not limited to disposition on a surface of the label also may be suitable. More regarding components of the remote will be presented upon referencing the function thereof, subsequently herein.

The adhesive label is applied 0104 to an eye drop squeeze bottle suitable for dispensing an eye medication as droplets. Thus, the label—serving as a remote—is engaged with the medication container.

Moving on in FIG. 1A, executable instructions are instantiated 0110 onto a processor of a smart phone, the smart phone serving as a base. Typically, though not necessarily, the executable instructions may be instantiated as an "app" that is downloaded or otherwise installed onto the processor of the smart phone. The smart phone is presumed for purposes of explanation to include a communicator adapted to send and receive radio frequency signals (thus functioning as an RF emitter and an IF receiver), the aforementioned processor, a data store adapted to record information therein, and a display adapted to present graphical content. More regarding functionality of the executable instructions, and of elements of the smart phone serving functions with regard to the example method of FIG. 1A, will be presented subsequently herein.

In operation, the smart phone transmits 0112 an RF signal from the RF emitter, via execution of instructions instantiated onto the processor (e.g., previously in step 0110). The RF signal may be a characteristic signal, e.g., one of known wavelength, wave form, etc. Typically, though not necessarily, the RF signal may not be directed at any specific device, but rather may be a blanket broadcast covering an area. Thus, it may not be necessarily to establish communication protocols with any particular target for the RF signal, or even to identify whether a suitable target exists within the broadcast area.

Continuing in FIG. 1A, the eye drop bottle is distorted, e.g., squeezed by a person dispensing medication. The label is distorted 0118 with the bottle, at least in the flexible region of the label. Similarly, the piezoelectric element is stressed and/or distorted with the label, causing the piezoelectric element to produce an electrical output that energizes 0120 the RFPM, RF receiver, LO generator, and IF emitter of the label. That is, electrical power is supplied to the RFPM, RF receiver, LO generator, and IF emitter sufficient for operation thereof, in response to the piezo element being stressed/distorted (in response to the flexible portion of the label being distorted, and in turn in response to the bottle being squeezed).

With the RF receiver now in operation, the RF receiver on the label receives 0122 the RF signal as produced by the RF emitter of the smart phone. The RF signal is communicated 0124 to the RFPM, e.g., to an RF port therefor. Similarly, with the LO generator in operation, the LO receiver on the label generates 0126 an LO signal. The LO signal is communicated 0128 to the RFPM, e.g., to an LO port therefor. With the RFPM in operation, the RFPM modulates or "mixes" the RF signal with the LO signal, producing an IF signal therefrom (e.g., at an IF port). In practice, the IF signal may include two (or more) individual waveforms, e.g., RF+LO and RF−LO; however, for simplicity the IF signal is referred to in singular herein, unless otherwise noted. (Likewise, the RF signal and LO signal may include two or more waveforms, but also are referred to herein as singular unless otherwise noted.)

Typically, though not necessarily, the RF signal, LO signal, and modulation particulars of the RFPM may be sufficiently specified that the IF signal produced therefrom also is specific. That is, a previously known RF signal and LO signal, when combined with a previously known particulars of the RFPM, may be relied upon to produce an IF signal that also may be previously calculated (and/or previously measured, etc.). Thus, the IF signal may be characteristic of the specific combination RF signal, LO signal, and RFPM (at thus at least potentially distinguishable from other signals).

Still with reference to FIG. 1A, the IF signal is communicated from the RFPM to the IF emitter on the label. Moving on to FIG. 1B, with the IF emitter in operation the IF emitter transmits 0134 the IF signal. As noted previously with regard to the RF signal, typically though not necessarily the IF signal may not be directed at any specific device, and rather may blanket an area. Thus again, it may not be necessarily to establish communication protocols with any particular target for the IF signal, or to identify whether a suitable target exists.

Continuing in FIG. 1B, the IF signal, as generated by and emitted from the label, is received 0140 in the IF receiver of the smart phone. (As noted, the IF receiver of the smart phone may physically be the same device as the RF emitter of the smart phone, though this is not required.) The IF signal then is communicated 0142 to the processor of the cell phone.

The processor of the smart phone compares 0144 the IF signal to an IF signal standard, via executable instructions instantiated on the processor. For example, as noted previously the specific form of the IF signal may be predictable based on the RF signal, the LO signal, and the particulars of the RFPM. In such instance, the IF signal standard may be a relatively narrow description of a frequency, waveform, etc. as would be anticipated for the specific RF signal, LO signal, and RFPM. Such an IF signal standard may be essentially fixed and narrowly defined to a single very particular IF signal. However, the IF signal, and thus also the IF signal standard, may vary considerably, and not all embodiments will have such a fixed, narrowly defined IF signal standard (nor is such required).

If the IF signal satisfies the RF signal standard, the processor certifies 0146 the incoming IF signal as being representative of the activation of the adhesive label engaged with the eye drop bottle, in the processor of the smart phone via executable instructions. For the example embodiment under discussion with regard to FIG. 1A and FIG. 1B, this may be taken as evidence that the eye drop bottle has been squeezed, so as to dispense an eye drop therefrom. (If the IF signal does not satisfy the IF standard, then step 0146 and/or other steps subsequent to 0144 may not take place. Optionally, other events may take place instead, as discussed in more detail subsequently herein.)

For purposes of discussion herein, receipt of a certified IF signal may be referred to as a "contextual event" with regard to the taking of medication in the eye drop bottle. Taking the medication itself may be considered as a "medication event", proper; however, receipt of a certifiable IF signal may at least suggest that an event associated with taking the medication—namely, squeezing the bottle to dispense medication (and in the process providing a certifiable IF signal)—has taken place. Thus, whether or not a medication event has been directly detected, a certifiable IF signal may be understood as evidence that an event contextual to taking the medication has taken place. In more colloquial terms, whether or not it can be proved that the medication was used, there is at least objective evidence that the medication was dispensed.

However, while the example arrangement in FIG. 1A and FIG. 1B utilize a dispensing the medication as a contextual event, this is not limiting. Detecting a different contextual event, detecting the use of the medication proper (the medication event), detecting multiple events, etc., may also be suitable.

Continuing in FIG. 1B, the contextual event—that is, the dispensing of an eye drop—is registered 0150A, 0150B, and 0150C, along with an event time for that contextual event. In the example of FIG. 1B, the event and event time are recorded 0150A in a data store of the smart phone via executable instructions, are presented 0150B on a display of the smart phone via executable instructions, and are communicated 0150C by the smart phone to a medical care provider (e.g., a physician who prescribed the eye drop medication, a medical researcher conducting a clinical trial, etc.) via executable instructions. Recording, presenting, and communicating the contextual event (and the time thereof) 0150A, 0150B, and 0150C as registration are examples only, and other forms of registration also may be suitable.

Several matters are emphasized with regard to the example arrangement in FIG. 1A and FIG. 1B. While not all embodiments necessarily will exhibit all such features (nor are all embodiments required to do so), at least certain such features may be present in various embodiments.

The remote (in the form of the adhesive label) is for the most part a passive device. That is, the remote need only operate when medication is dispensed, and may be otherwise inert. Power for signaling that the event has taken place (that medication has been dispensed) is provided by the very event that is to be detected (dispensing the medication). Thus, no sustained power source may be required (though the presence of a battery, capacitor, or other power source is not necessarily excluded), no ongoing waste heat may be generated, any electromagnetic interference from the device may be temporary, etc.

Furthermore, the remote operates specifically because the medication is dispensed. The bottle is squeezed, the label distorts, the piezoelectric element is stressed/deformed and generates electricity, and once operational the RFPM produces the IF signal. Such an approach may be considered as "user transparent". That is, no special action is required by the user to cause the remote to function, beyond the normal dispensing of medication. Indeed, the user may not even be aware of that the remote is functioning. Thus, the approach does not rely on the user reliably reporting medication use, or reliably activating some system, etc. Registration that medication has been dispensed may be viewed as an autonomous side effect of the user dispensing the medication.

In addition, although the system may be considered "smart" in that events are sensed, data is logged, an authenticated profile of medication adherence may be provided, etc., the remote itself may be considered "dumb". In colloquial terms, at least some of the "smart" work is carried out somewhere other than the container: sensors, processing power, communications, etc. may be carried out by the base, some distance away. Thus, the remote may not have and may not require a processor, executable instructions, etc. While the presence of a processor is not necessarily excluded, the arrangement in FIG. 1A and FIG. 1B is operable with components that exhibit no internal decision-making, data-logging, etc. When the label is energized, the RFPM simply produces the IF signal from the RF and LO signals, inputs leading to outputs. Such dumb functionality by the remote may be well-suited for remotes that are compact, light, inexpensive, disposable, etc., even while the combination of remote and base (in the example of FIG. 1A and FIG. 1B, a smart phone) functions as a smart system.

Furthermore, it is noted that while signals may be generated and broadcast by both the base and the remote—the RF signal by the smart phone, and the IF signal by the adhesive label on the bottle—communication is not required to be carried within those signals. Rather, the existence of the signals itself may constitute the necessary communication. That is, it may not be necessary to modulate the IF signal in order to carry data indicating that medication has been dispensed, since the presence of an appropriate IF signal indicates by mere existence that the medication has indeed been dispensed. More colloquially, the IF signal does not have to carry a message; the IF signal is the message. Thus, communication protocols may not be required, since the base and remote may not be "connecting". (Though additional communication between base and remote that does utilize communication protocols, etc., is not prohibited.) Rather, the base produces an RF signal that enables creation of the IF signal, and the remote produces an IF signal such that the presence of that IF signal indicates that an event has taken place. Additionally, if communication is not carried by the contents of the IF signal (or the RF signal), the system may still function even with low signal strength, signal degradation, interrupted signals, etc. Consequently, communication in the arrangement of FIG. 1A and FIG. 1B may be reasonably described as "robust".

Figure 2A:
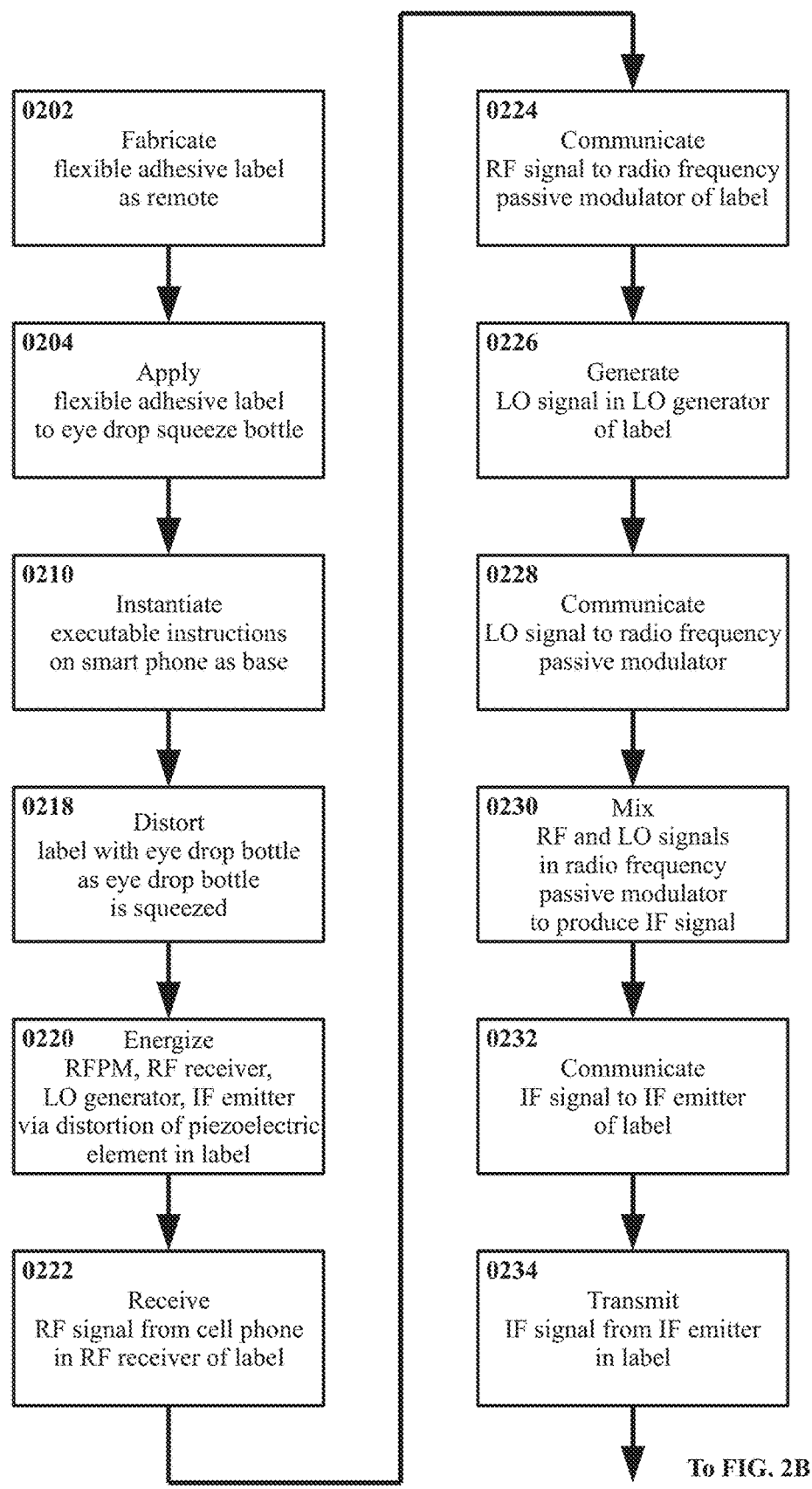
FIG. 2A and FIG. 2B depict another example method for determining the use of medication through radio frequency passive modulation, utilizing ambient RF signals, in flow chart form.
Figure 2B:
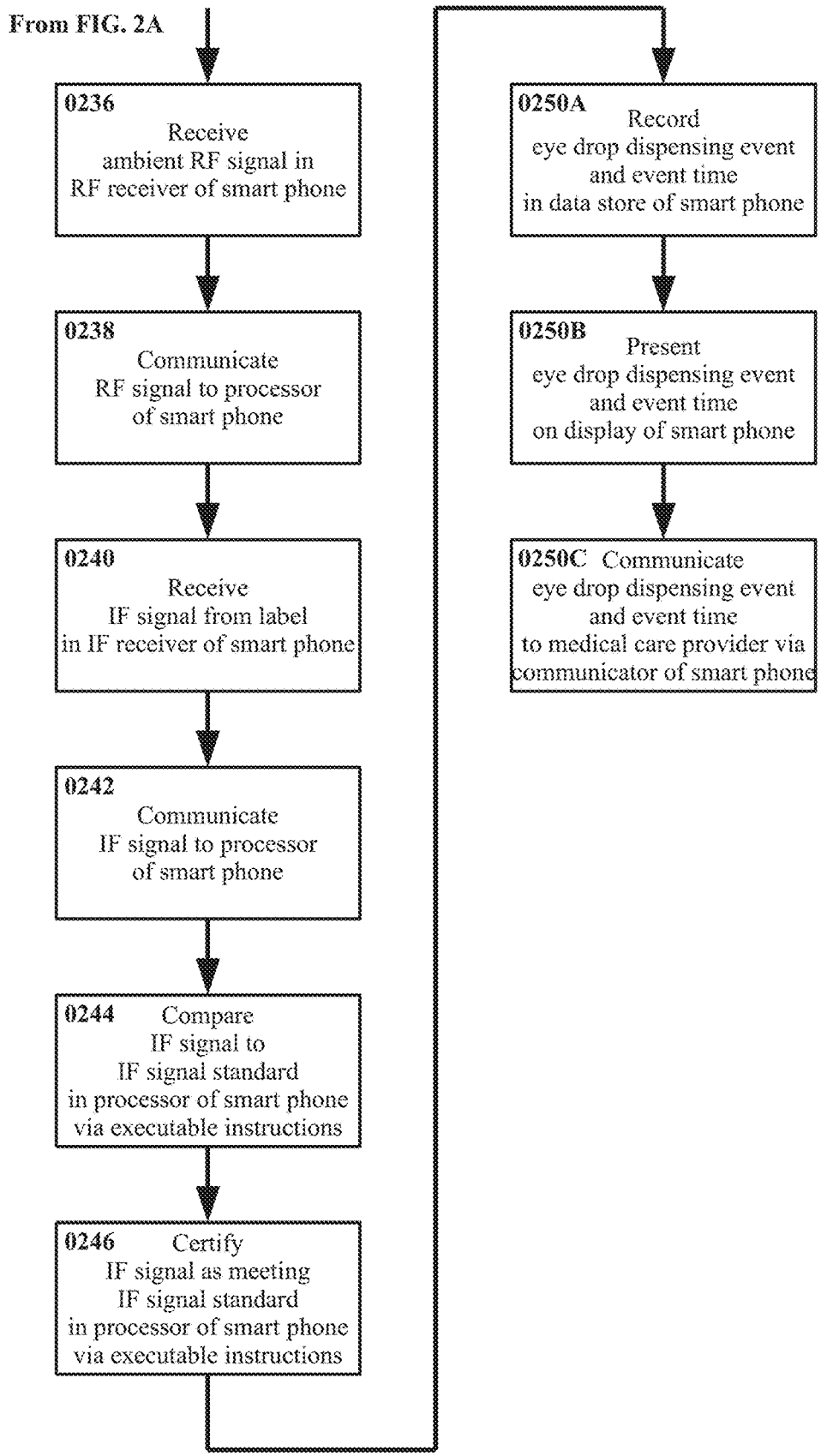

Now with reference to FIG. 2A and FIG. 2B, another example method for determining the use of medication through radio frequency passive modulation is presented in flow chart form. However, where the arrangement in FIG. 1A and FIG. 1B included generating an RF signal specifically for use in the method as shown, in FIG. 2A and FIG. 2B the RF signal is an ambient signal, as may be already be present.

With reference particularly to FIG. 2A, an adhesive label is fabricated 0202, the label is applied 0204 to a squeeze bottle to serve as a remote, and executable instructions are instantiated 0210 onto the processor of a smart phone serving as a base, similarly to what has been shown and described with regard to FIG. 1A.

However, it is emphasized that unlike in FIG. 1A, in FIG. 2A neither the smart phone nor any other element is required to generate or transmit a dedicated RF signal. Rather for the purpose of FIG. 2A it may be anticipated that some suitable RF signal may be available incidentally. Ambient radio frequency "noise" is widespread, since in principle nearly any electrical and/or magnetic function, whether natural or artificial, may produce radio frequency output. Common sources may include but are not limited to radio broadcasts, television broadcasts, emissions from hard line data communication (typically though not necessarily unintentional "leakage"), cellular network communications, Wi-Fi® signals, BLUETOOTH® signals, emissions from mains electricity ("house current"), emissions from transmission lines (e.g., high tension lines), emissions from fluorescent lights and/or other common electrical appliances, etc. In principle, even background solar radio emissions, auroral emissions, deep space emissions, etc., may be considered and/or utilized as an ambient RF signal.

Continuing in FIG. 2A, when the eyedrop bottle is squeezed to dispense medication, the label engaged with the bottle is distorted 0218. A piezoelectric element also is stressed and/or distorted therewith, and energizes 0220 an RFPM, RF receiver, LO generator, and IF emitter on/in the label. With the label elements so energized, the RF receiver receives 0222 an ambient RF signal and communicates 0224 that RF signal to the RFPM. The LO generator also generates 0226 an LO signal and communicates 0228 that LO signal to the RFPM. The RFPM then modulates 0230 the RF signal and LO signal to produce an IF signal and communicates 0232 the IF signal to the IF emitter. The IF emitter transmits 0234 the IF signal.

Now with reference to FIG. 2B, an RF receiver of the smart phone (which may or may not be physically the same element(s) as the RF emitter referenced in FIG. 1A, and/or which may or may not be physically the same element(s) as the IF receiver referenced subsequently herein in step 0240) also receives 0236 the ambient RF signal. The RF emitter then communicates 0238 the RF signal to the processor of the smart phone.

If multiple RF signals are present, the RF receiver may be adapted to receive all such signals, to receive only some such signals and exclude others (e.g., by wavelength, signal strength, etc.), to receive but not pass on at least some received signals, to pass on some or all signals as a single combined signal without identifying individual signals therein, or otherwise to either discriminate or not as may be suitable for a particular embodiment; embodiments are not limited in this regard. Discrimination and/or other signal processing of ambient RF signals, where present, may be carried out via executable instructions instantiated on the processor, by hardware in and/or engaged with the RF receiver, or through other approaches; embodiments also are not limited in this regard.

The IF receiver receives 0240 receives the IF signal, and communicates 0242 the IF signal to the processor. The processor compares 0244 the IF signal to an IF signal standard via executable instructions instantiated on the processor, and certifies 0246 the IF signal as meeting the IF signal standard via executable instructions instantiated on the processor (assuming, for the sake of illustration, that the IF signal does in fact satisfy the IF signal standard).

A contextual event (in this example, a medication dispensing event) is recorded 0250A along with an event time for that event in a data store of the smart phone. The event and event time also are presented 0250B via a display of the smart phone, and further are communicated 0250C to a medical care provider via a communicator of the smart phone (that communicator may or may not include the same hardware as the RF receiver or IF receiver).

Certain features as noted with regard to FIG. 1A and FIG. 1B likewise may apply to the example embodiment of FIG. 2A and FIG. 2B. In addition, for an arrangement that makes use of ambient RF signals as in FIG. 2A and FIG. 2B, it is noted that lack of a need to provide a dedicated RF signal may also have notable consequences. For example, if no additional signals are produced and broadcast beyond what may already be present, then no additional "noise" is contributed to the signal environment thereby. In addition, by not generating a dedicated RF signal the power consumption of the smart phone may be reduced, and/or the heat generation, etc.

In principle, there may exist areas that are sufficient "quiet" in radio noise that ambient RF signals may not be relied upon, or may not be relied upon in all cases. However, as noted radio noise is produced by many sources, including at least some natural sources, and is widespread in regions frequented by humans. Consequently, ambient RF may be reasonably expected to be present in at least many situations. In addition, while FIG. 1A and FIG. 1B addresses only the use of a dedicated RF signal, and FIG. 2A and FIG. 2B addresses only the use of an ambient RF signal, such uses are not necessarily exclusive. For example, a given embodiment may produce and use a dedicated RF signal in certain instances while using an ambient signal in other instances. Such embodiments may measure or otherwise evaluate whether suitable ambient RF signals are present (or are likely to be present), and utilize ambient RF signals when available but produce a suitable RF signal when ambient radio noise is inadequate. Numerous other variations may be possible for various embodiments, as well.

Figure 3A:
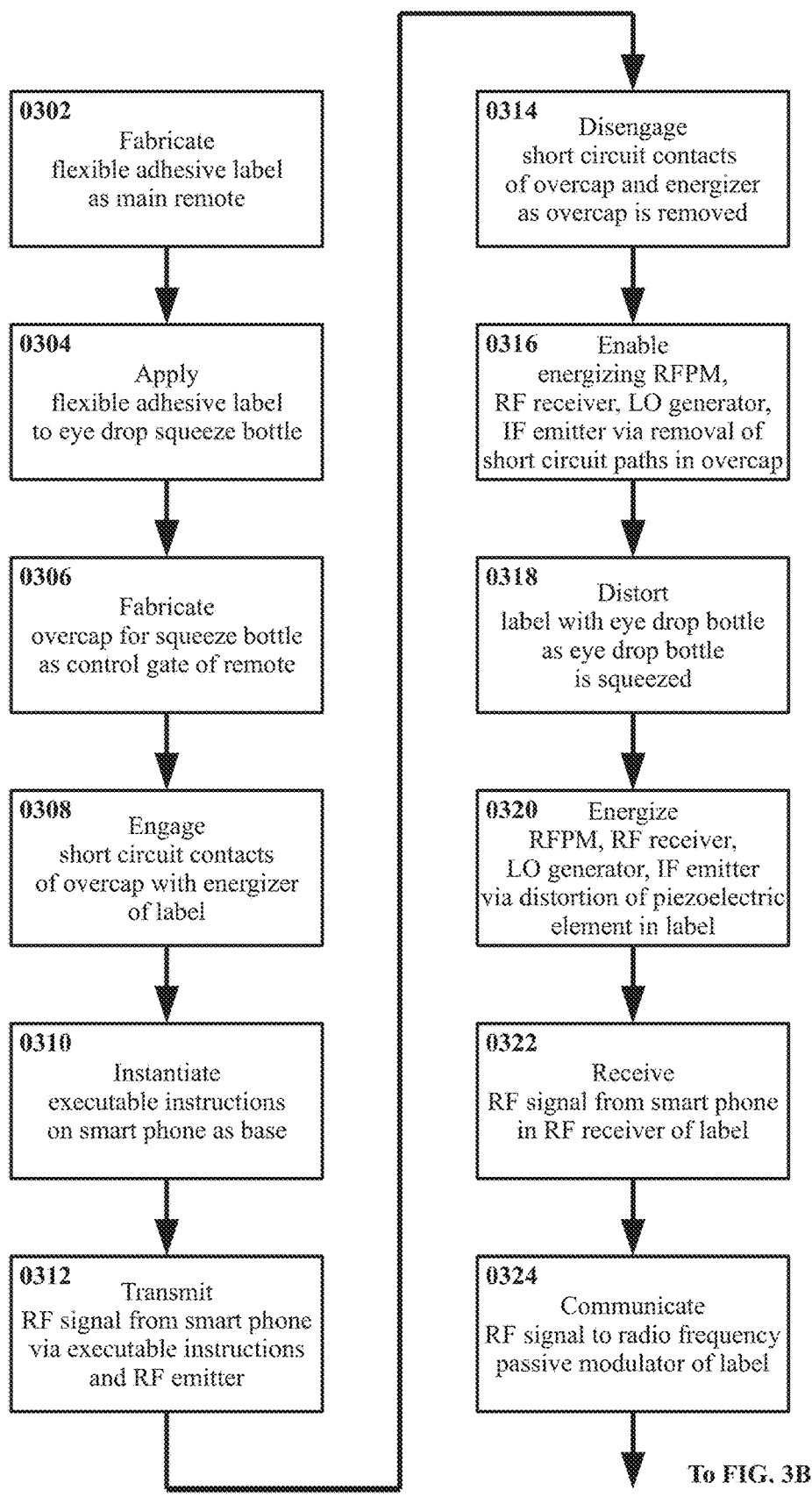
FIG. 3A and FIG. 3B depict another example method for determining the use of medication through radio frequency passive modulation, utilizing control gates to enable/disable energizing of certain components, in flow chart form.
Figure 3B:
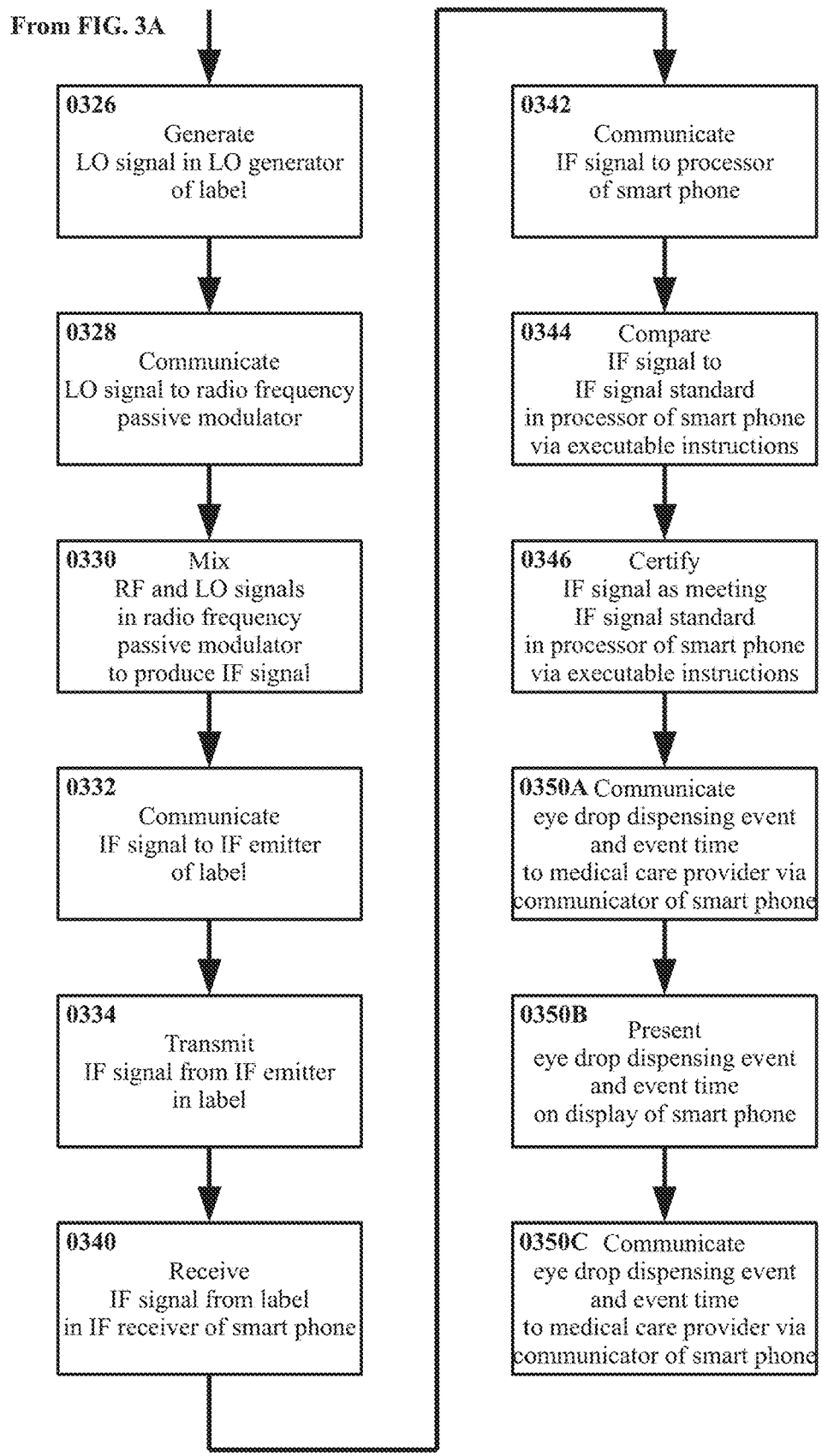

For example, with reference to FIG. 3A and FIG. 3B, in certain embodiments it may be useful to consider indications of medication use other than the event of dispensing the medication proper. In the arrangement of FIG. 3A and FIG. 3B, a control gate is utilized as a "go/no-go" system, so that the modulation of an RF signal with an LO signal is only enabled with the control gate in a positive state. Thus, with the control gate in a positive state ("on") the modulation is carried out (e.g., similarly as described with regard to FIG. 1A and FIG. 1B), while with the control gate in a negative state ("off") such modulation is not enabled.

Referring now specifically to FIG. 3A, an adhesive label is fabricated 0302, and the label is applied 0304 to a squeeze bottle to serve as a remote. In addition, an overcap (e.g., a second/exterior cover as may fit over an existing cap) for the bottle is fabricated 0306. The overcap may for example include a short-circuit path, such that when the overcap is engaged with the bottle, contacts on the overcap engage contacts in communication with the energizer (for example, contacts for the energizer may be disposed on/in the label; thus placing the overcap in physical contact with the label may dispose contacts for the overcap with contacts for the energizer). In such instance, the energizer may short through the short-circuit path rather than energizing components in/on the adhesive label (e.g., RFPM, RF receiver, LO generator, IF emitter). Continuing in FIG. 3A, the short circuit contacts of the overcap are engaged 0308 with the energizer. In such condition, the energizer is shorted through the overcap while the overcap is in place.

Executable instructions also are instantiated 0310 onto the processor of a smart phone serving as a base, similarly to what has been shown and described with regard to FIG. 1A. Continuing in FIG. 3A, an RF signal is transmitted 0312 from the smart phone via executable instructions and an RF emitter of the smart phone.

The short circuit contacts of the overcap are disengaged 0314 from the short circuit contacts of the energizer. For example, the overcap may be removed in order to dispense medication. Disengaging 0314 the short circuit contacts enables 0316 energizing—but does not in itself energize— an RFPM, RF receiver, LO generator, and IF emitter in/on the label. However, unless the overcap is so disengaged 0314, energy from the energizer may short through the overcap, so that the energizer may not provide energy to other components so as to modulate the RF signal with an LO signal. Thus, an indication that medication has been dispensed (e.g., signal modulation) may only be provided by the label if the overcap has been removed from the bottle, and the bottle then is squeezed while the overcap is absent.

Still with reference to FIG. 3A, when the eyedrop bottle is squeezed to dispense medication, the label is distorted 0318, and a piezoelectric element also is stressed and/or distorted therewith. The piezoelectric element energizes 0320 an RFPM, RF receiver, LO generator, and IF emitter on/in the label. With the label elements so energized, the RF receiver receives 0322 an ambient RF signal and communicates 0324 that RF signal to the RFPM. Moving on to FIG. 3B, the LO generator also generates 0326 an LO signal and communicates 0328 that LO signal to the RFPM. The RFPM then modulates 0330 the RF signal and LO signal to produce an IF signal and communicates 0332 the IF signal to the IF emitter. The IF emitter of the label transmits 0334 the IF signal.

The IF receiver of the smart phone receives 0340 receives the IF signal, and communicates 0342 the IF signal to the processor. The processor compares 0344 the IF signal to an IF signal standard via executable instructions instantiated on the processor, and certifies 0346 the IF signal as meeting the IF signal standard via executable instructions instantiated on the processor. A contextual event (e.g., a medication dispensing event) and an event time for that event are recorded 0350A in a data store of the smart phone, presented 0350B via a display of the smart phone, and communicated 0350C to a medical care provider via a communicator of the smart phone.

An arrangement such as is shown in FIG. 3A and FIG. 3B may exhibit certain useful features. For example, if the overcap must be removed to dispense medication, and removing the overcap disengages the contacts that otherwise would short circuit the energizer, then the use of such an overcap (or other control gate) may serve to inhibit at least certain false positives. It may be possible for a medication bottle to be squeezed even if there is no intention to dispense medication, and/or for the bottle to be squeezed when medication is not in fact being dispensed. For example, a bottle may be compressed in a pocket, in a bag, during rough handling, when dropped, etc. However, it may be expected that a cap (and thus an overcap) would be removed when dispensing medication from a bottle, while for a "false alarm" such as compressing the bottle in a pocket the overcap may remain in place. Thus, inhibiting the RFPM from operating while the overcap is in place (in FIG. 3A and FIG. 3B, by short circuiting the energizer) may avoid spurious IF signals from being produced, and thus such spurious signals may not be interpreted incorrectly as indicating that medication has been dispensed for use.

In more colloquial terms through the use of a control gate, at least certain "false alarms" may be avoided. As a result, the overall quality of data regarding the dispensing of medication may be improved.

In addition, as noted with regard to the use of medication container labels, adding an overcap—e.g., a second cap disposed over the first cap (assuming for descriptive purposes that the bottle includes a cap, though this is not required or limiting)—may not be considered a change to the medication container in a regulatory sense. Thus, just as adding a label to a medication container may not require new approval of the container, adding an overcap to the container may not require new approval. As with a label, an overcap may for example be considered packaging, and thus held to a different regulatory standard.

In addition, in the example of FIG. 3A and FIG. 3B, the overcap may be configured so that electrical contacts thereof engage with electrical contacts on the label. Thus, the additional "go/no-go" feature of smart functionality also may be retrofitted to existing "dumb" containers.

Figure 4:
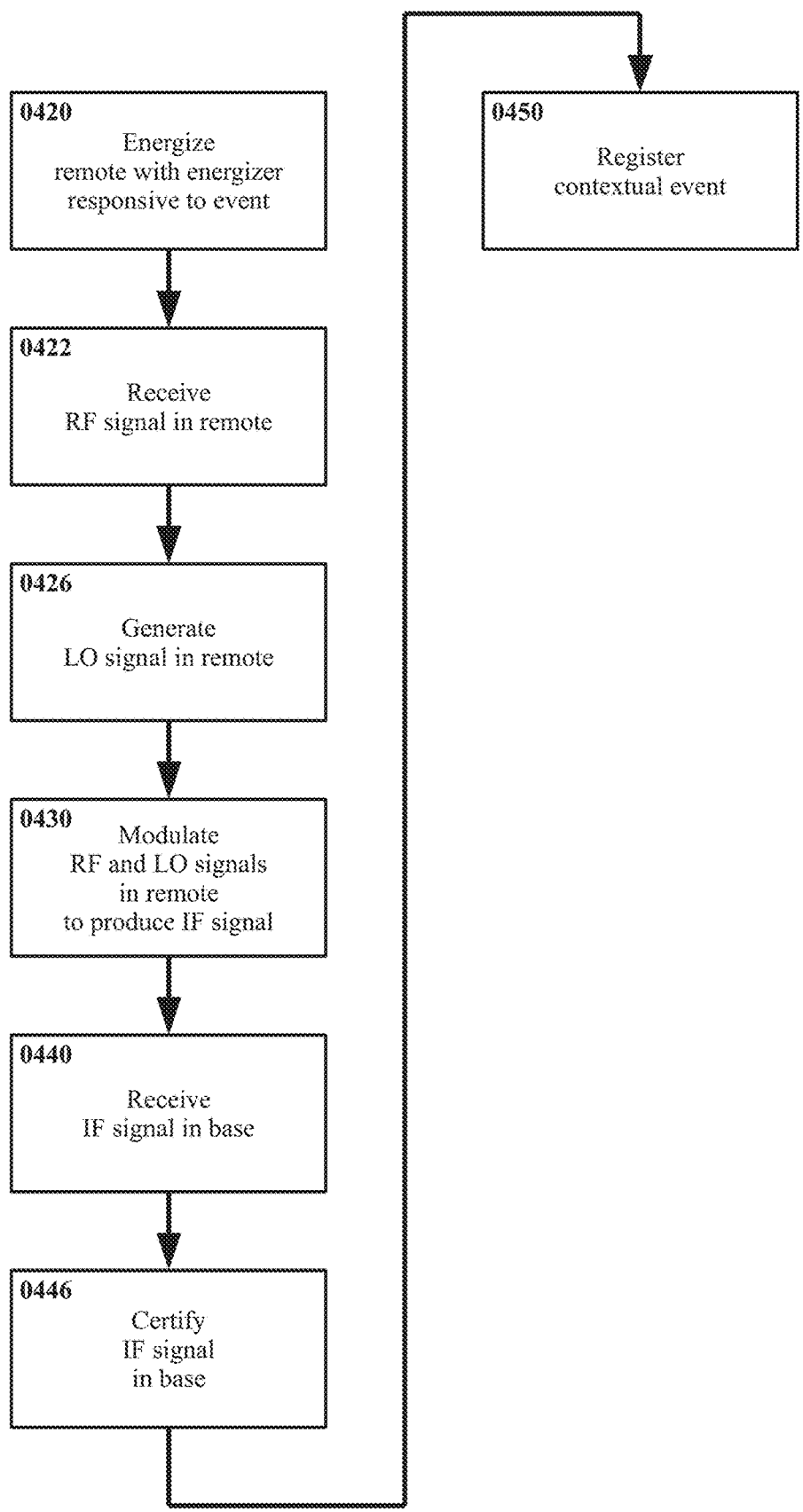
FIG. 4 depicts another example method for determining the use of medication through radio frequency passive modulation, in flow chart form.

As noted with regard to FIG. 1A through FIG. 3B, certain specific features are presented therein for clarity, such as a remote in the form of a label for a squeeze bottle, a base in the form of a smart phone, components and functions thereof, etc. However, these are examples only, and other arrangements may be equally suitable. Turning now to FIG. 4, a more generalized (though still not necessarily exhaustive or limiting) example method is illustrated therein.

In FIG. 4, an energizer of a remote 0420 energizes a remote in response to an event. For example, the event of interest may be a medication event, e.g., administering a medication such as disposing an eyedrop in a subject's eye, swallowing a pill, inhaling an atomized medication from an inhaler, injecting a medication, etc. However, the event also may be a contextual event for medication, that is, one that may be associated with administering a medication but that does not necessarily encompass administering the medication per se. For example, considering eyedrops as a medication, contextual events may include (but are not limited to) opening a bottle such as by removing the cap, manipulating the bottle in some manner associated with using the medication (such as by inverting the bottle over an eye), squeezing the bottle to dispense a droplet of medication, closing the bottle, and returning the bottle to a storage configuration. Other medications also may have other associated contextual events, in addition to or instead of those for eye drops. Embodiments are not limited with regard to the medication and/or delivery method (e.g., squeeze bottles, squeeze tubes, hypodermic syringes, auto-injectors, syrettes, bottles whether twist-cap, flip cap, or pull cap, inhalers/atomizers, single-dose cartridges, etc.).

In addition, events of interest are not necessarily required to be or limited to only medication-related events. Events associated with a piece of therapeutic equipment (such as may be used for physical therapy), a food container, a water tap, etc., could be considered. For example, a water tap fitted with suitable systems (e.g., an RFPM, etc.) may be made "smart" at least insofar as providing evidence that the tap is being used, used at some time, set to some level, etc., whether or not that water tap includes any integral power source, communication equipment, etc., and/or whether or not it was originally contemplated that the tap might provide such smart functionality. The particulars regarding events (and any mechanisms/methods associated with those events) may vary widely, and are not limiting.

Typically, though not necessarily, the energizer may be activated through manipulation or alteration of some physical initiator, subject to the event under consideration. For example, as in FIG. 1A through FIG. 3B a flexible portion of a label applied to a medication bottle initiator may be considered as an initiator; the label (or at least a flexible portion thereof) deforms when the bottle is squeezed to dispense medication, initiating subsequent steps that provide an indication that medication has been dispensed. Considering only medication containers as an example (and noting that embodiments are not limited only to medication containers), other initiators could include but are not limited to threaded caps, flip-top or pop-top caps, plungers in hypodermic needles, pistons or membranes in inhalers, frangible elements connecting a single-use container to a cap, an optical window adapted to pass light, an RF window adapted to pass radio frequency waves, an RF antenna, etc. Initiators may vary widely, and are not limiting.

In addition, initiation of an initiator may not be required for activating an energizer in a given embodiment. For example, if a piezoelectric element were applied directly to the outside of a container, squeezing the bottle may entail a user directly contacting and deforming the piezoelectric element, without any intervening physical or functional structure necessarily required. Also, in at least certain instances an initiator may reasonably be understood as being present, but may have no distinctive physical structure. For example, if an entire side-wall of a squeeze bottle and/or an entire label applied thereto is flexible, then it may be valid to consider the entire label and/or wall of the bottle as an "initiator" in some sense; however, it may be equally valid to consider such an arrangement as lacking an initiator, in that the structure that is present—e.g., the wall, the label, etc.—may not be "doing anything" in a well-defined sense. That is, a flexible wall may or may not be considered as a mechanism that initiates the energizer; to at least some degree, the matter of whether an initiator is present may be a question of definition. Embodiments are not limited with regard to how initiators are defined, what structure initiators may exhibit, whether an initiator is even present, etc.

Still with reference to FIG. 4, as noted the energizer energizes 0420 the remote. The energizer thus provides energy for carrying out certain further steps, e.g., modulating an RF signal with an LO signal. Typically, though not necessarily such energy may be electrical, though other arrangements (e.g., light, sound, heat, etc.,) may be suitable depending at least in part on the particulars of the system(s) used for modulation. In certain previous examples a piezoelectric element engaged with a flexible label of a squeeze bottle have been described as energizers, but embodiments are not limited only to piezoelectric elements. Other energizers may include but are not limited to plunger generators, rotary generators, photovoltaic elements, radio frequency (or other) power harvesters, triboelectric elements, and fractoelectric elements (e.g., frangible elements that generate electrical signals through being severed and/or broken). Certain energizers may be reusable (e.g., a piezoelectric element) while others may be single-use (e.g., fractoelectric elements).

The element(s) that the energizer energizes within the remote also are not limited, and may vary from one embodiment to another. Typically, though not necessarily, a remote may include an RFPM, an RF receiver, and LO generator, and an IF emitter (whether as discrete components, integrated into a single unit, or otherwise). However, certain embodiments may have different elements present. In addition, it may be suitable for an energizer to energize only one element or some elements as may be present in a remote, while other elements remain inactive, have independent energy sources, do not require energy, etc.

An RF signal is received 0422 in the remote. The RF signal may be a dedicated signal, for example as generated in a base station for receipt 422 by the remote. However, the RF signal also may be an ambient signal that may be present incidentally, for example electromagnetic waves from radio broadcasts or as noise that may be used opportunistically. The form, manner of generation, content, amplitude, wavelength, waveform, etc. of the RF signal is not limited.

Still with reference to FIG. 4, an LO signal is generated 0426 in the remote. The RF signal (whether dedicated or ambient) and the LO signal are modulated 0430 or "mixed" to produce an IF signal therefrom.

The IF signal is received 0440 in a base. In certain previous examples a base has been described in the form of a smart phone, but other arrangements also may be suitable. For example, a variety of other devices and/or systems may be suitable for use as a base, including but not limited to a smart watch, a tablet computer, a desktop computer, a laptop computer, a personal data assistant ("PDA"), a game console, and a head mounted display. In addition, it may be suitable to utilize a dedicated device as a base, for example manufacturing or otherwise providing a base specifically to cooperate with a remote in carrying out certain functions as described herein. Bases may be fixed or portable, dedicated or multi-purpose, specific to a single remote or group of remotes or universal, etc., and may vary in other aspects. So long as a given base is sufficient to carry out the functions required thereof, suitable bases are not otherwise limited.

The IF signal is then certified 0446 in the base. For example, the IF signal may be compared against a standard therefor. However, other approaches for determining whether a given candidate signal represents a valid IF signal (or does not) also may be suitable. As noted previously, in the event that a given candidate signal is not certified (e.g., having been determined to be a false positive), the subsequent steps may not be performed, and/or other steps may be performed in addition/instead.

However, if the IF signal is certified 0446, a contextual event is then registered 0450. For example, the receipt of a certified IF signal may be recorded in a data store, presented on a display, communicated to some external party, etc., and/or some combination thereof. The specific data that is recorded, presented, etc., is not limited. Typically, though not necessarily, a time of the event may be registered along with the presence of the event itself, though this is not required. Other information also may be registered, in addition or instead. For example, if the event under consideration is dispensing eye drops, the number of eye drops dispensed may be registered. Similarly, the medication name, patient ID, remote ID, base ID, etc., may be registered (assuming such data is available; it is not required that such information either be available or be registered for all embodiments). The nature and extent of information registered, and the manner of registration, are not limited.

As may be seen from a comparison of FIG. 4 with FIG. 1A through FIG. 3B, certain steps specific to particular embodiments in previous examples are not shown in FIG. 4, and/or are not separately/explicitly shown to be present in the arrangement of FIG. 4. While such steps are not necessarily required for all embodiments, it may be illuminating to address aspects of at least some such steps.

For example, with regard to the fabrication of a remote (steps 0102, 0202, and 0302 in FIG. 1A, FIG. 2A, and FIG. 3A respectively), it may be presumed that if a remote exists, then at some point that remote is fabricated or otherwise made available. While in certain instances the remote may be fabricated e.g., as an adhesive label, the form of a given remote, and the manner by which that remote is produced are not limited. Likewise, with regard to engaging a remote with a container (steps 0104, 0204, and 0304 in FIG. 1A, FIG. 2A, and FIG. 3A respectively), the manner by which that remote is engaged with a medication container (or other entity) are not limited. In addition, while labels and/or other remotes may be produced separately from a container and then engaged therewith, it is not required for a remote to be provided separately from a container. A remote may be configured integrally with a container, for example a plastic container may be injection molded with some or all elements of a remote molded therein so as to be fully encapsulated with the plastic (e.g., encased within the container wall, the container base, etc.).

Similarly, with regard to the fabrication of an overcap (step 0306 in FIG. 3A), again it may be presumed that if an overcap exists then that overcap was somehow made available, and at some point was engaged with a container (step 0308 in FIG. 3A). As the manner through which an overcap (if present) may be provided and the manner by which an overcap may be engaged are not limited, for at least certain embodiments the producing/acquiring of an overcap and engagement/installation thereof may not be considered with regard to the operation thereof. A patient using a medication may not provide the container, cap, etc., and may not even be aware (or need to be aware) of how the container, cap, etc. were produced.

The manner of providing a remote, container, label, cap, overcap, elements thereof, etc., is not necessarily required to be performed by the user and thus may not be part of an embodiment specific to the use of medication. For example, as may be seen FIG. 4 does not include steps related to providing a label, an overcap, etc. However, consideration of fabrication and/or other production approaches for a remote, container, label, cap, overcap, elements thereof, etc. also is not excluded. For example, certain embodiments may address the specific form, manner of production, etc., of an adhesive label serving as a remote, an overcap with short circuit pathways serving as a control gate, and so forth.

With regard to instantiating executable instructions, certain previous examples refer to instantiating executable instructions onto a processor of a smart phone (e.g., steps 0110, 0210, and 0310 in FIG. 1A, FIG. 2A, and FIG. 3A respectively), and of carrying out functions with such executable instructions such as transmitting an RF signal, comparing an IF signal to a standard, certifying an IF signal, etc. However, embodiments are not limited to the use of executable instructions for such functions, to the instantiation of executable instructions onto a smart phone, or to the use or presence of executable instructions at all. For example, it may be suitable to carry out functions with hardware or through other approaches, in addition to or instead of utilizing executable instructions. Similarly, where present executable instructions may be instantiated onto devices and/or systems other than a smart phone, and may carry out different functions from those presented as examples herein. Furthermore, even when executable instructions are present in a given embodiment, not all such executable instructions presented as examples necessarily will be present, or necessarily will be used. For example, an embodiment that utilizes ambient RF signals may not have, and/or may not make use of, executable instructions adapted to generate and/or transmit a dedicated RF signal. The presence, absence, form, and/or function of executable instructions is not limiting, and not all embodiments necessarily will or must include executable instructions.

With regard to ambient and dedicated RF signals, different embodiments may make use of different RF signals. For example, the arrangement of FIG. 1A and FIG. 1B produces a dedicated RF signal, while the arrangement of FIG. 2A and FIG. 2B utilizes an existing ambient RF signal. In addition, different embodiments may use different dedicated and/or ambient RF signals. For instance, two or more different dedicated RF signals may be generated and transmitted, e.g., so as to address two different remotes with the same base. Likewise, two or more different ambient RF signals may be utilized, and/or ambient RF signals may be selected from among existing RF signals without using any or all such. Furthermore, it may be suitable in some embodiments to utilize dedicated RF signals in certain cases and ambient RF signals in other cases. For example, if a suitable ambient RF signal is present that ambient RF signal may be used without a dedicated RF signal being produced, while if at some point no suitable ambient RF signal is available a base may then produce a dedicated RF signal. Other arrangements also may be suitable, and the production, selection, and/or use of various RF signals (dedicated or ambient) is not limiting, and particular steps and/or functions relating to RF signals may not be present in all embodiments.

With regard to communication of signals, such as transmission of an RF signal by a base (e.g., 0112 in FIG. 1A), receipt of an RF signal in a remote (e.g., 0122 in FIG. 1A), internal communication of an RF signal from a receiver to an RFPM (e.g., 0124 in FIG. 1A), etc., the particulars of such communication may vary from one embodiment to another. For example, if an RFPM (or other modulating entity) in a given embodiment may receive an RF signal directly without relying on a distinct RF receiver, then communication from the non-existent RF receiver to the RFPM may not happen. Particulars of communication are not limiting, and not all embodiments will exhibit or require all communications presented in examples herein. Moreover, for at least certain embodiments it may be reasonable to presume that if a signal is received, that signal was transmitted, otherwise produced, etc. Thus not all examples necessarily may explicitly refer to such communications.

With regard to modulation, in certain examples (e.g., FIG. 1A, FIG. 2A, FIG. 3A) modulation of an RF signal and an LO signal to yield an IF signal is carried out by a radio frequency passive modulator or RFPM. However, the particulars of how signals may be modulated are not limiting, and thus not all embodiments necessarily will utilize such an arrangement.

Certain examples herein (e.g., 0144 in FIG. 1B, 0244 in FIG. 2B, 0344 in FIG. 3B) include the presence of an IF signal standard and comparison of a received IF signal thereto. However, this is an example only. The manner by which a signal may be determined to represent an authentic IF signal (and thus at least potentially indicative of a medication event, contextual event, etc.) is not limited. While certain embodiments may include an IF signal standard and/or may compare incoming signals to that IF standard, other arrangements may be suitable.

With regard to registration, as may be seen in several examples herein (e.g., FIG. 1B, FIG. 2B, FIG. 3B) registration may take various forms, including but not limited to recording information in a data store, presenting information via a display, and communicating information to some external party. In addition, different embodiments may register various information, including but not limited to an event (such as a medication event, contextual event, etc.), an event time, an ID of one or more devices associated with the event (such as a serial number for a remote), an ID of the medication associated with the event (the type, dosage, intended function, etc.), an ID of a person associated with the event (the person for whom the medication was prescribed), and so forth. The nature and content of registration is not limited, and various embodiments may carry out registration in a variety of forms.

Now with reference to FIG. 5 through FIG. 16, several examples of squeeze bottles and remotes engaged therewith (e.g., applied thereto, incorporated therein, etc.) are shown. It is emphasized that embodiments are not limited only to squeeze bottles, rather certain examples addressing squeeze bottles are presented for explanatory purposes.

Figure 5:
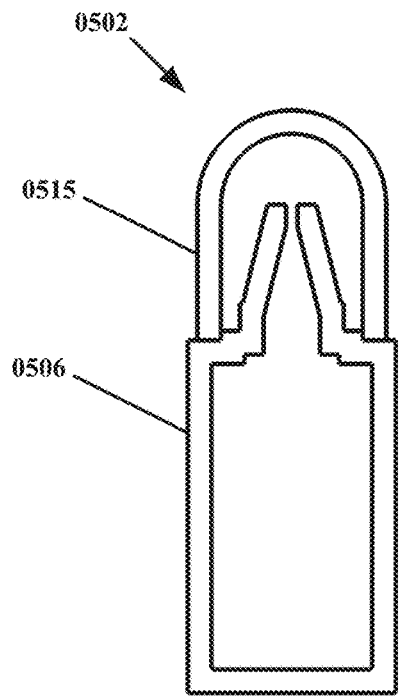
FIG. 5 through FIG. 8 depict example arrangements of squeeze bottles and remotes in the form of labels engaged therewith as may be suited for determining the use of medication through radio frequency passive modulation, in cross-section.

Specifically with regard to FIG. 5, a squeeze bottle container 0502 is shown therein in cross-section. The container 0502 includes a wall 0506 enclosing a volume adapted to accommodate a medication (not illustrated) and to be dispensed from a nozzle (illustrated but not individually numbered). The container 0502 also includes a cap 0515 as may protect the nozzle, avoid contamination of the medication, restrict leakage, etc.

Figure 6:
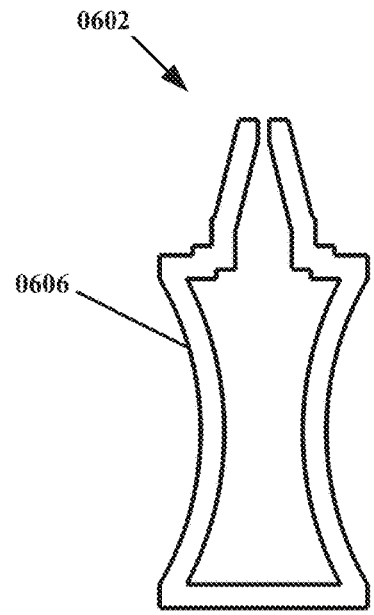

Turning to FIG. 6, a squeeze bottle container 0602 is again shown, similar to that in FIG. 5. However, as may be seen in FIG. 6 the wall 0606 of the container 0602 is deformed inward. Such deformation may for example be produced by a person (not illustrated) squeezing the sides of the container 0602 so as to expel medication therefrom. FIG. 6 shows no cap for the container 0602; as may be understood, when dispensing medication the cap (if any) for the container 0602 may be removed. The No remote or components thereof are shown engaged with the container in either FIG. 5 or FIG. 6. The arrangements shown in FIG. 5 and FIG. 6 may be considered as a baseline of sorts. That is, FIG. 5 and FIG. 6 may be an illustration of structure and function for an example container, so as to illuminate the structure and function of a remote engaged therewith as shown subsequently herein.

Figure 7:
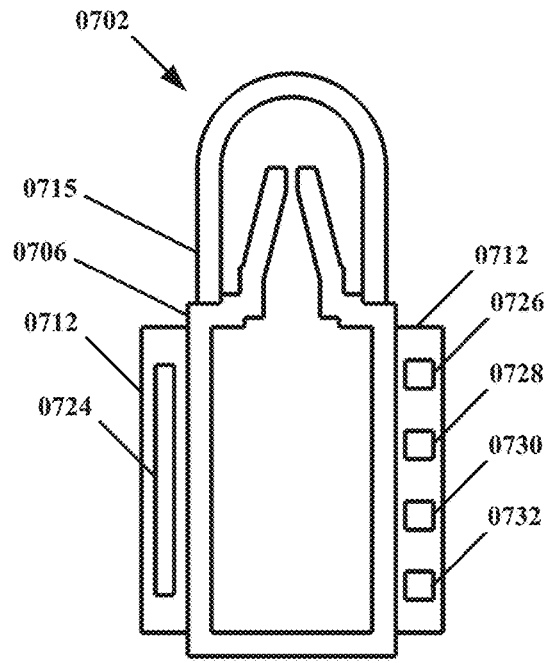

Now with reference to FIG. 7, a squeeze bottle container 0702 is again shown. As may be seen, the container 0702 includes a wall 0706, a cap 0715, and an overall configuration similar to that in FIG. 5. As may be understood, it may not be necessary to modify an existing container in order to accommodate a remote. Rather, a remote may be applied to a container, with little or no change to the container itself. (However, modifications to a container proper are not prohibited.)

In addition, FIG. 7 shows a label 0712 engaged with the container 0702, e.g., wrapped around the container and secured with adhesive, through friction (such as by heat-shrinking the material of the label 0712), etc. The particulars of the label and the manner of engagement are not limited. As may be seen, a remote energizer 0724 in the form of a piezoelectric element is disposed within the label 0702, for example being laminated as one of several layers in a multi-layer label, cast into a plastic sheet employed as a label, etc. Likewise, several additional elements 0726, 0728, 0730, and 0732 are disposed within the label 0712. In particular, a remote RF receiver 0726, a remote RFPM (radio frequency passive modulator) 0728, a remote LO generator 0730, and a remote IF emitter 0732 are shown as present. For example, such elements 0724, 0726, 0728, 0730, and 0732 may be embedded in the label 0712, and the label wrapped around the container 0702. (It is noted that the use of the prefix term "remote" herein, e.g., for example "remote IF emitter", is used in a structural/possessive sense, to indicate that an IF emitter or other element is associated with the remote. The term remote should not necessarily be understood as an adjective, to imply that such an IF emitter for example necessarily is distant from some other entity. Also, it should not be inferred that a second IF emitter necessarily exists somewhere else, though the existence of another IF emitter or other element also is not necessarily prohibited.)

For simplicity, electrical connections among the remote energizer 0724, remote RF receiver 0726, remote RFPM) 0728, remote LO generator 0730, and remote IF emitter 0732 are not explicitly shown. Typically though not necessarily, the remote energizer 0724, remote RF receiver 0726, remote RFPM) 0728, remote LO generator 0730, and remote IF emitter 0732 may be in communication with one another for functional purposes (e.g., the RFPM 0728 may receive an RF signal from the remote RF receiver 0726, etc.). Likewise, typically though not necessarily the remote energizer 0724, remote RF receiver 0726, remote RFPM) 0728, remote LO generator 0730, and remote IF emitter 0732 may be in communication with the remote energizer 0724 so as to be energized (e.g., receive electrical energy therefrom) when the remote energizer 0724 is activated.

Figure 8:
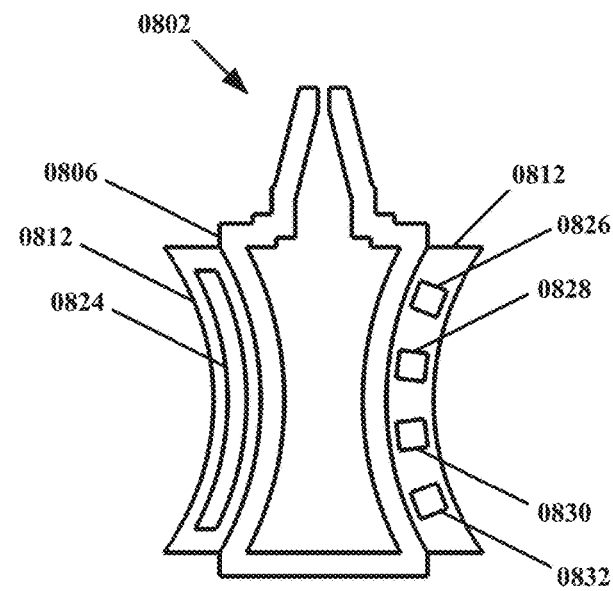

Now with regard to FIG. 8, an arrangement at least somewhat similar to that in FIG. 7 is shown. The arrangement in FIG. 8 includes a container 0802 with a wall 0806, and a label 0812 engaged therewith. A remote energizer 0824 in the form of a piezoelectric element is disposed within the label 0812, as are a remote RF receiver 0826, a remote RFPM 0828, a remote LO generator 0830, and a remote IF emitter 0832. However, as may be seen in FIG. 8 the wall 0806 of the container 0802 is deformed inward on either side, for example as may occur if the container 0802 is squeezed to dispense a dispersal of eye drop medication therefrom. In particular, it is noted that the piezoelectric element 0824 is deformed with the wall 0806 of the container 0802 (along with the label 0812 in which the piezoelectric element 0824 is disposed). Such deformation of the piezoelectric element 0824 may be expected to produce an electrical output from the piezoelectric element 0824, which then may be communicated to the remote RF receiver 0826, remote RFPM 0828, remote LO generator 0830, and remote IF emitter 0832.

Consequently, as the container 0802 is deformed, the remote RF receiver 0826, remote RFPM 0828, remote LO generator 0830, and remote IF emitter 0832 may receive energy and carry out certain functions. For example, if an RF signal (whether ambient or dedicated) is extant the remote RF receiver 0826 may receive that RF signal. That RF signal then may be communicated to the remote RFPM 0828. Also, the remote LO generator 0830 may produce an LO signal, and that LO signal then may be communicated to the remote RFPM 0828 as well. Further, the remote RFPM 0828 may modulate ("mix") the RF signal with the LO signal to produce an IF signal. That IF signal then may be communicated to the remote IF emitter 0832, and the remote IF emitter 0832 then may broadcast (or otherwise output) that IF signal, e.g., as may be received by a base (not shown in FIG. 8).

In more colloquial terms, for an arrangement as in FIG. 8 squeezing a drop of medication from the bottle may result in a recognizable signal being produced and broadcast, through the action of various elements within the label. The bottle 0802, the remote overall, and components 0824, 0826, 0828, 0830, and 0830 may be inactive otherwise; a piezoelectric element 0824 may be effectively inert when not being deformed/stressed, and electrically operated components 0826, 0828, 0830, and 0830 may likewise be inert if no electricity is available (e.g., from the piezoelectric element). Thus, even if an RF signal is being broadcast, and the remote is engaged with the container 0802, the remote may only produce a characteristic IF signal when the container 0802 is squeezed so as to expel medication. Consequently, the IF signal, if present, may be considered as an indication that medication is being dispensed (similarly, such dispensing of medication may in turn be interpreted as evidence that medication is being administered).

It may be illuminating to draw attention to certain features of an arrangement such as in FIG. 8.

It is noted that at least certain embodiments may be considered "user-transparent". For example, the very action of dispensing medication—in the example arrangement of FIG. 8, deforming a bottle 0802 to squeeze out a droplet—may initiate operation of the remote so as to produce an IF signal. Thus in order to register the medication being dispensed, no action may be required of a user beyond dispensing the medication: if a droplet is expelled by squeezing the bottle, and squeezing the bottle to expel the droplet also leads to the emission of an IF signal, then providing an IF signal as an indication that medication has been dispensed may be considered as user-transparent. While the embodiment may perform additional functions (e.g., registration) such functions may place few or no demands on the user. For example, users may not be required to manually record that medication was dispensed, or even to push a button, speak a voice input, or otherwise perform actions or even give attention to registering that medication is being dispensed. The user may not even be required to know how medication is being registered, or that medication is being registered at all, at least on a technical level. In more colloquial terms, the user may not have to "do anything" in order to register medication use; the act of dispensing the medication in itself may cause medication use to be signaled.

It is also noted that (in addition to or in place of being user-transparent), operation of at least certain embodiments may be considered consequential. That is, as in the example shown in FIG. 8, the IF signal may be sent as a consequence of dispensing medication. In the arrangement in FIG. 8 the piezoelectric element 0824 is deformed and so produces energy as the bottle 0802 is squeezed, and that energy activates various components 0826, 0828, 0830, and 0832 which in turn produce and emit an IF signal. Sensors to detect applied forces, finger contact, liquid exiting the nozzle, etc., are not required (though such sensors may not necessarily be prohibited); rather, the remote produces the IF signal as a consequence of dispensing the medication, being driven by the act of dispensing the medication. While embodiments may vary, intermediaries such as sensors, processing, etc. may not be required. Such an arrangement may be understood as being operationally robust, at least for certain embodiments.

It is also emphasized that data may not necessarily be encoded in the IF signal in an ongoing manner. The IF signal may not contain a message indicating that medication has been dispensed, so much as the existence of a characteristic IF signal may itself be the message that medication has been dispensed. As an analogy, the IF signal may more closely approximate a lantern hung in a window as a simple indicator (e.g., "one if by land, two if by sea") rather than a Morse code message encoded in flashes of light. Such an arrangement wherein an IF signal itself is the message may be considered as relatively robust communication, for example in that it may not be necessary to establish communication protocols, to encode data into the IF signal or decode data out of the IF signal (and thus hardware for such tasks may also not be necessary), risks of signal interruption/corruption may be low (if there is no encoded message in a signal to begin with, no encoding can be lost if that signal is interrupted or corrupted), etc.

Even so, an IF signal nevertheless may be sufficiently characteristic as to be readily identifiable. For the arrangement in FIG. 8 the LO generator 0830 and RFPM 0828 may be selected for particular properties; thus the nature of the LO signal and the specific modulation performed may be selected, or at least known beforehand. Even if the RF signal is not specified or known beforehand (e.g., being a local ambient signal), the particulars of the LO signal and modulation may result in a readily-identifiable IF signal. Thus, it may be possible to provide an IF signal that may be identified with confidence as being from the remote, distinguished from other signals and/or noise, and possibly even identified specifically as being from one particular remote (or a class of similar remotes). For example, it may be possible based on the nature of a detected IF signal to determine that that IF signal was produced by a remote belonging to a specific patient, engaged with a specific container, associated with a specific medication, part of a specific clinical study, etc. Again, it may not be required that the information be carried in the IF signal per se, rather the IF signal may be sufficiently characteristic as to be distinguishable from other similar signals, and/or possibly even uniquely identifiable.

As another matter, it is noted that an IF signal typically may not be continuous, rather the IF signal may be emitted for a relatively short duration. Electrical output from a piezoelectric element 0824 typically may be produced during and/or shortly after stress is applied thereto; once stresses on the piezoelectric element 0824 are no longer present (or at least are no longer changing), the piezoelectric element 0824 may cease to provide electrical energy. Thus, the remote RF receiver 0826, remote RFPM 0828, remote LO generator 0830, and remote IF emitter 0832 may be energized for a relatively short duration, and likewise the IF signal may be emitted for a relatively short duration. While certain approaches may be employed to store power (e.g., in a capacitor) and/or otherwise extend the time period during which electrically operated components 0826, 0828, 0830, and 0830 are energized, typically the remote may only produce an IF signal for a brief time. Thus, production of an IF signal typically may be intermittent, occurring when medication is dispensed as opposed to being produced continuously or near-continuously.

Such intermittent operation in itself may be a useful feature. For example, if production of an IF signal responsive to deforming the container is sufficiently brief, it may be that expelling two droplets of medication may result in two distinct periods during which the IF signal is emitted, with a gap in between; such an arrangement may enable determination of additional information such as the dose of medication being dispensed, e.g., how many drops? Likewise the period(s) when the IF signal is emitted and intervals therebetween may be evaluated to determine with at least some confidence whether drops were placed in both eyes (e.g., based on detection of two droplets, followed by two more droplets shortly thereafter).

In addition, depending on the particulars of a given embodiment, the period for which a piezoelectric element 0824 (or other energizer) provides electricity may be so brief that the IF signal is produced only while the bottle 0802 is being deformed, that is, when the wall 0806 of the bottle 0802 is changing shape. In such instance, if the bottle 0802 (and likewise the energizer 0824) is held in a deformed condition but does not further change shape, the energizer 0824 may not provide energy while so held. Rather, energy may be provided as the bottle 0802 is being squeezed, and as the bottle 0802 is being allowed to relax towards a default shape, but not during an interval between the squeeze and release. Consequently, the IF signal may be generated in two brief pulses, one as the bottle 0802 is squeezed and one a short time interval later as the bottle 0802 is relaxed. The presence of two or more such pulses, the interval(s) therebetween, and so forth may reveal useful information regarding how medication is being dispensed. For example, pulse patterns may be read to indicate that a subject is hesitating while attempting to squeeze out a droplet, etc. Even if the precise reasons for and/or meaning of a given pulse pattern are not understood, analysis of such patterns may still prove revealing, e.g., if the pulse pattern is atypical then the observation that something unusual/unexpected is taking place may in itself be useful.

Thus, while it is not required that production of an IF signal necessarily be brief, or of any particular duration, production of discrete and/or short-duration IF signal pulses is not necessarily problematic, and may be useful. Embodiments are not limited with regard to the duration, number, configuration, etc., of IF signal pulses produced (or necessarily to pulsed IF signaling itself).

In another potential aspect of various embodiments, it is noted that an RFPM typically may in some sense be considered as an "on or off" element. That is, an RFPM may either modulate two incoming signals into a third signal, or not. "Half mixes" due to inadequate voltage or current to a given RFPM, IF emitter, etc., or other factors, may not be observed. While at least in principle the certain properties of an IF signal (e.g., amplitude, etc.) may vary with factors such as how much energy may be supplied to the IF emitter 0832, the structure of the IF signal itself may be relatively insensitive to such variations.

Also, in at least some embodiments when a remote is not being activated to produce an IF signal, that remote may be essentially inert and/or passive, e.g., with no elements energized, operational, etc. Elements that depend on continuous or near-continuous power—for example, active sensors continuously gathering data to detect dispensing of the medication, a processor continuously operating to interpret sensor data as may be received, transmitters/receivers for sending/receiving information in an ongoing manner, etc.—may not be required. Indeed, while the functionality of a remote as shown in FIG. 8 may be described as "smart", the hardware itself at least arguably may be referred to as "dumb": no sensors, processor, etc., are shown or are required for the example therein, and such elements as are shown may remain inert except for brief periods. Such arrangements, where the remote and/or components thereof may not be "powered up" except when specifically needed to indicate that medication is being dispensed, and/or wherein the necessary elements may be few in number and simple in function, may exhibit operational advantages. For example, a remote wherein components thereof are active only for brief periods and are otherwise inert may have low demand for power (perhaps even zero demand when not being actively operated), low heat output, etc. Such intermittently functional and/or a "dumb" features of remotes may in at least certain embodiments contribute to low weight, low cost, physical robustness, etc. In colloquial terms, a simple system may have advantages from its very simplicity.

Moving on to FIG. 9 through FIG. 16, embodiments of a remote may vary considerably, and certain additional example embodiments (though by no means all possible embodiments) are presented.

Figure 9:
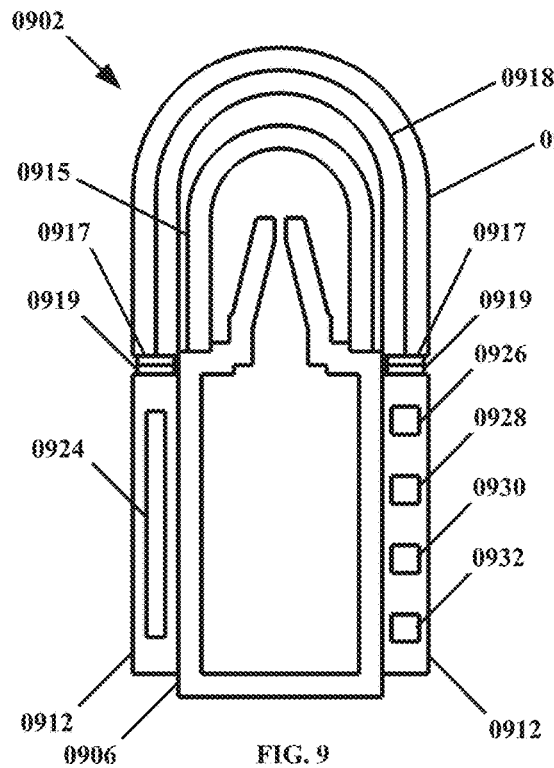
FIG. 9 through FIG. 12 depict example arrangements of squeeze bottles and remotes engaged therewith including a short-circuit control gate, as may be suited for determining the use of medication through radio frequency passive modulation, in cross-section.

With regard specifically to FIG. 9, therein a container 0902 is shown, including a wall 0906 and a cap 0915. A remote label 0912 is engaged with the wall 0906 of the container 0902, the remote label 0912 having disposed therein a remote energizer 0924 in the form of a piezoelectric element, a remote RF receiver 0926, a remote RFPM 0928, a remote LO generator 0930, and a remote IF emitter 0932. In at least certain aspects the arrangement in FIG. 9 may be seen as similar to FIG. 7.

However, as may be seen the arrangement in FIG. 9 also includes a remote overcap 0916, the remote overcap 0916 engaging with the container 0902 in such manner as to cover and/or limit access to the cap 0915. For example, it may be necessary to remove the remote overcap 0916 in order to access and remove the cap 0915. The remote overcap 0916 includes therein a remote control gate 0918 in the form of a short circuit path within the remote overcap 0916. The remote overcap 0916 also includes remote overcap contacts 0917 in communication with the short circuit path 0918. Furthermore, the remote label 0912 includes remote label contacts 0919, shown in FIG. 9 to be engaged with the remote overcap contacts 0917.

Internal electrical/data paths within the label 0912 are not shown in FIG. 9 for purposes of simplicity. (Example electrical/data paths are presented in certain subsequent examples herein, e.g., FIG. 18.) However, in the arrangement shown in FIG. 9 it may be understood that the remote label contacts 0919 may be in electrical communication with the energizer 0924, such that the energizer is short-circuited through the remote label contacts 0919, the remote overcap contacts 0917, and the short-circuit path in the remote overcap 0916 serving as the remote control gate 0918.

Figure 10:
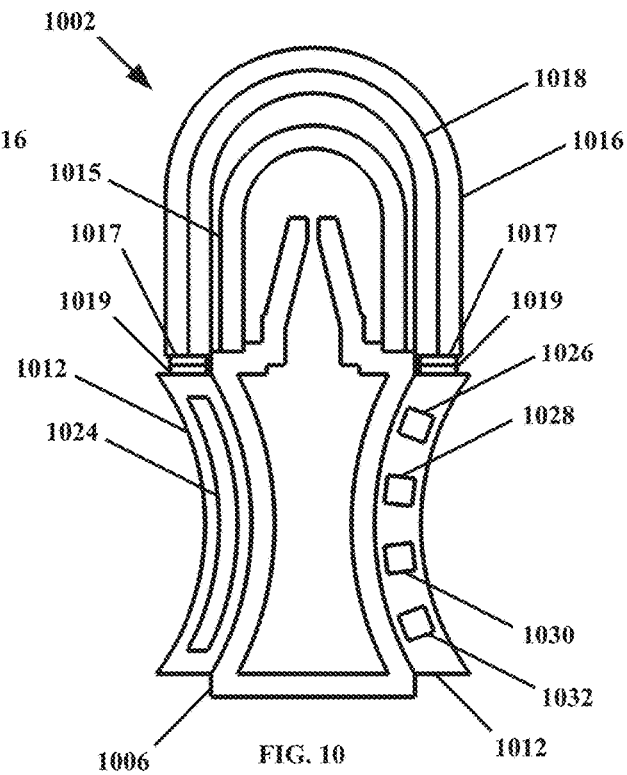

Turning to FIG. 10, an arrangement at least somewhat similar to that of FIG. 9 is shown, with a container 1002 including a wall 1006 and a cap 1015, with a remote label 1012 engaged with the wall 1006 of the container 1002. A remote energizer 1024, a remote RF receiver 1026, a remote RFPM 1028, a remote LO generator 1030, and a remote IF emitter 1032 disposed within the remote label 1012. A remote overcap 1016 with a remote control gate 1018 in the form of a short circuit path and remote overcap contacts 0917 also are shown, as well as remote label contacts 0919.

However, as may be seen in FIG. 10 the wall 1006 of the container 1002 is deformed inward. In certain previous examples, deformation of a container wall may energize elements of a remote leading to the emission of an IF signal. However, in the arrangement of FIG. 10 the remote overcap 1016 remains engaged with the container 1002. Consequently, electricity generated by deforming the piezoelectric element 1024 may be short-circuited through the short-circuit pathway serving as the remote control gate 1018 (via the remote label contacts 1019 and the remote overcap contacts 1017); in such instance electricity may not reach one or more of the remote RF receiver 1026, remote RFPM 1028, remote LO generator 1030, and remote IF emitter 1032, and consequently an IF signal may not be emitted. In effect, power that otherwise may lead to production of an IF signal (which may then be detected as indicating medication has been dispensed) may be diverted to a short-circuit, so that no such signal may be sent.

An arrangement such as is shown in FIG. 10 may be useful for example in avoiding certain false positive IF signals. For example, certain circumstances may occur wherein the container wall 1006 may be deformed when a user is not attempting to dispense medication from the container 1002. If a container 1002 were to be carried in a pocket, purse, bag, etc., forces may be applied to the container 1002 by contact with other carried objects, through motions of walking, sitting, etc., and so forth. Likewise, certain persons may be inclined to fidget with a medication container 1002, potentially deforming a wall 1006 thereof. Such deformations, even if not associated with dispensing medication, may activate a remote energizer 1024, potentially leading to emission of a false positive IF signal. However, with an overcap 1016 in place as shown in FIG. 10 the container wall 1006 may be deformed and/or the remote energizer 1024 may be activated without necessarily leading to emission of an IF signal; the energy needed to produce the IF signal may be diverted through the short circuit path 1018 instead. If access to the cap 1015 may be restricted by the presence of the overcap 1016 as shown, then it may be anticipated that a user seeking to dispense medication may remove the remote overcap 1016 (and thus may disable the control gate 1018) before removing the cap 1015.

Thus, a remote control gate 1018 as shown in FIG. 10 may selectively inhibit emission of the IF signal by the remote, even if stimulated (e.g., by squeezing the container 1002) in a manner as otherwise may lead to emission of an IF signal. The presence of a short-circuit path or other remote control gate 1018 thus may provide positive and negative states for the activation of the remote: if the remote control gate 1018 is in a negative state (in FIG. 10, short-circuiting the energizer 1024) then the remote may not produce an IF signal regardless of stimuli; while if the remote gate 1018 is in a positive state (the remote overcap 1016 is absent so that the remote energizer 1024 is not short-circuited) then the remote may emit an IF signal in response to events as may be associated with dispensing medication.

It is again noted that the arrangement in FIG. 10 may be understood as structurally "dumb": processing, sensing, power supplies therefor, etc. may not be required. While active sensors, processors, power supplies therefor, etc. may not necessarily be prohibited, arrangements such as a conductive path 1018 short-circuiting the energizer 1024 may be sufficient so as to inhibit operation of the remote under certain circumstances, and thus to restrict false positives. Nevertheless, while perhaps structurally "dumb", the function of such a control gate 1018 arguably may be considered as "smart".

Figure 11:
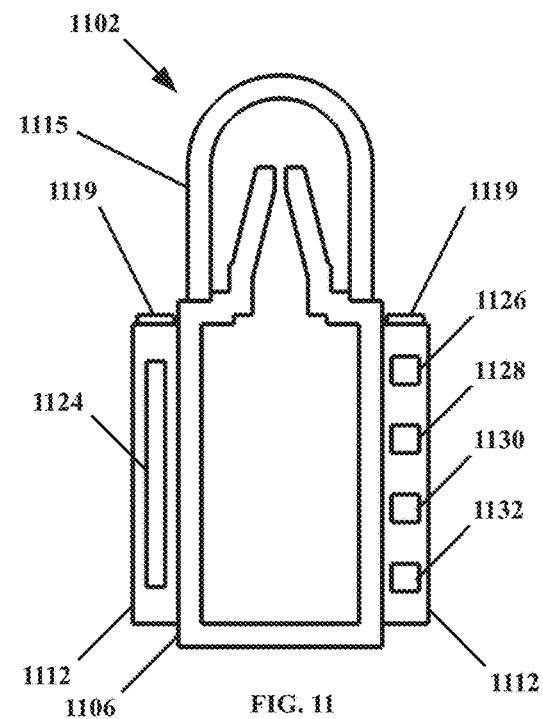

Now with reference to FIG. 11, therein an arrangement at least somewhat similar to FIG. 9 is shown: a container 1102 including a wall 1106 and a cap 1115, with a remote label 1112 engaged with the wall 1106 of the container 1102. A remote energizer 1124, a remote RF receiver 1126, a remote RFPM 1128, a remote LO generator 1130, and a remote IF emitter 1132 are disposed within the remote label 1112. Remote label contacts 1119 are present, but no remote overcap or remote short-circuit path, or remote overcap contacts are shown. The arrangement of FIG. 11 may correspond with an embodiment similar to that of FIG. 9, but wherein an overcap may have been removed prior to dispensing medication.

Figure 12:
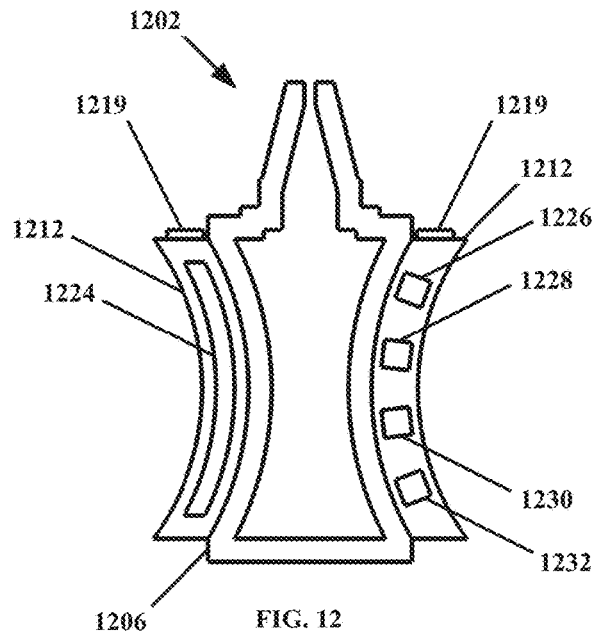

Turning to FIG. 12, a container 1202 is shown including a wall 1206, with a remote label 1212 engaged with the wall 1206 of the container 1202. A remote energizer 1224, a remote RF receiver 1226, a remote RFPM 1228, a remote LO generator 1230, and a remote IF emitter 1232 are disposed within the remote label 1212. Remote label contacts 1219 are present. No remote overcap, remote short-circuit path, or remote overcap contacts are shown; no cap also is shown to be present. In addition, the wall 1206 is deformed inward, as may be associated with dispensing medication. The arrangement of FIG. 12 may correspond with an embodiment similar to that of FIG. 11, but wherein an overcap and cap may have been removed prior to dispensing medication. Given the configuration of FIG. 12, deforming the wall 1206 thus may lead to emission of an IF signal.

Figure 13:
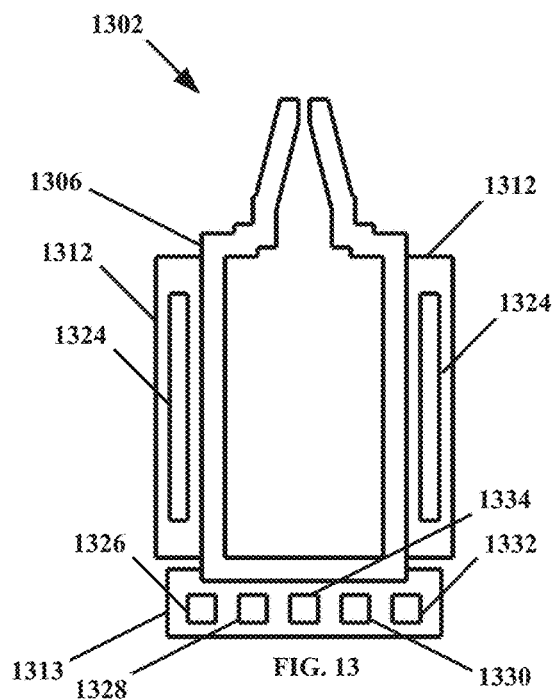
FIG. 13 depicts an example arrangement of a squeeze bottle and remote including a foot for the bottle, as may be suited for determining the use of medication through radio frequency passive modulation, in cross-section.

Turning to FIG. 13, thus example embodiments have been shown with a single energizer and all electrically driven elements disposed within a label. However, neither feature is limiting, and other arrangements may be suitable. For example, in FIG. 13 a container 1302 is shown including a wall 1306, with a remote label 1312 engaged with the wall 1306 of the container 1302. Two remote energizers 1324 are disposed in the remote label 1312. A remote RF receiver 1326, a remote RFPM 1328, a remote LO generator 1330, and a remote IF emitter 1332 are disposed within a remote shoe 1313 engaged with the foot of the container 1302 (e.g., adhered thereto with adhesive, friction fitted into place, etc.). The location, number, and/or manner of engagement of various elements of a remote are not limited, and may vary considerably.

In addition, as may be seen the remote shoe 1313 in FIG. 13 includes a remote control gate 1334 disposed therein. While certain previous examples presented a control gate in the form of a short circuit path in an overcap, embodiments are not limited to short circuits or to disposition on/in an overcap or similar structure. For example, the remote control gate 1334 may take the form of a photodiode, engaged in series with a conductive path from the remote energizers 1324. When sufficient light strikes the photodiode, the photodiode may conduct electricity therethrough from the energizers 1324 to the remote RF receiver 1326, remote RFPM 1328, remote LO generator 1330, and/or remote IF emitter 1332, while the photodiode may obstruct the flow of electricity. Such an arrangement may be suitable, for example, when the container 1302 is transparent but the remote label 1312 and cap (not shown) are opaque; thus when the cap is in place little or no light may reach the photodiode, while with the cap removed light may pass through the top of the container 1302. Thus the remote may be inhibited from sending an IF signal with the cap in place (the photodiode of the remote control gate 1334 being in a negative state, due to insufficient light), but enabled to send an IF signal with the cap removed (the remote control gate 1334 being in a positive state with adequate light). Again, such a control gate arrangement may be considered as structurally dumb, but also functionally smart.

Figure 14:
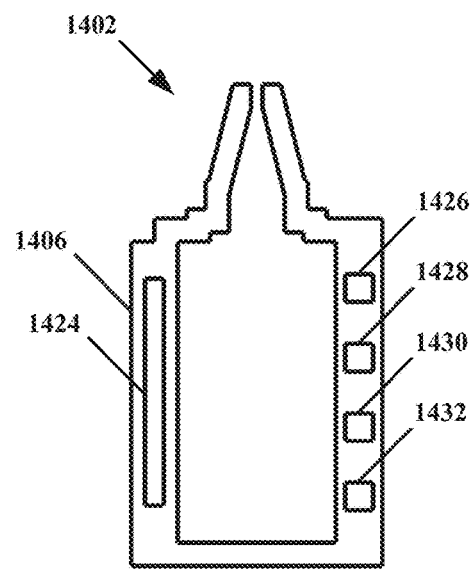
FIG. 14 depicts an example arrangement of a squeeze bottle with elements of a remote integrated into side walls thereof, as may be suited for determining the use of medication through radio frequency passive modulation, in cross-section.

Turning to FIG. 14, certain previous examples have presented arrangements wherein a remote and/or components thereof are distinct from a container. For example, a label may be applied to the wall of a container, an overcap engaged with the container over the cap therefor, a shoe applied to the foot of the container, etc. Such arrangements may be useful in at least certain instances, for example in facilitating retrofitting existing containers with functionality of remotes as described herein. However, other arrangements, including but not limited to integrating some or all elements of a remote into a container, also may be suitable.

In the arrangement of FIG. 14, a container 1402 is shown, with a container wall 1406. No label, foot, etc., is shown to be present. Rather, an energizer 1424, remote RF receiver 1426, remote RFPM 1428, remote LO generator 1430, and remote IF emitter 1432 are embedded within the container wall 1406. For example, elements 1424, 1426, 1428, 1430, and 1432 may be encapsulated while molding the container 1402 out of plastic (though other arrangements also may be suitable). Despite a different manner of engagement, the elements shown in FIG. 14 may provide similar functionality to arrangements wherein remote elements were applied with labels, etc., e.g., providing an IF signal from an RF signal and LO signal when energized as medication is dispensed.

Figure 15:
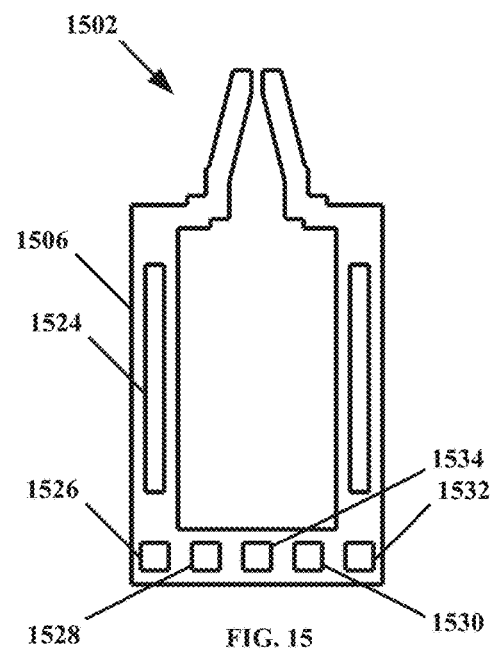
FIG. 15 depicts an example arrangement of a squeeze bottle with elements of a remote integrated into side walls and the bottom thereof, as may be suited for determining the use of medication through radio frequency passive modulation, in cross-section.

Similarly, in the arrangement of FIG. 15 a container 1502 is shown, with a container wall 1506 and two remote energizers 1524, a remote RF receiver 1526, a remote RFPM 1528, a remote LO generator 1530, and a remote IF emitter 1532 embedded within that container wall 1506. However, compared with FIG. 14 in FIG. 15 the remote RF receiver 1526, remote RFPM 1528, remote LO generator 1530, and remote IF emitter 1532 are in the bottom rather than the side of the container 1502; as noted, such configurations are not limited. A remote control gate 1534 also is shown, for example as may include a photodiode so as to enable electrical energy to flow from the remote energizers 1524 when in a positive state (adequately illuminated) but not when in a negative state (insufficiently illuminated). For an arrangement such as shown in FIG. 15, operation of such a photodiode as a remote control gate 1534 may be facilitated by a container wall 1506 that is differentially transparent, e.g., passing light through the top thereof but not the sides. Alternately, the container wall 1506 may be transparent but an opaque label overlaid thereon (not shown) so as to block light through the sides. Other arrangements also may be suitable, including control gates not including photodiodes.

Figure 16:
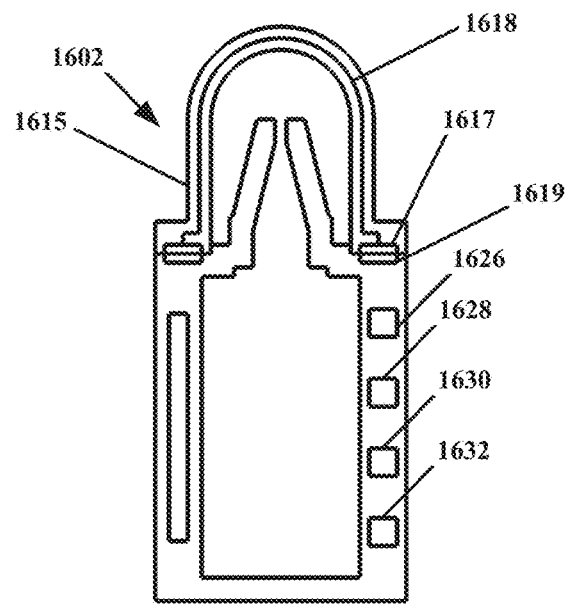
FIG. 16 depicts an example arrangement of a squeeze bottle with elements of a remote integrated therein and a short-circuit control gate integrated into a cap thereof, as may be suited for determining the use of medication through radio frequency passive modulation, in cross-section.

Now with reference to FIG. 16, another arrangement is shown wherein a remote may be integral with a container. A container 1602 is shown, having a container wall 1606 and a cap 1615. An energizer 1624, remote RF receiver 1626, remote RFPM 1628, remote LO generator 1630, and remote IF emitter 1632 are embedded within the container wall 1606. In addition, the cap 1615 includes a remote short circuit path 1618 and cap contacts 1617 embedded therein, and the container wall 1606 includes wall contacts 1619 embedded therein. The cap contacts 1617, remote short circuit path 1618, and wall contacts 1619 together may cooperate so as to short-circuit the remote energizer 1624 when the cap 1615 is in place, but not when the cap 1615 is removed. Thus the cap contacts 1617, remote short circuit path 1618, and wall contacts 1619 may cooperate to serve as a remote control gate in a manner at least somewhat similar to that of the overcap 0916 in FIG. 9, though in FIG. 16 no overcap is present and the remote short circuit path 1618 is integral with the cap 1615 and container wall 1606 instead.

Other arrangements than are shown as examples in FIG. 5 through FIG. 16 may be equally suitable. In particular, while squeeze bottles are shown for purposes of illustrations, embodiments are not limited only to squeeze bottles as containers.

In addition, in comparing certain examples wherein elements of a remote are integral to a container (e.g., FIG. 14 through FIG. 16) with other examples wherein elements of a remote are distinct from a container (e.g., FIG. 7 through FIG. 13), it may be observed that precisely what does and does not constitute a remote or part thereof may vary from one embodiment to another. For example, in the arrangement of FIG. 7, the energizer 0724, remote RF receiver 0726, remote RFPM 0728, remote LO generator 0730, and remote IF emitter 0732 are all embedded in a label 0712. It therefor may be reasonable to refer to the label 0712 as "being" the remote, and the remote as being a thing physically distinct from the container 0702.

However, in the arrangement of FIG. 14, an energizer 1424, remote RF receiver 1426, remote RFPM 1428, remote LO generator 1430, and remote IF emitter 1432 are again present, are shown in a similar position and configuration, and may function in a similar manner, yet there is no single physical entity distinct from the container 1402 as may be referred to as the remote. Functionality of a remote, and physical elements facilitating that functionality, are present in FIG. 14, but at least arguably there may be no physical difference between the remote and the container; in FIG. 14, the remote is inextricably part of the container.

Thus it should be understood that reference to "a remote" does not necessarily imply either that the remote must be or is physically distinct from an associated container, or that the remote must be or is physically integral with an associated container. So long as the functions of a remote are carried out, the physical form of that remote, and the degree to which that remote may or may not be a distinct and separate object in itself, may vary and are not limited.

Similarly, the form and/or integration of other elements also is not limited. For example, whether a control gate is physically distinct, composed of one element or several, etc., may vary from one embodiment to another. In the arrangement of FIG. 9 it may be at least arguable that the short-circuit path 0918 alone constitutes the control gate, in that the function of short-circuiting the energizer 0924 may be what either enables or disables production of an IF signal. However, it may be equally suitable to consider the contacts 0917 and/or 0919, or even the overcap 0916, as part of the control gate. Conversely, in the arrangement in FIG. 13 the control gate 1334 is illustrated as a single discrete element, e.g., a photodiode, and such an arrangement likewise may be suitable for certain embodiments. So long as the functions of a control gate (or other element) are carried out, the physical form, being distinct and/or integral, being of one part or many, etc., are not limited.

While certain previous examples have shown remotes and/or portions thereof engaged with containers, FIG. 17 through FIG. 22 collectively depict example remotes and/or portions thereof not engaged with a container, for example a label, a sleeve, etc.

Figure 17:
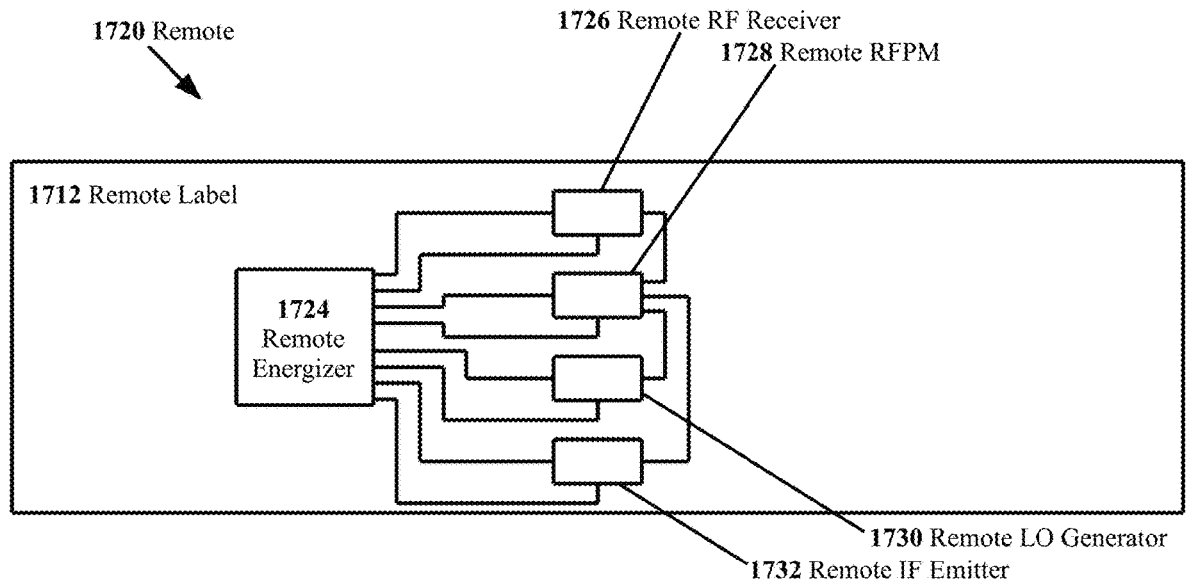
FIG. 17 depicts an example remote as may be suited for determining the use of medication through radio frequency passive modulation, in the form of a label in a flat configuration, in top-down view.

With regard specifically to FIG. 17, a remote 1720 is shown as may be engaged with a container (not shown) so as to carry out certain functions previously described herein. The remote 1720 includes a remote label 1712, for example an adhesive label as may be wrapped around and adhered to a container such as a squeeze bottle (though no such container is illustrated, and as shown the remote label 1712 is shown in a flat condition). As may be understood, the remote label 1712 may be flexible to at least some degree if the remote label 1712 is to be wrapped around a container to conform therewith, though this is not necessarily required. The remote 1724 includes a remote energizer 1724, for example a piezoelectric element, as well as a remote RF receiver 1726, a remote RFPM 1728, a remote LO generator 1730, and a remote IF emitter 1732. Each of the remote RF receiver 1726, remote RFPM 1728, remote LO generator 1730, and remote IF emitter 1732 are shown to be connected with the remote energizer 1724 via electrical traces, for example so as to draw power from the remote energizer 1724. In addition, the remote RF receiver 1726 is shown to be connected with the remote RFPM 1728, for example so as to communicate an RF signal thereto; the remote LO generator 1730 is shown to be connected with the remote RFPM 1728, for example so as to communicate an LO signal thereto; and the remote IF emitter 1732 is shown to be connected with the remote RFPM 1728, for example so that the remote RFPM 1728 may communicate an IF signal to the IF emitter 1732.

Thus, given functionality as previously described herein for certain similar elements, if the remote energizer 1724 is activated (e.g., by stressing/flexing a piezoelectric element) the remote RF receiver 1726, remote RFPM 1728, remote LO generator 1730, and remote IF emitter 1732 may cooperate to provide an IF signal. If the label 1712 were to be wrapped around a container, the IF signal then may be emitted if that container (and thus the label 1712 therewith) were squeezed so as to dispense medication therefrom.

The visibility of the remote energizer 1724, remote RF receiver 1726, remote RFPM 1728, remote LO generator 1730, remote IF emitter 1732, and traces thereamong shown in FIG. 17 is illustrative only. In practice, such elements may or may not be visible on a remote label 1712 (or other body for a remote), and when visible on a remote label 1712 may or may not be visible when the remote label 1712 is engaged with a container. For example, elements encapsulated within an opaque remote label 1712 may not be visible, while elements applied to surface of a remote label 1712 or incorporated into a transparent remote label 1712 may be visible. As another example, elements applied to an inner surface of a remote label 1712 may be visible while the remote label 1712 is laid flat, but not visible while the remote label 1712 is adhered to a container. Visibility of elements or lack of same is not limiting.

Figure 18:
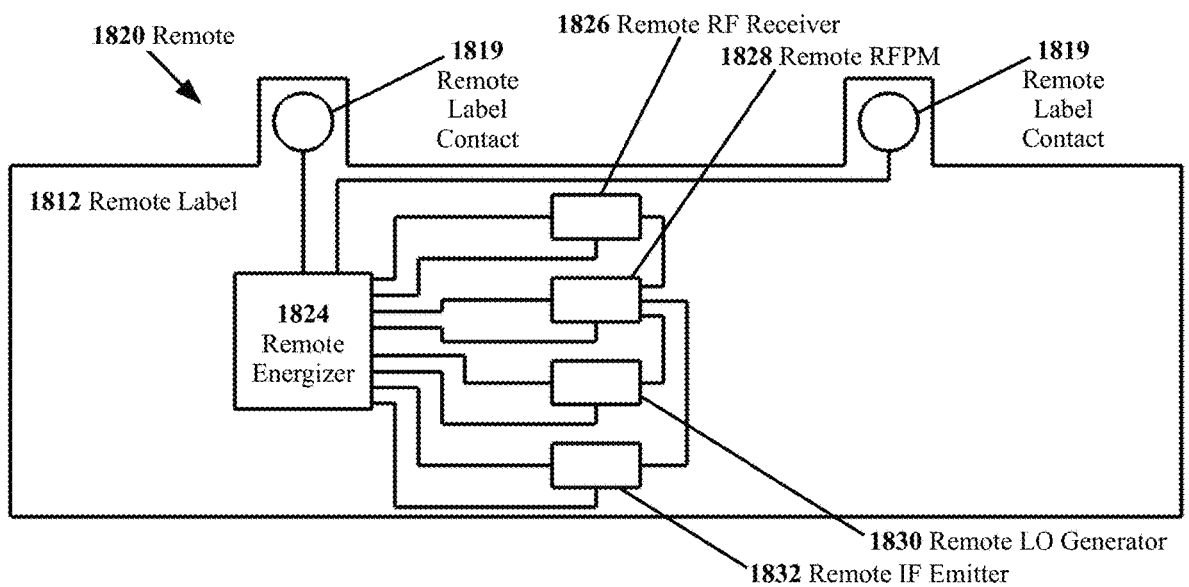
FIG. 18 depicts an example remote including contacts for a short-circuit control gate as may be suited for determining the use of medication through radio frequency passive modulation, in the form of a label in a flat configuration, in top-down view.

In FIG. 18, an arrangement at least somewhat similar to that in FIG. 17 is shown. A remote 1820 is shown with a remote label 1812, with a remote energizer 1824, remote RF receiver 1826, remote RFPM 1828, remote LO generator 1830, and remote IF emitter 1832 disposed on the remote label 1812. Traces (not individually numbered) also are shown as may for example place the remote RF receiver 1826, remote RFPM 1828, remote LO generator 1830, and remote IF emitter 1832 in electrical communication with the remote energizer 1824 and the remote RF receiver 1826, remote LO generator 1830, and remote IF emitter 1832 in data communication with the remote RFPM 1828, as described with regard to certain previous examples.

In addition, the remote label 1812 includes remote label contacts 1819, each disposed on a tab (not individually numbered) extending from the remote label 1812. With such an arrangement, the remote label contacts 1819 may be accessible, e.g., for engaging a short circuit pathway serving as a control gate, while the remote label 1812 is wrapped around a container. Traces between the remote label contacts 1819 and the remote energizer 1824 are also shown, as may place the remote label contacts 1819 in electrical communication the remote energizer 1824. Thus, if a short circuit between the two remote label contacts 1819 were established, energy from the remote energizer 1824 may short therethrough without energizing one or more of the remote RF receiver 1826, remote RFPM 1828, remote LO generator 1830, and remote IF emitter 1832. Thus, at least a portion of a control gate functionality as previously described herein may be carried out by the remote label contacts 1819 and traces, for a remote 1820 as shown in FIG. 18.

Figure 19:
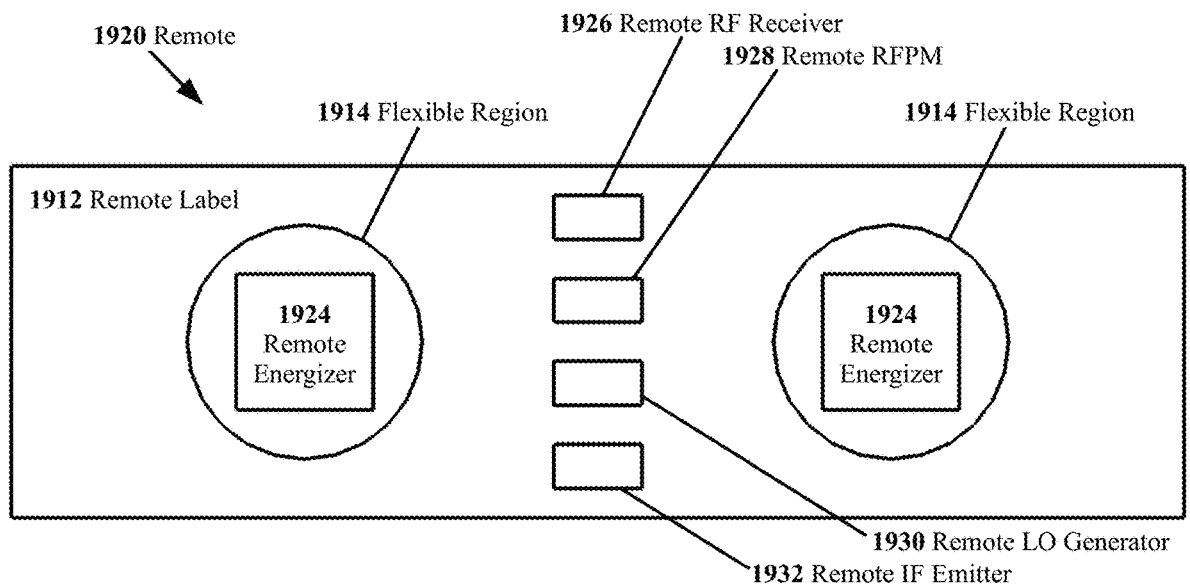
FIG. 19 depicts an example remote as may be suited for determining the use of medication through radio frequency passive modulation, in the form of a label with flexible regions therein in a flat configuration, in top-down view.

Now with reference to FIG. 19, a remote 1920 is shown with a remote label 1912, with two remote energizers 1924, a remote RF receiver 1926, a remote RFPM 1928, a remote LO generator 1930, and a remote IF emitter 1932 disposed on the remote label 1912. (Traces placing such elements in communication may be present, but are not explicitly shown for simplicity.) As previously noted, certain embodiments such that shown in as FIG. 17 a remote label 1712 may be presumed to be at least somewhat flexible so as to facilitate engaging that remote label 1712 with a container. However, it is not required that a given label be flexible to any particular degree (if at all); thus for certain embodiments such as shown in FIG. 19, the remote label 1912 may be rigid or at least semi-rigid. To facilitate manipulation of the remote energizers 1924, flexible regions 1914 may be provided in proximity to the remote energizers 1924. Even if the remote label 1912 overall may not be sufficiently flexible to enable activating a piezoelectric element (or other remote energizer 1924), the flexible regions 1914 may facilitate sufficient flexing. Thus, while it may be suitable in certain embodiments for an entire label to be flexible, in other embodiments only some portion of a label may be flexible. (Moreover, flexing an energizer may not be required for all embodiments; in such instance a label or other body may not be required to be flexible even in part.)

Figure 20:
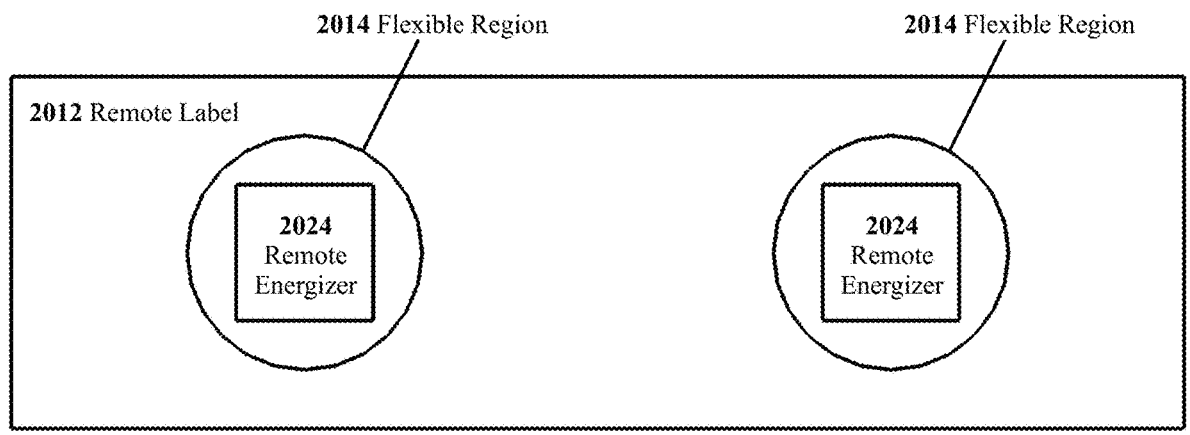
FIG. 20 depicts a portion of an example remote as may be suited for determining the use of medication through radio frequency passive modulation, in the form of a label with flexible regions therein in a flat configuration, in top-down view.

Now with reference to FIG. 20, as noted previously (for example with regard to FIG. 13), even in embodiments wherein certain elements may be disposed on a label or other body, not all elements may be required to be disposed on a body (or on the same body). FIG. 20 shows a remote label 2012 as may serve as a portion of a remote. The remote label 2012 defines flexible regions 2014 therein, and two remote energizers 2024 are disposed within those flexible regions 2014. However, it is noted that no remote RF receiver 2026, remote RFPM 2028, remote LO generator 2030, or remote IF emitter 2032 are visible in FIG. 20, nor any elements adapted to provide equivalent or similar functionality (as may be equally suitable). However, as shown in FIG. 13, certain elements may for example be disposed in a foot, or otherwise disposed elsewhere than in/on a label. While disposing elements in/on a label may be useful for at least certain embodiments, other arrangements may be suitable and embodiments are not limited only thereto.

Figure 21:
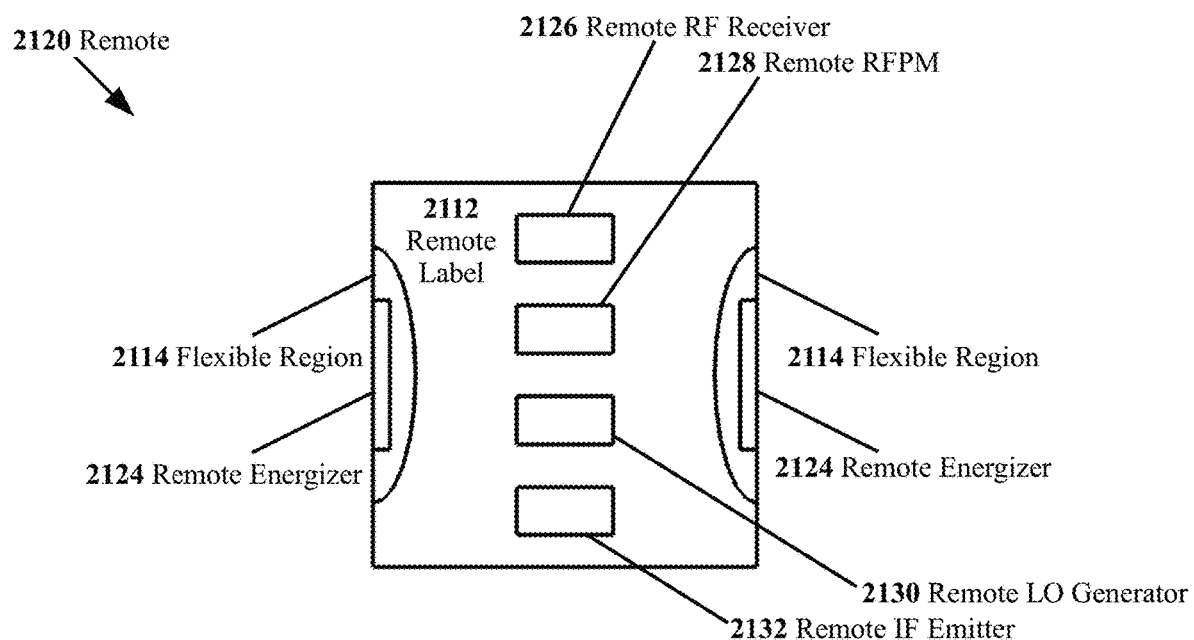
FIG. 21 depicts an example remote as may be suited for determining the use of medication through radio frequency passive modulation, in the form of a label in a wrapped configuration, in side view.

Moving on to FIG. 21, therein an arrangement as may be at least somewhat similar to that in FIG. 19 is shown, though not necessarily identical and in different view. In FIG. 21 a remote 2120 is shown, having a remote label 2112 defining two flexible regions 2114 with a remote energizer 2124 disposed on each such flexible region 2114. A remote RF receiver 2126, remote RFPM 2128, remote LO generator 2130, and remote IF emitter 2132 are shown disposed on the remote label 2112 as well. However, where in FIG. 19 the label therein was viewed laid flat, in FIG. 21 the remote label 2112 is wrapped into a cylindrical form, as may be the case if that remote label 2112 were wrapped around a container (not shown). As may be seen, in such configuration the remote energizers 2124 are on opposing sides of the cylinder, in such position that the remote energizers 2124 may be stressed and/or distorted if such a container were deformed, e.g., a finger on one remote energizer 2124 and a thumb opposite on the other remote energizers 2124 (though this is not limiting).

Figure 22:
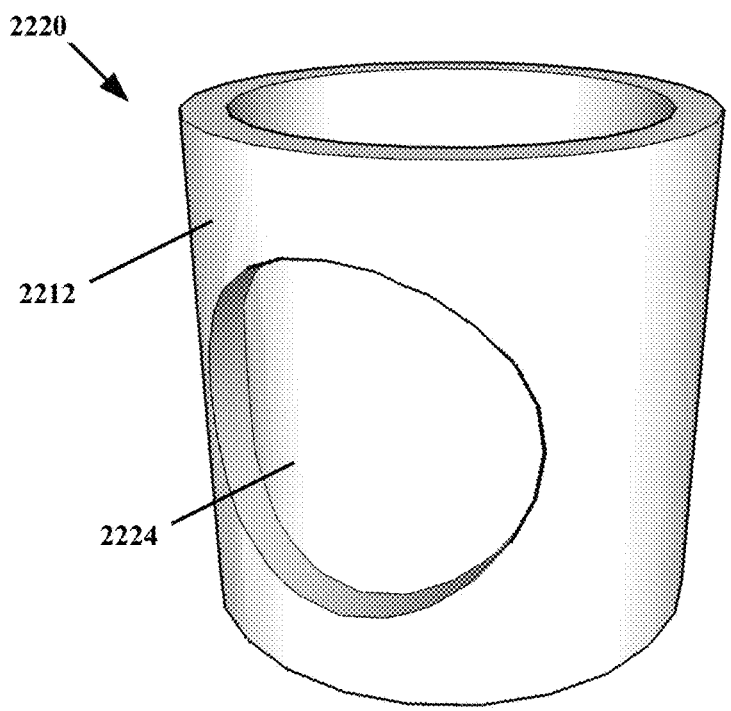
FIG. 22 depicts an example remote as may be suited for determining the use of medication through radio frequency passive modulation, in the form of a sleeve for a container, in perspective view.

Turning to FIG. 22, as noted it is not required for an entire label to be flexible, nor even for a remote to utilize a label. In FIG. 22, a remote 2220 is shown that may bear at least some visual resemblance to FIG. 21. However, in FIG. 22 no label is present, rather a cylindrical remote sleeve 2212 is visible with a flexible region 2224 defined therein, e.g., in the form of a cut-out through the remote sleeve 2212 and a flexible substrate covering that cut-out. One or more additional cut-outs and substrates may be present elsewhere on the remote sleeve 2212, though not visible in the perspective view shown. Likewise, as FIG. 22 is a perspective view, internal elements of the remote 2220 are not explicitly illustrated (and indeed may not be visible in practice). However, as may be understood from certain previous examples, an energizer may be disposed behind the substrate, a remote RF receiver, a remote RFPM, a remote LO generator, and a remote IF emitter (or elements facilitating similar functionality) may be present on the inner surface of or enclosed within the remote sleeve 2212, etc.

In addition to illustrating another possible embodiment exhibiting at least partially rigid structure as opposed to a flexible label, an arrangement such as is shown in FIG. 22 may exhibit certain advantages. For example, typically an adhesive label may be readily engaged with a bottle as a manufacturing operation, e.g., using automated equipment to place and wrap the label around a container, etc. However, applying such a label to a container on a small or individual bottle scale may be problematic for individual patients, pharmacists, clinical study technicians, etc. Thus, while a remote in the form of a label may be convenient for retrofitting existing containers to function as described herein at a point of manufacture or in similar conditions, labels may be a less efficient form for so retrofitting containers as piece-work, etc. However, a remote sleeve 2212 such as is shown in FIG. 22 may be readily engaged with an existing container, e.g., the container may be "just slipped into" the sleeve. In addition, a remote sleeve 2212 may prove more suited for reuse, e.g., being applied to a container, then removed and applied to a new container when the first container is empty. While certain labels may at least in principle be considered reusable, a sleeve 2212 may in at least some embodiments prove more durable, more convenient to reuse, etc.

Now with regard to FIG. 23 through FIG. 28, therein example functional schematics are presented so as to illustrate operation of various embodiments (though not necessarily all possible embodiments) of base and/or remote. Where for example FIG. 22 may reflect the actual physical appearance of a remote (though not all remotes necessarily will resemble that in FIG. 22), in FIG. 23 through FIG. 28 various arrangements of elements for bases and/or remotes are shown with regard to presence, communication, function, etc., including with regard to signals as may enter and leave a given base and/or remote.

Figure 23:
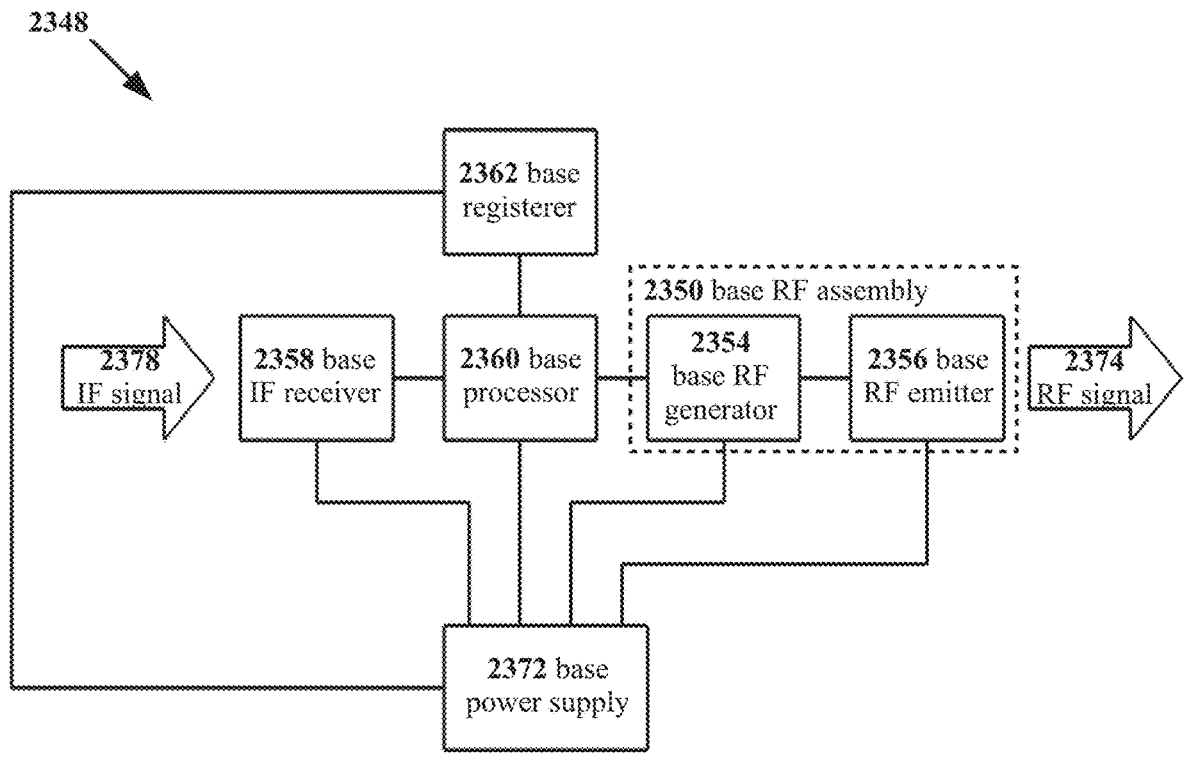
FIG. 23 depicts an example base as may be suited for determining the use of medication through radio frequency passive modulation, with use of a dedicated RF signal, in schematic view.

In FIG. 23, a schematic representation of an example base 2348 is depicted. The arrangement as shown is configured for use of a dedicated RF signal, as has been previously explained herein. The base 2348 includes a base processor 2360, and a base power supply 2372 in communication with the base processor 2360 such that the base processor 2360 may draw power from the base power supply 2372, and/or control the base power supply 2372. The base 2348 also includes a base IF receiver 2358, a base registerer 2362, and a base RF assembly 2350 that in turn includes a base RF generator 2354 and a base RF emitter 2354. Each of the base IF receiver 2358, the base registerer 2362, base RF generator 2354, and base RF emitter 2354 is in communication with the base power supply 2372 so as to draw power therefrom. In addition, the base processor 2360 is in communication with the base IF receiver 2358, base RF generator 2354, and base registerer 2362 so as to communicate information thereamong. The base processor 2360 also is in communication with the base RF generator 2356 so as to communicate information therebetween.

Such an arrangement for a base as shown in FIG. 23 may support certain functions as previously described herein. For example, the base processor 2360 may be adapted to communicate with the base RF generator 2354 and/or the base RF emitter 2356 (and/or to the base RF assembly 2350 collectively) so as to facilitate the base generator 2354 in generating a characteristic RF signal, the base generator 2354 communicating that RF signal to the base RF emitter 2356, and/or the base RF emitter 2356 in wirelessly emitting the RF signal 2374 from the base 2348 as a whole. (It is noted that the RF signal 2374 and also the IF signal 2378 are shown only once, in arrows to indicate whether the signals are being sent or received; in practice such signals also may be communicated e.g. via wires among various elements shown in FIG. 23, but such communication may vary considerably and is not illustrated exhaustively for purposes of simplicity.) Likewise, the base processor 2360 may be adapted to communicate with the base IF receiver 2358 so as to facilitate the base IF receiver 2358 in receiving the IF signal 2378 into the base, to compare that IF signal to an IF signal standard, to certify that IF signal, and/or to facilitate the base registerer 2362 in registering a medication-associated event.

The base processor 2360 is not limited in terms of structure, specifics of operation, etc. Typically, though not necessarily, a processor 2360 may be adapted to carry out executable instructions instantiated thereon, and/or to carry out certain functions for a base 2348 through execution of those instructions. Suitable processors 2360 may include but are not limited to digital electronic microprocessors, for example as may be present in smart phones, laptop computers, desktop computers, tablets, smart watches, HMDs, etc. In addition, it is noted that a processor 2360 may not be required for all embodiments. While a processor 2360 may facilitate certain functions in some embodiments, such as comparing an incoming IF signal to an IF signal standard, other arrangements may be equally suitable. For example, a hard-wired system adapted to carry out such comparison with no processing per se and/or no executable instructions thereon may be suitable for certain embodiments. So long as functions of a base as described herein are carried out, the form and particulars, including the presence and/or absence of a processor 2360 (or other elements), are not limiting.

Base RF generators 2354 also may vary considerably. Typically, though not necessarily, a base RF generator 2354 may be a solid-state electronic signal generator adapted to configure a suitable characteristic RF signal for functions as described herein. Alternately, a base RF generator 2354 may be incorporated in and/or indistinguishable from a base processor 2360, e.g., the RF signal may be configured by a processor 2360 via executable instructions rather than configured in a separate RF generator 2354.

Base IF receivers 2358 and base RF emitters 2356 similarly may vary among embodiments. Suitable base IF receivers 2358 and base RF emitters 2356 may include but are not limited to receiving and/or broadcasting communicators for signals in radio bands, such as AM/FM, Wi-Fi®, BLUETOOTH®, etc. In certain embodiments the base IF receiver 2358 and base RF emitter 2356 may be combined into a single device adapted both to transmit and to receive suitable signals. However, while permitted such combination of elements is not required.

Similarly, the base RF generator 2354 and base RF emitter 2356 may be, but are not required to be, combined physically, logically, and/or otherwise into a base RF assembly 2350. Certain embodiments may include a combined base RF assembly 2350, while others may include a distinct base RF generator 2354 and base RF emitter 2356, and/or may define such elements in different ways for logical/functional purposes, etc. Embodiments are not limited with regard to whether a base RF assembly 2350, base RF generator 2354 and base RF emitter 2356, or some other functionally similar arrangement is present.

The base registerer 2362 also may vary from one embodiment to another. The base registerer is adapted to register events and/or associated information, including but not limited to the event of dispensing a medication, the time at which that medication was dispensed, the location, the identity of the medication, container, person dispensing, person using, person prescribing, etc. The base registerer 2362 is not limited in what information may be registered, nor is the base registerer limited with regard to how or in what form such information is registered. For example, a base registerer 2362 may include a digital data store (such as flash memory, a hard drive, etc.) adapted to record information in digital form, a graphical display (such as a touch screen, LCD, LED, electronic paper, telltale light, etc.) adapted to present information visibly, an audio output (such as a speaker) adapted to present information audibly, a communicator (such as a modem, cell phone system, Wi-Fi® link, etc.) adapted to deliver information to some remote location, system, and/or person, etc. Other arrangements may also be suitable. In addition, it is noted that the base registerer 2362 may not necessarily be a unique device, for example a base registerer 2362 adapted to communicate a dispensing event to a clinical trial database may be the same physical device as a base IF receiver 2358 and/or base RF emitter 2356.

Still with reference to FIG. 23, while all elements therein are illustrated together and linked (e.g., by wires), such an arrangement is not required. Certain elements may be in one physical device and/or one physical location, while other elements are in a different device and/or location. Also, not all elements necessarily even will be physical, for example the base processor 2360 (if present) may have no well-defined physical substance as such, with the functions thereof being carried out through cloud computing instead. Embodiments are not limited with regard to physical structure, so long as the functions described herein are enabled.

Figure 24:
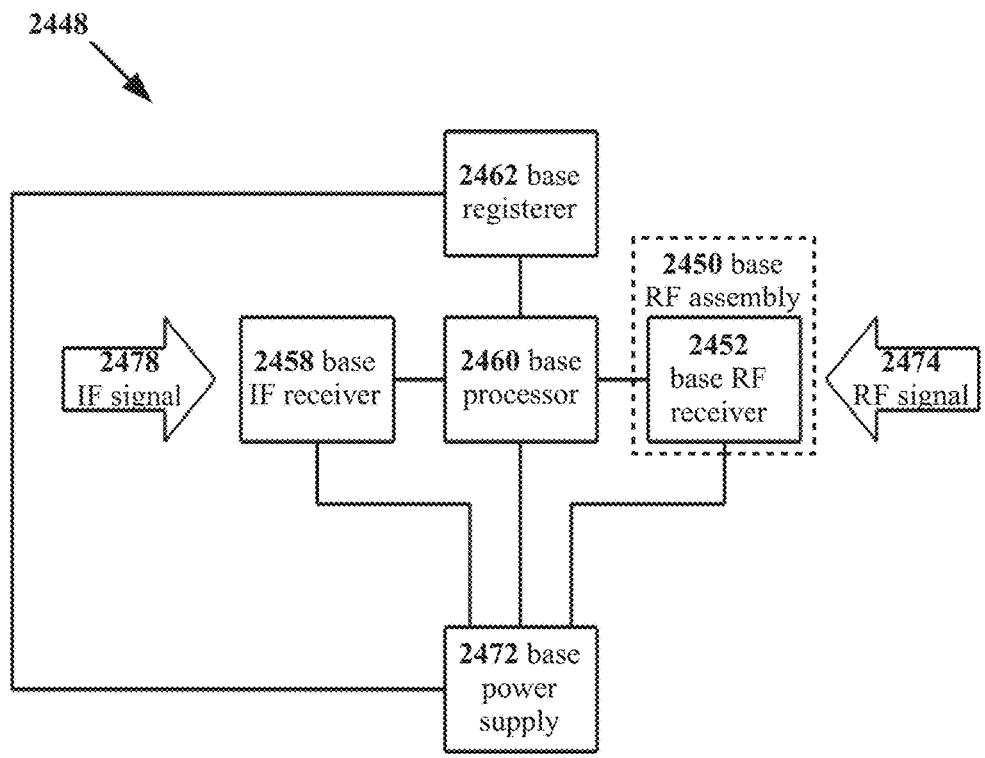
FIG. 24 depicts an example base as may be suited for determining the use of medication through radio frequency passive modulation, with use of an ambient RF signal, in schematic view.

Now with reference to FIG. 24, therein another embodiment of a base 2448 is shown. The base 2448 may be in some ways similar to that in FIG. 23, with the base 2448 in FIG. 24 including a base processor 2460, base power supply 2472, base IF receiver 2458, base register 2462, and base RF assembly 2450, shown in communication with one another. However, in the arrangement of FIG. 24 the base RF assembly 2452 includes a base RF receiver 2452 adapted to receive an RF signal 2474 therein (rather than a base RF generator and base RF emitter adapted to produce an RF signal). Thus the arrangement shown in FIG. 24 may be understood as adapted to function with ambient RF signals, rather than necessarily using a dedicated RF signa, as described previously herein. Where the arrangement in FIG. 23 produces an RF signal and takes in an IF signal, the arrangement in FIG. 24 instead takes in an existing RF signal 2474 and also takes in an IF signal 2478 (e.g., as may be generated by a remote, not shown in FIG. 24). Thus, the base 2448 as shown may not require any capability to transmit signals, so long as incoming signals may be received (although the ability to transmit signals is not prohibited).

Figure 25:
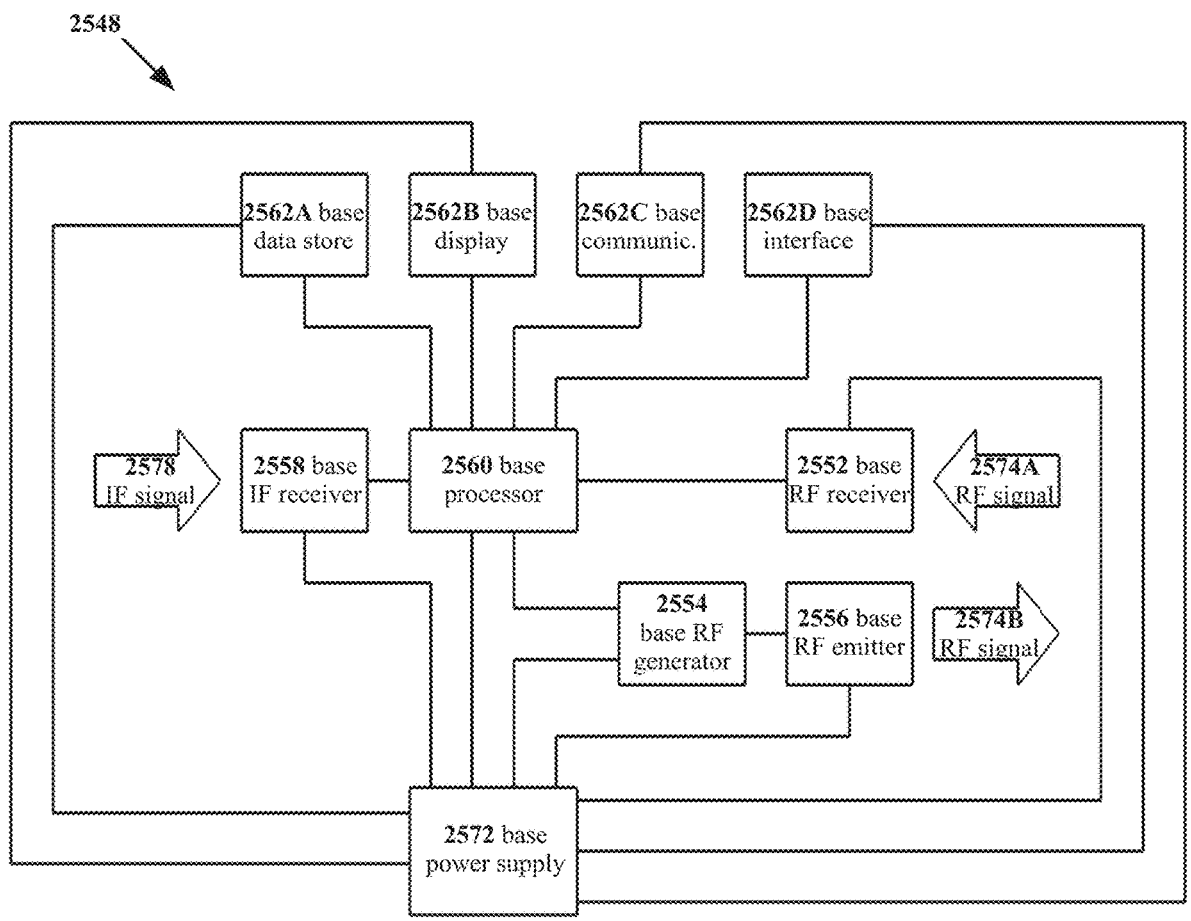
FIG. 25 depicts an example base as may be suited for determining the use of medication through radio frequency passive modulation, with use of either a dedicated RF signal or an ambient RF signal, in schematic view.

Turning to FIG. 25, another embodiment of a base 2548 is illustrated therein. The base 2548 may in some ways resemble the arrangements in FIG. 23 and/or FIG. 24, including a base processor 2560, base power supply 2572, and base IF receiver 2558. The base 2548 also includes a base RF receiver 2552, a base RF generator 2554, and a base RF emitter 2556; however, while similar elements have been described with regard to FIG. 23 and FIG. 24, neither previous arrangement included both a base RF receiver 2552 adapted to receive an ambient RF signal 2574A and a base RF emitter 2556 adapted to transmit a dedicated RF signal 2574B. The arrangement in FIG. 25 thus may be adapted either to operate using a dedicated RF signal 2574B as sent out (e.g., so as to be received by a remote and modulated into an IF signal), or to operate using an ambient RF signal 2574A as picked up from an environment (and potentially picked up also by a remote and modulated into an IF signal), or to do both, or to alternate between options. For example, a base 2548 as shown may be adapted to utilize a suitable ambient RF signal 2574A when available (e.g., so as not to use power generating a dedicated signal), but to generate a dedicate ambient RF signal 2574B if no suitable ambient signal is available. (No base RF assembly is shown, though it may be suitable for example to logically group together the base receiver 2552, base RF generator 2554, and/or base RF emitter 2556 and refer to the combination as a base RF assembly.)

In addition, the base 2548 includes several elements as may be considered a base registerer collectively (or individually): a base data store 2562A, a base display 2562B, a base communicator 2562C, and a base interface 2562D; each such element may be adapted to carry out a function of registering a medication-associated event (and/or other information), in various manners. For example, the base data store 2562A may register information by recording that information, the base display 2562B may register information by showing that information on a graphical screen, and a base communicator 2562C may register information by sending that information to a medical professional for review. In addition, the base interface 2562D also may register information, for example in accepting feedback regarding dispensing medication from a user.

As may be understood, the information registered by the various registerers 2562A, 2562B, 2562C, and 2562D may not necessarily be identical. For example, detailed data regarding the type of medication, dispensing pharmacy, prescribing physician, etc., may be recorded by a base data store 2562A for a given dispensing event. However, a base display 2562B in the same base 2548 and for the same event may display only a simple user message such as "medication taken at 2:03 PM"; the base display 2562B may present additional information not recorded by the data store 2562A, such as "next dose at 8:00 PM" or "4 days of medication remaining". Similarly, a base interface 2562D may accept feedback from the user, such as responses to questions (possibly presented on the base display 2562B) such as "any side effects?" or "please rate the ergonomics of this clinical test container on a scale of 1 through 5".

With regard to FIG. 23 through FIG. 25 collectively, it is noted that bases may take many physical forms. For example, a base may be dedicated for use as a base or multi-purpose and adapted to carry out other functions, may be readily portable or stationary, may be of many sizes, shapes, configurations, etc. Physical form is not limiting, and may vary greatly.

Figure 26:
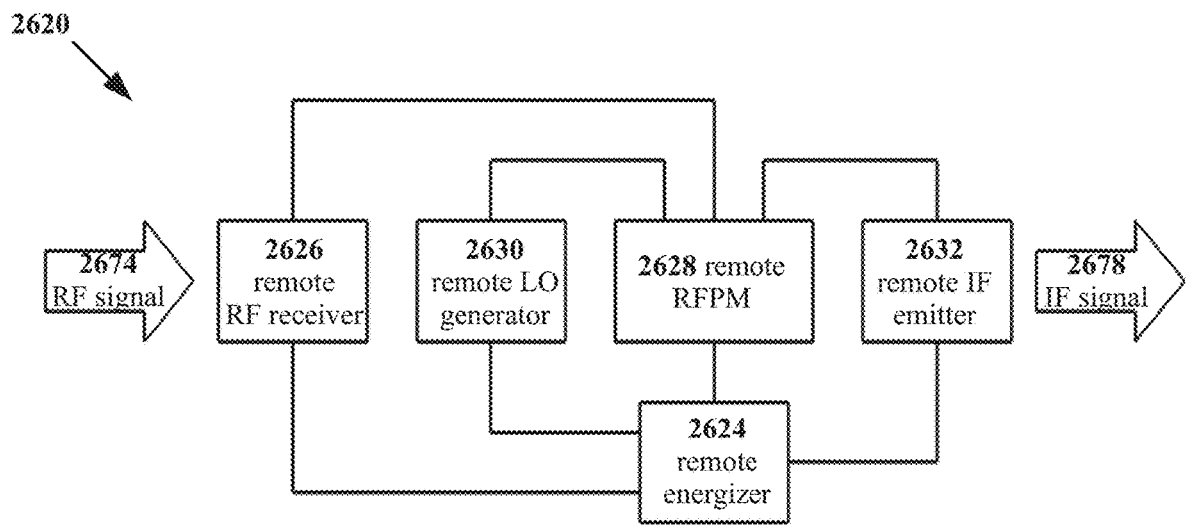
FIG. 26 depicts an example remote as may be suited for determining the use of medication through radio frequency passive modulation, with use of a dedicated RF signal, in schematic view.
Figure 27:
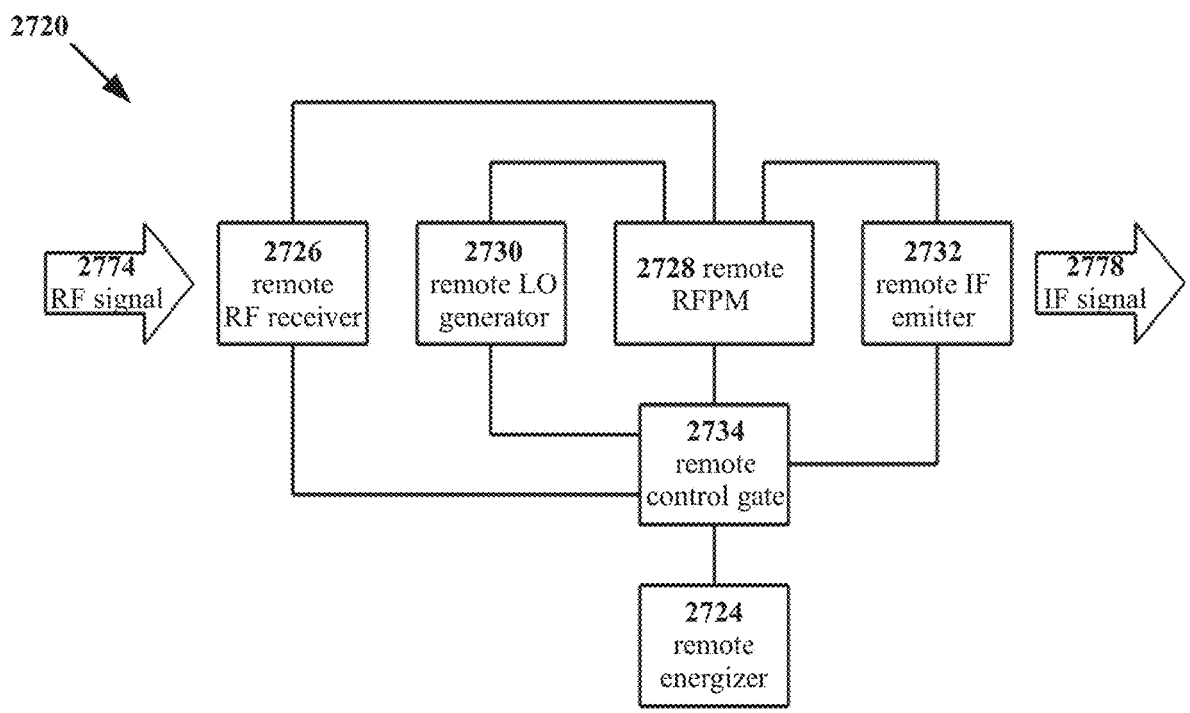
FIG. 27 depicts an example remote as may be suited for determining the use of medication through radio frequency passive modulation, with use of an ambient RF signal, in schematic view.
Figure 28:
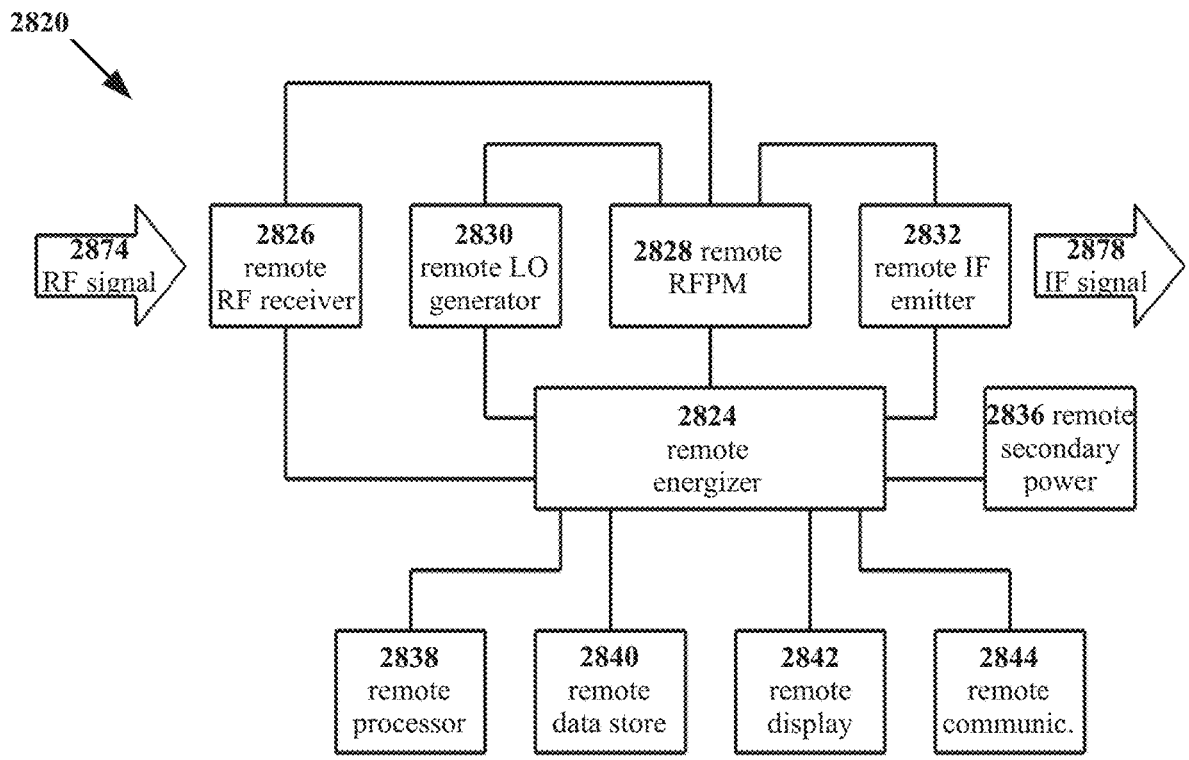
FIG. 28 depicts an example remote as may be suited for determining the use of medication through radio frequency passive modulation, with use of either a dedicated RF signal or an ambient RF signal, in schematic view.

Now with reference to FIG. 26 through FIG. 28 collectively, therein several example arrangements for a remote are illustrated, in schematic form. As noted with regard to bases in FIG. 23 through FIG. 25, internal signals are not illustrated for remotes in FIG. 26 through FIG. 28. In addition, it is noted that certain base examples presented previously herein may be specific to operating with either a dedicated incoming RF signal or an ambient incoming RF signal. Embodiments of remotes also may be possible wherein only a dedicate or only an RF signal is accepted and utilized therein. However, such a distinction may not be significant in terms of functional description; that is, a schematic as in FIG. 26 may look similar or identical regardless of whether the RF signal is ambient or dedicated (e.g., generated by a base). Thus, no attempt is made to illustrate such non-visibly distinct variations herein. However, this should not be understood as limiting what forms of RF signal(s) may be usable (or may not be usable) for various embodiments of remote.

With regard specifically to FIG. 26, a schematic representation of an example remote 2620 is shown. The remote 2620 includes a remote RF receiver 2626 as may be adapted to receive (e.g., wirelessly) an RF signal 2674 (whether dedicated or ambient) incoming to the remote 2620, a remote LO generator 2630 as may be adapted to generate an LO signal, a remote RFPM 2628 as may be adapted to mix/modulate the RF signal and LO signal so as to produce an IF signal, and a remote IF emitter 2632 as may be adapted to emit the IF signal 2678 (e.g., wirelessly) from the remote 2620.

The remote 2620 also includes a remote energizer 2624, as may be adapted to energize one or more of the remote RF receiver 2626, remote LO generator 2630, remote RFPM 2628, and remote IF emitter 2632 if/when initiated (e.g., by an initiator, not shown in FIG. 26). As may be seen, the remote RF receiver 2626, remote LO generator 2630, remote RFPM 2628, and remote IF emitter 2632 are shown to be in communication with the remote energizer 2624 so as to facilitate the remote energizer 2624 in providing energy thereto. When energized, the remote RF receiver 2626, remote LO generator 2630, remote RFPM 2628, and remote IF emitter 2632 may perform functions as described previously herein, such that the remote 2620 overall provides a detectable and characteristic IF signal as may be considered an indication that a medication-associated event (e.g., dispensing medication) may have taken place.

Similarly, the remote RF receiver 2626 and remote LO generator 2630 are in shown to be communication with the remote RFPM 2628 so as to facilitate providing the RF signal and LO signal to the remote RFPM 2628. The remote IF emitter 2632 also is shown to be in shown to be communication with the remote RFPM 2628 so as to facilitate the remote RFPM 2628 providing the IF signal to the remote IF emitter 2632. In practice, the RFPM may include dedicated ports, connection points, etc., for accepting RF and LO signals therein and/or for delivering an IF signal therefrom, though this is not required.

Various forms of remote RF receiver 2626, remote LO generator 2630, remote RFPM 2628, remote IF emitter 2632, and remote energizer 2624 may perform functions as described previously herein, such that the remote 2620 overall provides a detectable and characteristic IF signal as may be considered an indication that a medication-associated event (e.g., dispensing medication) may have taken place.

Similarly, the remote RF receiver 2626 and remote LO generator 2630 are in shown to be communication with the remote RFPM 2628 so as to facilitate providing the RF signal and LO signal to the remote RFPM 2628. The remote IF emitter 2632 also is shown to be in shown to be communication with the remote RFPM 2628 so as to facilitate the remote RFPM 2628 providing the IF signal to the remote IF emitter 2632. In practice, the RFPM may include dedicated ports, connection points, etc., for accepting RF and LO signals therein and/or for delivering an IF signal therefrom, though this is not required.

Turning to FIG. 27, another example remote 2720 is shown in schematic form, with a remote RF receiver 2726, a remote LO generator 2730, a remote RFPM 2728, a remote IF emitter 2732, and a remote energizer 2724, in communication so as to facilitate certain functions of a remote 2720 as have been previously described herein. The arrangement in FIG. 27 may be at least somewhat similar to that in FIG. 26.

However, in the example arrangement of FIG. 27 a remote control gate 2734 also is present. The remote control gate 2734 is in communication with the remote energizer 2724, and also is in communication with the remote RF receiver 2726, remote LO generator 2630, remote RFPM 2728, and remote IF emitter 2732. As shown with regard to connections thereamong, the remote control gate 2734 may be understood as being intermediary between the remote energizer 2724 and the remote RF receiver 2726, remote LO generator 2630, remote RFPM 2728, and remote IF emitter 2732. Thus, the remote control gate 2734 may be adapted to either enable or disable energy from the remote energizer 2724 from reaching one or more of the remote RF receiver 2726, remote LO generator 2630, remote RFPM 2728, and remote IF emitter 2732. Thus, the state of the remote control gate 2734 may determine whether an IF signal 2778 can or will be produced by the remote 2720, even if all other necessary conditions (e.g., the remote energizer 2724 being energized, the RF signal 2774 being received, etc.) are met. As previously noted, a remote control gate 2734 may vary considerably in form, and may include but is not limited to short circuit paths, photo-diodes, etc.

Moving on to FIG. 28, as may be seen neither FIG. 26 nor FIG. 27 show a processor or power supply as being present therein. As has been described, such elements may not be required. For example, if energy to produce and emit an IF signal is provided by an energizer, that energizer being activated upon an event associated with dispensing medication, then it may be sufficient for the IF signal to be emitted when medication is dispensed; a continuous supply of power may not be required. Likewise, a processor, sensors, etc. may not be required for operation of a remote as shown and described herein.

However, while such elements may not be required, neither are such elements (and/or others) necessarily prohibited. For example, the arrangement in FIG. 28 shows a remote 2820 with a remote RF receiver 2826, a remote LO generator 2830, a remote RFPM 2828, a remote IF emitter 2832, and a remote energizer 2824, so as to receive an incoming RF signal 2874 and emit an IF signal 2878, at least somewhat similarly to the arrangement in FIG. 26. However, the arrangement in FIG. 28 also includes various additional elements.

For example, a remote secondary power supply 2836 may be present, as may provide ongoing power to the remote 2820 and/or elements thereof, whether or not the remote energizer 2824 is energized. (As shown the remote secondary power supply 2836 is in communication with the remote energizer 2824, for example as may energize the remote energizer 2824 regardless of whether an initiator is activated. However other arrangements also may be suitable.) The remote 2820 as shown also includes a remote processor 2838 as may execute instructions instantiated thereon, a remote data store 2840 as may store data and/or instructions, a remote display 2842 as may present information (e.g., to a user via a graphical screen, microphone, etc.), and a remote communicator 2844 as may communicate information to some target external to the remote, including but not limited to the base, some third party, etc. A wide range of additional elements not explicitly shown also may be present in various embodiments, in addition to or in place of elements shown in FIG. 28. For example such additional elements may include, but are not limited to, a user interface, sensors (e.g., for gathering data on the user, the condition of the remote, whether an event associated with taking a medication is occurring, etc.), and so forth. So long as the functions necessary to the operation of the remote 2820 may be carried out, the presence and/or absence of additional elements is not limited.

Figure 29:
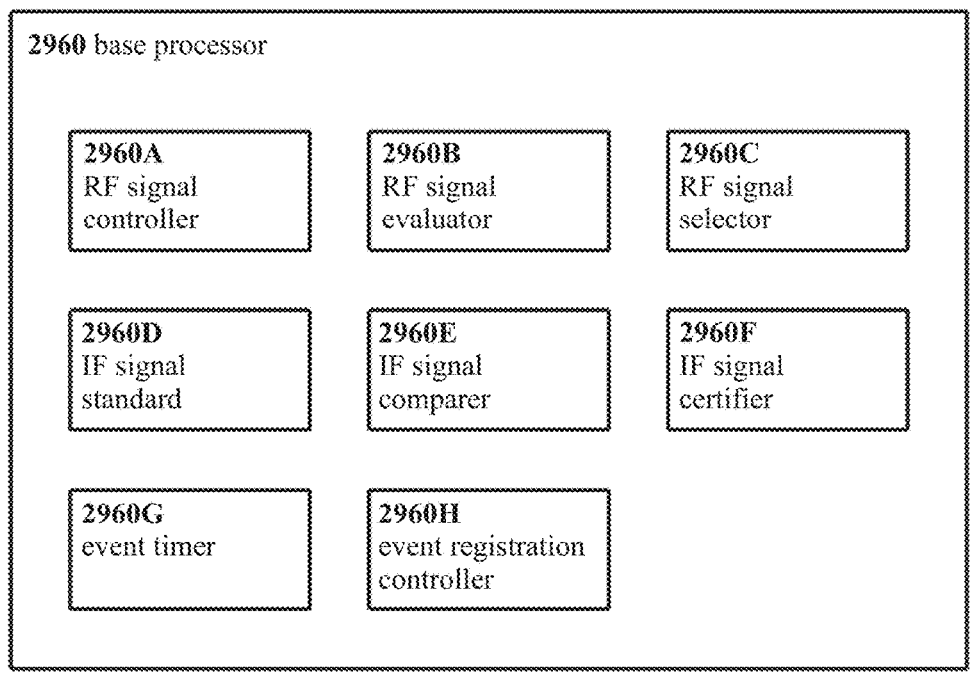
FIG. 29 depicts an example processor for a base as may be suited for determining the use of medication through radio frequency passive modulation, in schematic view.

Now with reference to FIG. 29, as noted previously (e.g., with regard to the base processor 2360 in FIG. 23) certain functions as may be carried out by a base may be implemented at least in part through the use of executable instructions instantiated on a processor. FIG. 29 shows an example arrangement of a base processor 2960 with several functional blocks of executable instructions 2960A, 2960B, 2960C, 2960D, 2960E, 2960F, 2960G, and 2960I disposed on the processor 2960.

More particularly, the RF signal controller 2960A may be adapted to configure and/or otherwise specify a dedicated RF signal as may be emitted, for example with regard to frequency, waveform, etc. The RF signal evaluator 2960B may be adapted to evaluate whether an ambient RF signal available to a base may be suitable for use by a remote as an RF signal input thereto. The RF signal selector 2960C may be adapted to select whether a dedicated RF signal will be provided (e.g., as configured by the RF signal controller 2960A) or an ambient RF signal will be utilized (e.g., as evaluated by the RF signal evaluator 2960C). The IF signal standard 2960D may be adapted to serve as a guide as to the properties expected of an incoming IF signal from a remote. The IF signal comparer 2960E may be adapted to compare one or more incoming signals to the IF signal standard 2960D so as to determine whether a candidate signal is (or at least is likely to be) an IF signal as provided by a remote. The IF signal certifier 2960F may be adapted to certify that an incoming signal is indeed an IF signal as generated by a remote, such that it may be considered that an event associated with a medication has taken place by virtue of that IF signal being received. The event timer 2960G may be adapted to determine a time at which an IF signal was received. The event registration controller 2960H may be adapted to record the event (and/or other information such as the event time) in a data store, present the event on a display, communicate the event to some external entity, or otherwise register or control the registering of the medication-associated event.

The arrangement of executable instruction blocks 2960A, 2960B, 2960C, 2960D, 2960E, 2960F, 2960G, and 2960I is not limiting; other instructions may be present in, and/or instructions shown may be absent from, various embodiments. For example, an embodiment that utilizes dedicated RF signals only may not include RF signal evaluator 2960B or an RF signal selector 2960C Likewise, while instructions are shown in instruction blocks 2960A, 2960B, 2960C, 2960D, 2960E, 2960F, 2960G, and 2960I, this is illustrative only; in practice executable instructions may be combined together, subdivided, etc.

Now with reference to FIG. 30A through FIG. 30D collectively, a sequence of events are shown as may represent cooperation of a remote and a base so as to determine a use of medication through radio frequency passive modulation.

With reference now collectively to FIG. 30A through FIG. 30D, aspects of structure and function an example arrangement for determining the dispensing and/or use of a medication through radio frequency passive modulation are shown. As illustrated, a remote and a base may cooperate in such determinations. The base may be adapted to provide a suitable RF signal, and the remote to return an IF signal characteristic of that RF signal (and/or characteristic of the remote as well). The base may then receive the IF signal, and registers a medication-associated event as having taken place based on that IF signal. The remote may be inert (or nearly so) when not actively operating so as to produce the IF signal.

Figure 30A:
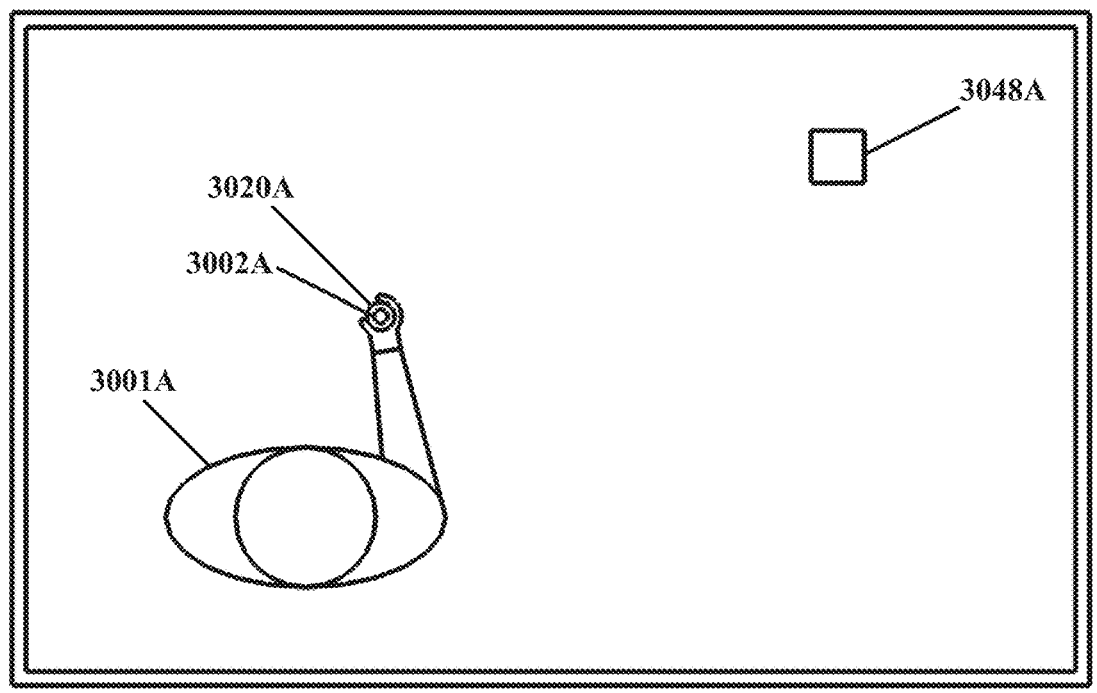
FIG. 30A through FIG. 30D depict an example apparatus as may be suited for determining the use of medication through radio frequency passive modulation utilizing a dedicated RF signal in operation, in top-down view.

In FIG. 30A, a remote 3020A is shown with a container 3002A engaged therewith, held in the hand of a user 3001A, within some enclosed space (not numbered). As may be seen, the remote 3020A is engaged with the container 3002A in such fashion that the remote 3020A may be a label wrapped around the container 3002A, a sleeve with the container 3002A disposed therein, etc. (though these are examples only). In addition, a base 3048A is shown at some distance from the user 3001A and the remote 3020A. The arrangement shown in FIG. 30A may be understood in some sense as an inactive condition, in that neither the base 3048A nor the remote 3020A is exhibiting any action as illustrated. Such an arrangement may exist when the base 3048A is not active, not plugged in, etc.

Figure 30B:
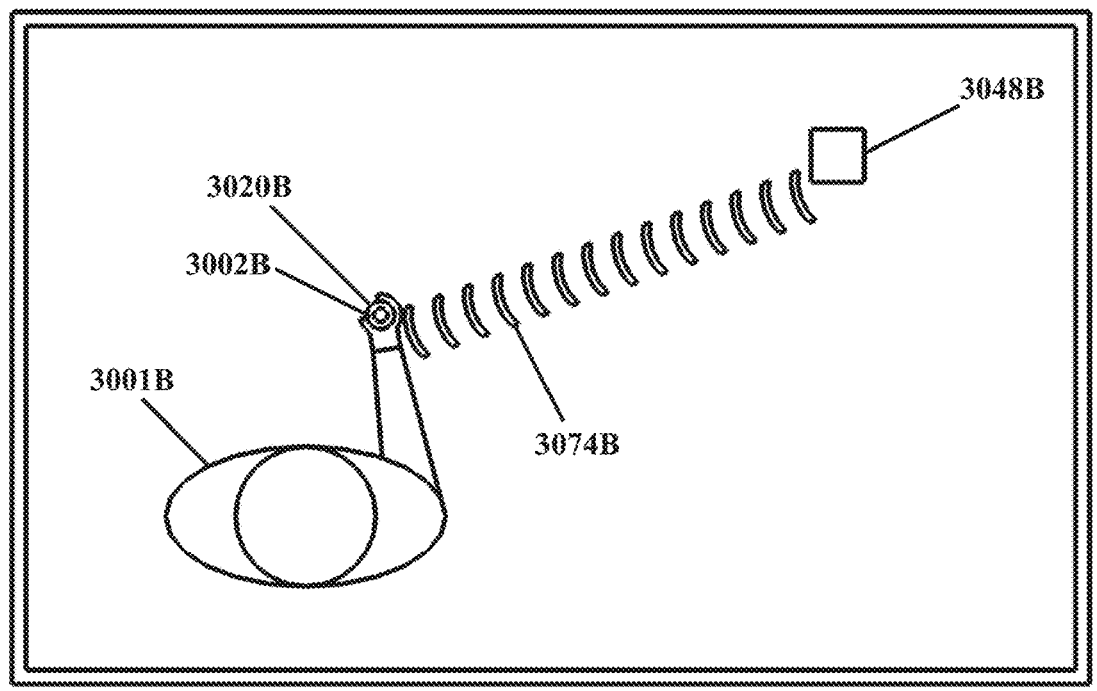

Turning to FIG. 30B, as has been described previously herein the base 3048B may provide an RF signal 3074B, shown in FIG. 30B as convex segments extending from the base 3048B toward the remote 3020B. (The RF signal 3074B is illustrated as linear in FIG. 30B for purposes of clarity. In practice the RF signal 3074B, and likewise other signals illustrated herein, may be omnidirectional rather than linear, though directed signals are not excluded.) As shown, the remote 3020B is exhibiting no response. The arrangement shown in FIG. 30B may be understood as a monitoring condition, wherein certain systems (e.g., the base 3048B) may be active but no communication or registering of events may be taking place.

Figure 30C:
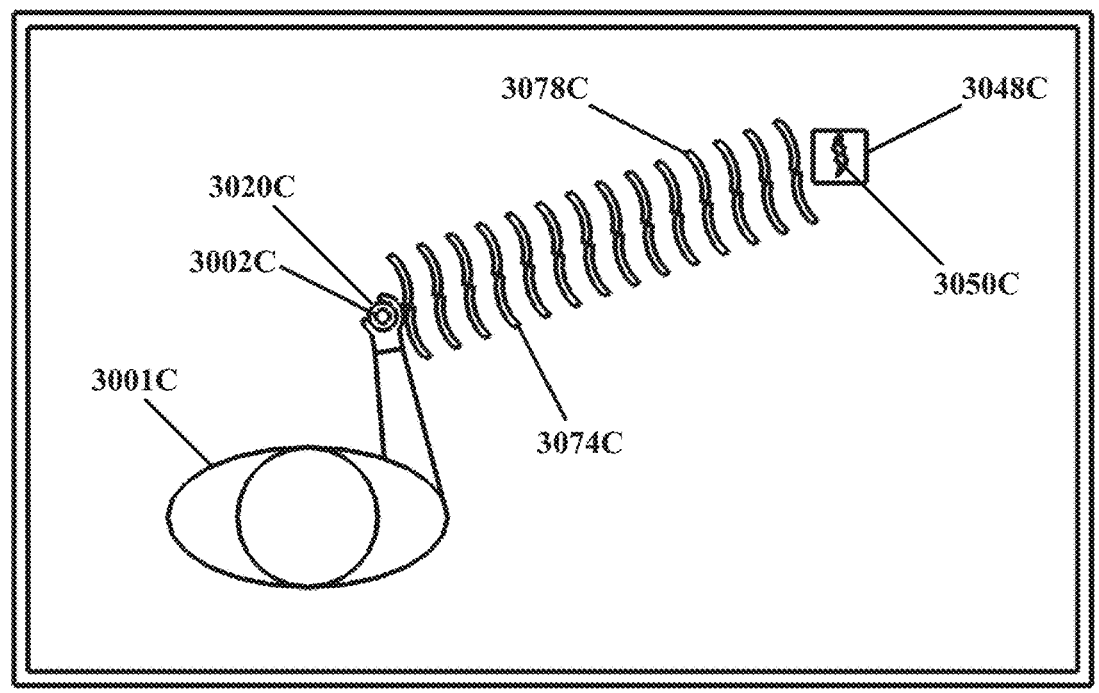

Moving on to FIG. 30C, as described previously herein a remote 3020C may be activated so as to initiate an energizer, e.g. by squeezing the container 3002C to expel an eyedrop and thus deforming a piezoelectric element serving as an energizer. (In practice the container 3002C may be elevated when dispensing eyedrops; however, the arrangement in FIG. 30C remains similar to that in FIG. 30A and FIG. 30C for comparison purposes.) In such instance, as shown in FIG. 30C, the base 3048C provides an RF signal 3074C. The remote 3020C receives the RF signal 3074C, and emits an IF signal 3078C in response (e.g., through radio frequency passive modulation of the RF signal 3074C with an LO signal, not shown), the IF signal 3078C being illustrated in FIG. 30C as convex segments extending from the remote 3020C toward the base 3048C. The base 3048C receives the IF signal 3078C, and registers 3050C a medication-associated event (e.g., squeezing the bottle, dispensing the medication, etc.). The arrangement shown in FIG. 30C may be considered as an active condition, wherein an event is taking place and/or being signaled by transmission of the IF signal 3048C.

It is noted that in practice registration 3050C may have no physical substance, e.g., "registration" being an event rather than an object. Nevertheless, registration 3050C is shown in FIG. 30C for explanatory purposes, in the form of a lightning bolt symbol on the base 3148C, so as to provide a graphical indication that the base 3048C registers 3050C an event in response to the incoming IF signal 3078C.

Figure 30D:
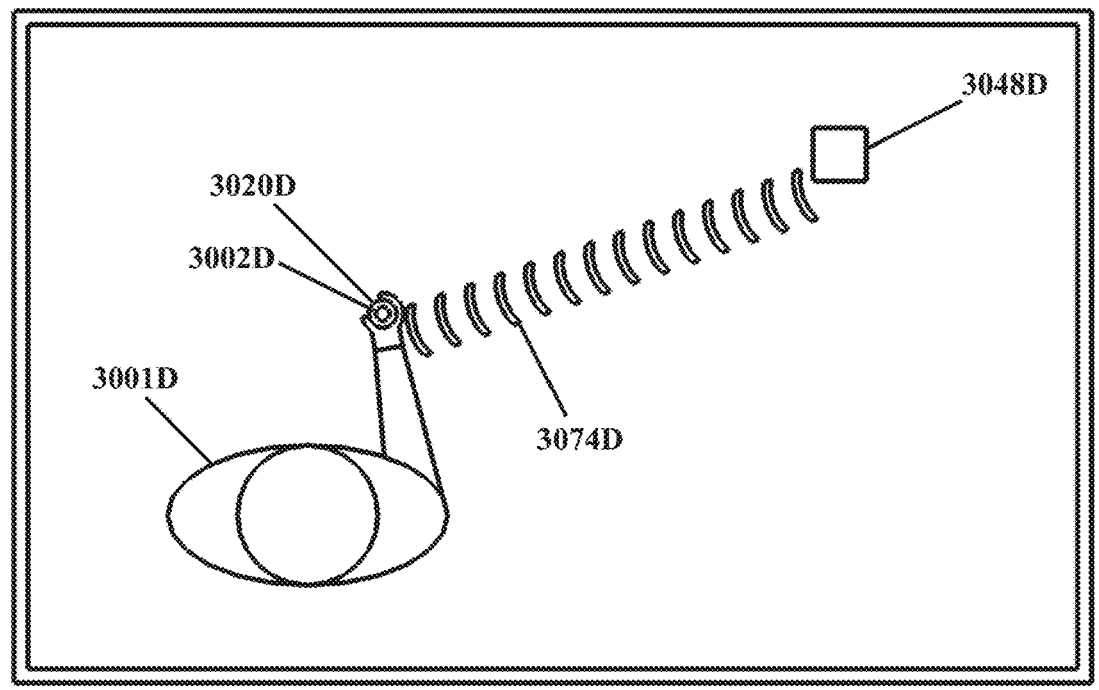

Now with reference to FIG. 30D, an arrangement similar to that in FIG. 30B is shown. The base 3048D continues to send the RF signal 3074D, but the remote 3020D engaged with the container 3002D does not continue to provide an IF signal, and the base 3048D does not continue registering events. The arrangement shown in FIG. 30D thus may be understood as a return to a monitoring condition.

Sequences as shown in FIG. 30A through FIG. 30D are illustrative, and should not be understood as limiting. Arrangements may be more complex, other conditions may be present, sequences may repeat (e.g., an IF signal as shown being sent in FIG. 30C may be sent once for each eyedrop expelled, thus several "cycles" of IF signal may be sent with the system in a monitoring condition as in FIG. 30B/FIG. 30D therebetween), and so forth. Numerous variations may be possible.

Figure 31A:
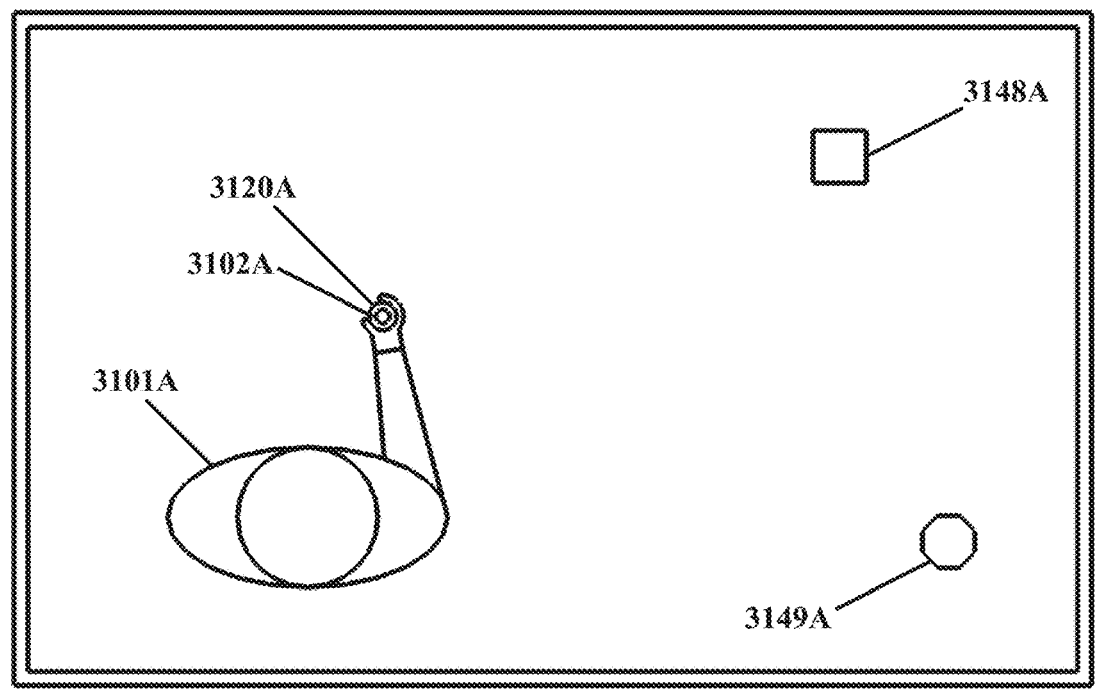
FIG. 31A through FIG. 31D depict an example apparatus as may be suited for determining the use of medication through radio frequency passive modulation utilizing an ambient RF signal in operation, in top-down view.

Turning to FIG. 31A through FIG. 31D, one such variation (though not necessarily the only one possible) is shown. Specifically, with reference to FIG. 31A, a system of base 3148A and remote 3120A are shown in an inactive condition. The remote 3120A is engaged with a container 3102A held by a user 3101A, but no signals are shown to be sent. In addition, FIG. 31A shows an ambient RF source 3149A, also shown as inactive (e.g., producing no signal). As has been noted, ambient RF signals may be utilized instead of and/or in addition to dedicated RF signals such as may be produced by a base 3148A. However, although a well-defined ambient RF source 3149A is shown in FIG. 31A for explanatory purposes, it may not be necessary for a user 3101A or other person to identify an ambient RF source 3149A, and an ambient RF source 3149A need not be well-defined. More colloquially, the user may not need to know what is producing ambient RF, where the ambient RF is coming from, etc., and ambient RF need not come from a single source; ambient RF may simply be "background noise". So long as the RF signal provided is sufficient for the functions described herein, ambient RF signals are not limited.

Figure 31B:
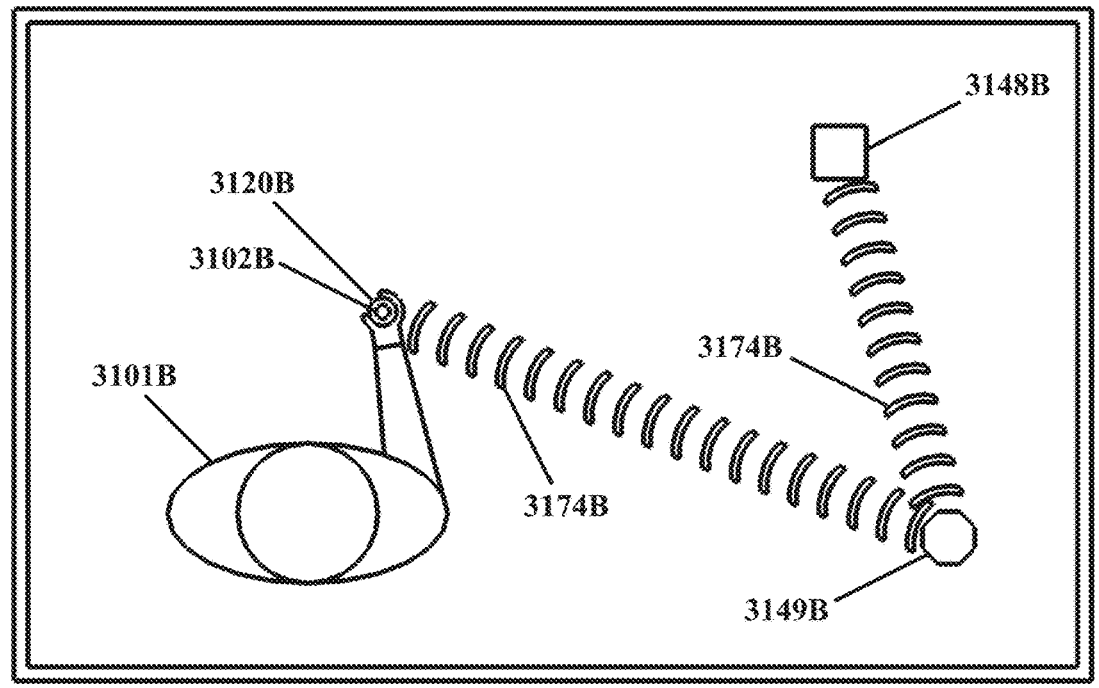

Moving on to FIG. 31B, an arrangement similar to that in FIG. 31A is shown, but in a monitoring condition. An ambient RF source 3149B provides an RF signal 3174B, shown as convex segments extending from the ambient RF source 3149B toward the remote 3120B and from the ambient RF source 3149B toward the base 3148B. (As noted, in practice an RF signal 3148B may be omnidirectional. Thus while the RF signal 3148B is illustrated as two transmissions in FIG. 31B for clarity, the RF signal may not be so divided; the base 3148B and remote 3120B may be receiving "the same signal".) The remote 3120B, engaged with a container 3102B and held in the hand of a user 3101B, is not shown to send an IF signal; the base 3148B is not shown to register an event. The remote 3120B may or may not receive the RF signal 3174B even though the RF signal 3174B is shown to be present; so long as the remote 3120B is not energized, an IF signal may not be sent regardless of whether the RF signal 3174B is received in the remote 3120B or not. Similarly, the base 3148B may or may not receive the RF signal 3174B; so long as the no IF signal is available an event may not be registered regardless of whether the RF signal 3174B is received in the base 3148B or not.

Figure 31C:
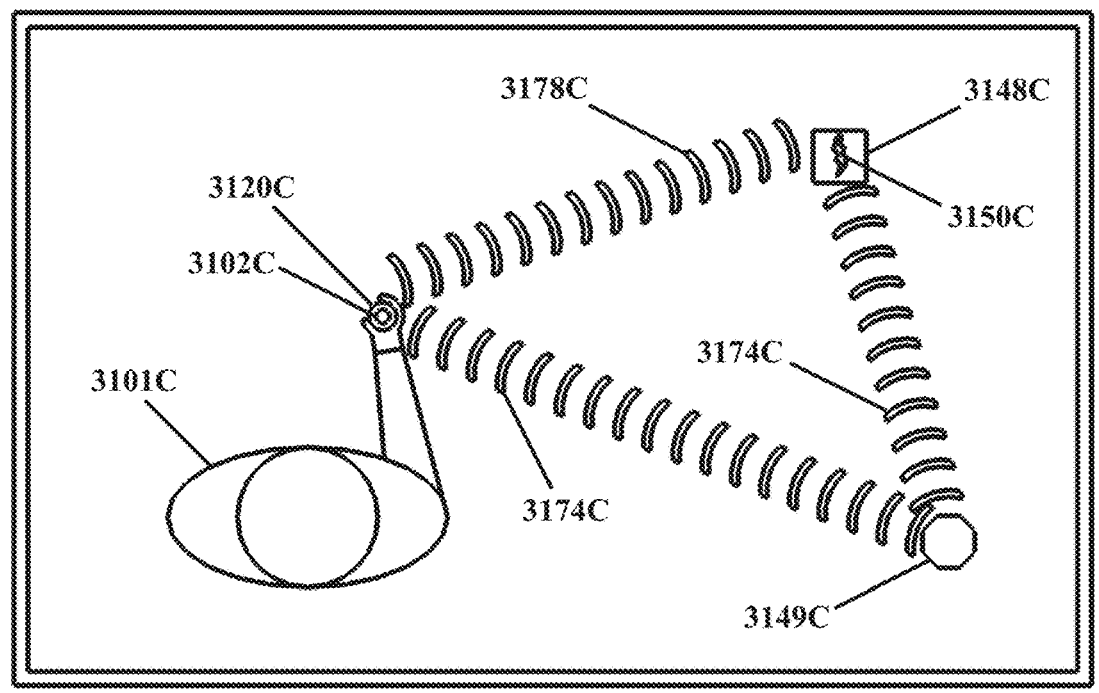

Continuing to FIG. 31C, as described previously herein an ambient RF signal 3178C may be present so as to be received by a remote 3120C (shown engaged with a container 3102C, held by a user 3101C) and a base 3148C. As shown in FIG. 31C, the remote 3120C receives the RF signal 3174C, and emits an IF signal 3178C in response. The base 3148C also receives the RF signal 3174C and receives the IF signal 3178C, and in view of both the RF signal 3174C and receives the IF signal 3178C registers 3150C a medication-associated event. Thus the arrangement shown in FIG. 31C may be considered as exhibiting an active condition for an apparatus comprising a remote 3120C and a base 3148C (and/or for one or both of the remote 3120C and base 3148C individually).

Figure 31D:
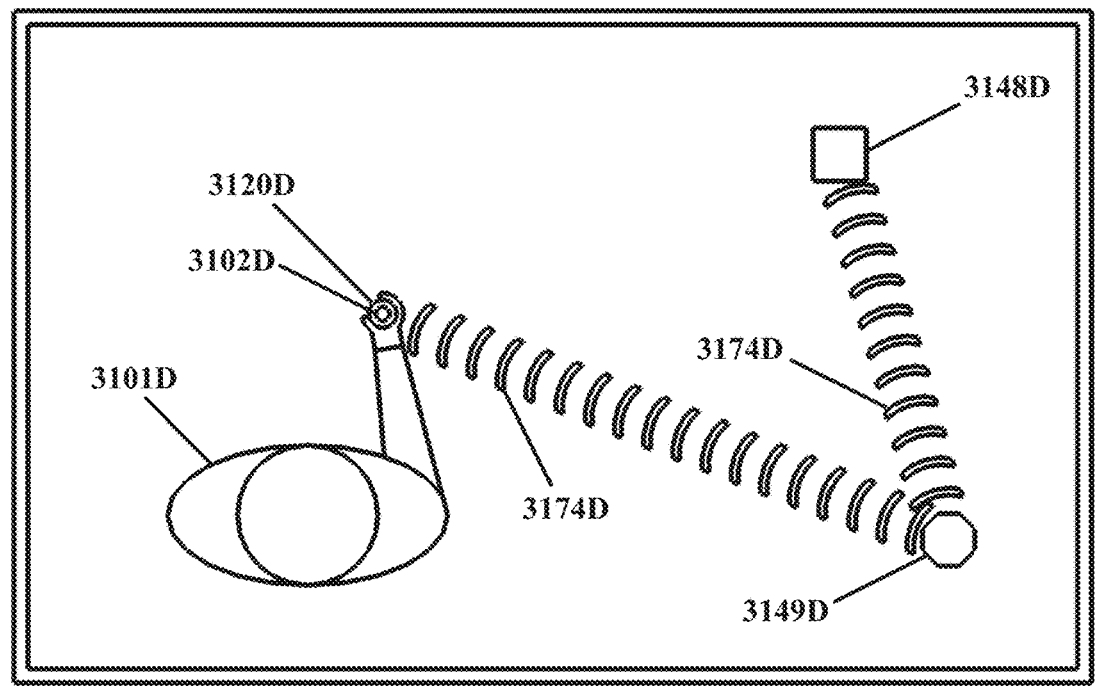

Now with reference to FIG. 31D, an arrangement similar to that in FIG. 31B is shown. The ambient RF source 3149D continues to provide the RF signal 3174D, but the remote 3120D engaged with the container 3102D as held by the user 3101D does not continue to provide an IF signal, and the base 3148D does not continue registering events. The arrangement shown in FIG. 31D thus may be understood as a return to a monitoring condition.

Figure 32:
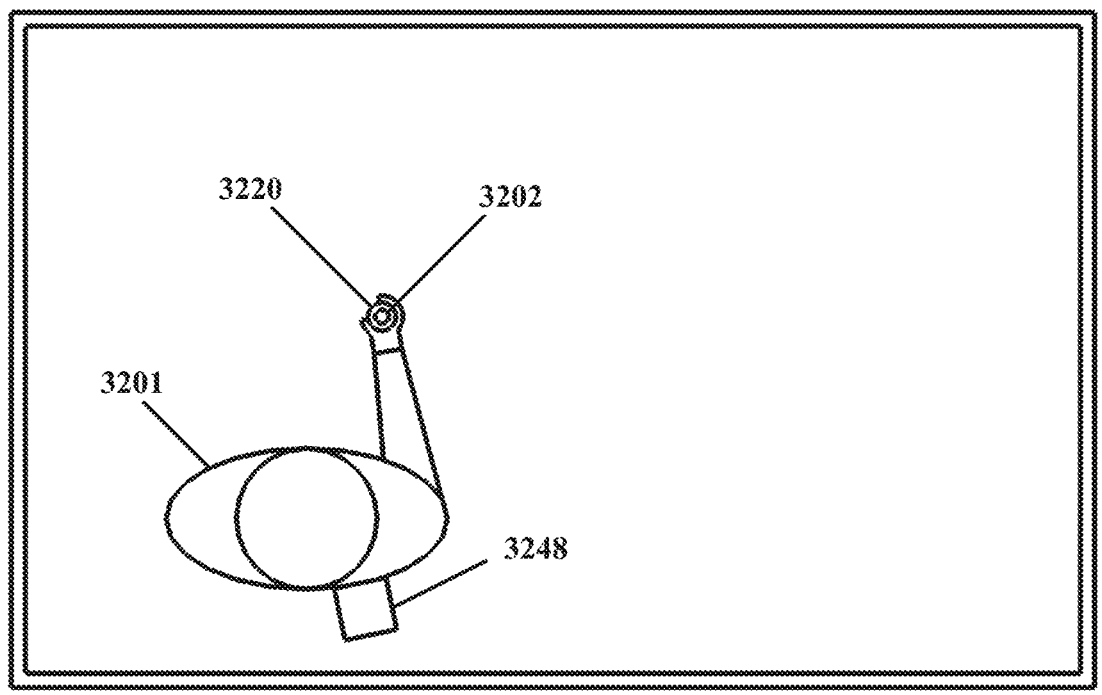
FIG. 32 depicts an example apparatus as may be suited for determining the use of medication through radio frequency passive modulation with a portable base, in top-down view.

Moving on to FIG. 32, in the examples of FIG. 30A through FIG. 30D and FIG. 31A through FIG. 31D the bases shown therein were illustrated as being at some distance from the user. For example, such bases may be "standalone" systems, plugged into a wall socket, stored in a medicine cabinet, sitting on a shelf, etc. However, bases also may be portable, and/or may be carried by a user.

As shown in FIG. 32, a remote 3220 is engaged with a container 3202, held by a user 3201. A base 3248 is shown to be present, but unlike certain previous examples the base 3248 is disposed on/next to the user 3201. For example, the base 3248 may be in a back pocket of clothing worn by the user 3201. As a more concrete example, provided suitable functionality is facilitated (e.g., with executable instructions, appropriate sensors, etc.) certain portable electronic devices including but not limited to a smart phone may be suitable for use as a base in at least some embodiments. The particular structure, location, degree of portability, etc., of the base 3248 is not limited, and may vary considerably.

The arrangement shown in FIG. 32 does not include signals, registration, etc. Functionality with regard to either dedicated RF signals or ambient RF signals may be similar to arrangements shown in FIG. 30A through FIG. 30D and FIG. 31A through FIG. 31D. Relocating the base, and/or changing the base from freestanding to portable, etc., may not affect the functionality of a system as shown, and is not limiting.

With regard to FIG. 30A through FIG. 32, and also to certain other examples presented herein, it is noted that what precisely may be considered to constitute an "apparatus" may vary. In certain instances, it may be suitable to consider a combination of remote and base to be an apparatus for determining use of medication through radio frequency passive modulation. In other instances, the remote and/or base individually may be considered as a distinct apparatus. Similarly, a container with which a remote is engaged may or may not be considered part of an apparatus. For example, a container with elements of a remote integrally incorporated therein may reasonably be considered as being part of an apparatus for determining use of medication through radio frequency passive modulation, while a container to which a remote is retrofitted (e.g., as a label applied to that container) may be considered separate from and/or not part of such an apparatus. While shown in certain examples, users and/or sources of ambient RF may not themselves be considered to be part of a given apparatus.

Figure 33:
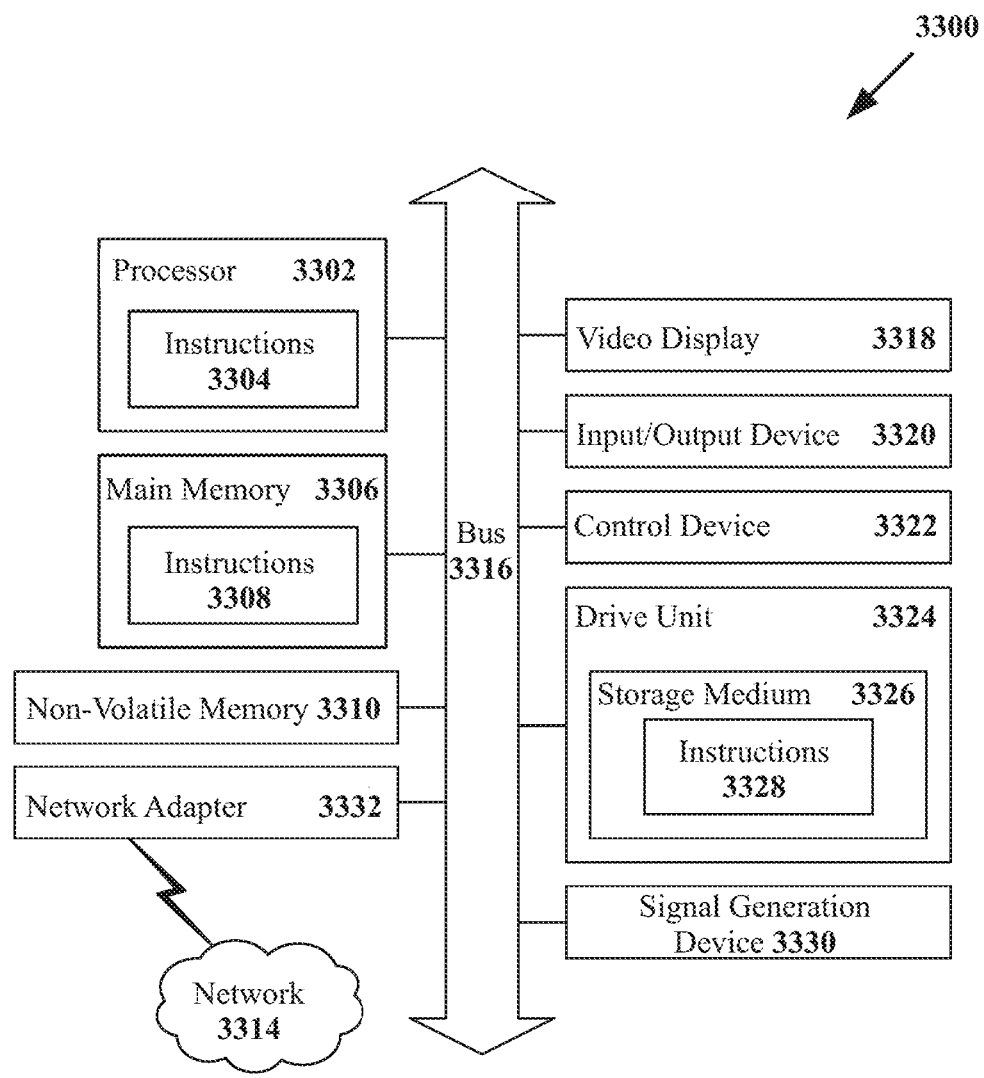
FIG. 33 is a block diagram illustrating an example of a processing system in which at least some operations described herein can be implemented.

Turning to FIG. 33, therein is shown a block diagram illustrating an example of a processing system 3300 in which at least some operations described herein can be implemented. The processing system may include one or more central processing units ("processors") 3302, main memory 3306, non-volatile memory 3310, network adapter 3312 (e.g., network interfaces), video display 3318, input/output devices 3320, control device 3322 (e.g., keyboard and pointing devices), drive unit 3324 including a storage medium 3326, and signal generation device 3330 that are communicatively connected to a bus 3316. The bus 3316 is illustrated as an abstraction that represents any one or more separate physical buses, point to point connections, or both connected by appropriate bridges, adapters, or controllers. The bus 3316, therefore, can include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the processing system 3300 operates as a standalone device, although the processing system 3300 may be connected (e.g., wired or wirelessly) to other machines. In a networked deployment, the processing system 3300 may operate in the capacity of a server or a client machine in a client-server network environment, or as a peer machine in a peer-to-peer (or distributed) network environment.

The processing system 3300 may be a server, a personal computer (PC), a tablet computer, a laptop computer, a personal digital assistant (PDA), a mobile phone, a processor, a telephone, a web appliance, a network router, switch or bridge, a console, a hand-held console, a (hand-held) gaming device, a music player, any portable, mobile, hand-held device, or any machine capable of executing a set of instructions (sequential or otherwise) that specify actions to be taken by the processing system.

While the main memory 3306, non-volatile memory 3310, and storage medium 3326 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 3328. The term "machine-readable medium" and "storage medium" shall also be taken to include any medium that is capable of storing, encoding, or carrying a set of instructions for execution by the processing system and that cause the processing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 3304, 3308, 3328) set at various times in various memory and storage devices in a computer, and that, when read and executed by one or more processing units or processors 3302, cause the processing system 3300 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 3310, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 3312 enables the processing system 3300 to mediate data in a network 3314 with an entity that is external to the computing device 3300, through any known and/or convenient communications protocol supported by the processing system 3300 and the external entity. The network adapter 3312 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 3312 can include a firewall that can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

As indicated above, the computer-implemented systems introduced here can be implemented by hardware (e.g., programmable circuitry such as microprocessors), software, firmware, or a combination of such forms. For example, some computer-implemented systems may be embodied entirely in special-purpose hardwired (i.e., non-programmable) circuitry. Special-purpose circuitry can be in the form of, for example, application-specific integrated circuits (ASICs), programmable logic devices (PLDs), field-programmable gate arrays (FPGAs), etc.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

What is claimed is:

1. An apparatus comprising:
    a remote adapted to be engaged with a container, said remote comprising:
        a radio frequency passive modulator adapted to apply a frequency modification to an RF signal by frequency mixing an LO signal therewith so as to produce an IF signal characteristic of radio frequency passive modulator, said RF signal, and said LO signal;
        a first RF receiver adapted to wirelessly receive said RF signal and provide said RF signal to an RF port of said radio frequency passive modulator;
        an LO generator adapted to generate an LO signal and provide said LO signal to an LO port of said radio frequency passive modulator;
        an IF emitter adapted to receive said IF signal from an IF port of said radio frequency passive modulator and wirelessly emit said IF signal;
        an initiator adapted to be initiated by an action associated with dispensing a contents from said container;
        an energizer engaged with said initiator and in communication with said radio frequency passive modulator, said first RF receiver, said LO generator, and said IF emitter such that when said initiator is initiated said energizer energizes said radio frequency passive modulator, said first RF receiver, said LO generator, and said IF emitter;
    a base distal from said container, comprising:
        a processor adapted to execute executable instructions;
        an RF assembly, comprising at least one of:
            an RF generator adapted to generate said RF signal therein and an RF emitter adapted to receive said RF signal from said RF generator and wirelessly emit said RF signal; and
            a second RF receiver adapted to wirelessly receive said RF signal;
        an IF receiver adapted to wirelessly receive said IF signal and provide said IF signal to said processor;
        a registerer comprising at least one of:
            a data store in communication with said processor;
            a communicator in communication with said processor; and
            an outputter in communication with said processor;
        a clock in communication with said processor; and
        a base electrical supply adapted to energize said processor, said RF assembly, said IF receiver, said registerer, and said clock;
    wherein:
    said processor is adapted to compare said IF signal to an IF signal standard;
    said processor is adapted to register via said registerer a contextual event associated with dispensing said contents if said IF signal satisfies said IF standard;
    said registering comprising at least one of:
        storing a presence of said contextual event and a time of said contextual event in said data store;
        communicating said presence of said contextual event and said time of said contextual event to an external entity via said communicator; and
        outputting said presence of said contextual event and said time of said contextual event via said outputter.

2. The apparatus of claim 1, wherein:
said IF signal standard is characteristic of said RF signal as generated and emitted in said base, said LO signal as generated in said remote, and said frequency mixing in said radio frequency passive modulator.

3. The apparatus of claim 1, wherein:
said IF signal standard is characteristic of said RF signal as generated externally from said base and said remote, said LO signal as generated in said remote, and said frequency mixing in said radio frequency passive modulator.

4. The apparatus of claim 3, wherein:
said RF signal comprises an ambient signal.

5. The apparatus of claim 4, wherein:
said RF signal comprises an electromagnetic wave from at least one of: mains electricity, transmission electricity, data line emissions, fluorescent lighting, broadcast radio, broadcast television, cellular communication, Wi-Fi®, BLUETOOTH®, and astronomical radio waves.

6. The apparatus of claim 1, wherein:
said IF signal standard comprises said RF signal, said LO signal, and at least one frequency mixing parameter for said radio frequency passive modulator.

7. The apparatus of claim 1, wherein:
said IF signal standard is at least one of:
    instantiated on said processor;
    stored in said data store; and
    obtained via said communicator.

8. The apparatus of claim 1, wherein:
said IF signal standard addresses a plurality of IF signals characteristic with a respective plurality of RF signals.

9. The apparatus of claim 1, wherein:
said base data store comprises at least one of a hard drive, a solid state drive, an optical drive, a removable memory card, a removable optical disc, and a removable magnetic disc.

10. The apparatus of claim 1, wherein:
said base communicator comprises at least one of a hard-wired communicator, a Wi-Fi® communicator, a BLUETOOTH® communicator, a cellular network communicator, an infrared communicator, and a radio communicator.

11. The apparatus of claim 1, wherein:
said base outputter comprises at least one of a graphical display, an audio speaker, visual telltales, a liquid crystal display, a light emitting diode display, a cathode ray tube display, and an electronic paper display.

12. The apparatus of claim 1, wherein:
said base comprises a user interface.

13. The apparatus of claim 12, wherein:
said user interface comprises at least one of a keypad, a touch screen, a voice input, and at least one discrete mechanical control.

14. The apparatus of claim 1, wherein:
said base comprises a portable electronic device.

15. The apparatus of claim 1, wherein:
said base comprises at least one of a smart phone, a tablet computer, a laptop computer, a desktop computer, a game console, a smart watch, a Personal Data Assistant, and a head mounted display.

16. The apparatus of claim 1, wherein:
said container is a medication container, and said contents comprises a medication.

17. The apparatus of claim 1, wherein:
said container comprises at least one of a squeeze bottle, a squeeze tube, a hypodermic syringe, an auto-injector, a syrette, a twist-cap bottle, a flip-top bottle, an inhaler, and a single-use cartridge.

18. The apparatus of claim 1, wherein said initiator comprises at least one of:
a flexible region defined adapted to be deformed by a user squeezing said container so as to dispense said contents therefrom;
a rotary cap for said container adapted to be rotated by said user so as to open said container;
a movable cap for said container adapted to be translated by said user so as to open said container;
a frangible element adapted to be broken by said user so as to open said container;
an optical window adapted to pass light therethrough; and
an RF window adapted to pass radio frequency waves therethrough.

19. The apparatus of claim 1, wherein:
said energizer comprises at least one of a piezoelectric element, a plunger generator, a rotary generator, a photovoltaic element, a radio frequency power harvester, a triboelectric element, and a fractoelectric element.

20. The apparatus of claim 1, wherein:
said remote comprises at least one control gate, said control gate comprising a negative state and a positive state;
wherein:
if said control gate is in said negative state said control gate inhibits said energizer from energizing at least one of said radio frequency passive modulator, said first RF receiver, said LO generator, and said IF emitter; and
if said control gate is in said positive state said control gate does not inhibit said energizer.

21. The apparatus of claim 20, wherein:
said control gate comprises a cap sensor for a cap for said container, such that if said cap is engaged with said container said control gate is in a negative state, and if said cap is not engaged with said container said control gate is in a positive state.

22. The apparatus of claim 21, wherein:
said control gate comprises a short circuit within said cap, such that if said cap is engaged with said container said short circuit bypasses said energizer from energizing said at least one of said radio frequency passive modulator, said first RF receiver, said LO generator, and said IF emitter, and if said cap is not engaged with said container said short circuit does not bypass said energizer.

23. The apparatus of claim 1, wherein:
said remote is integral to said container.

24. The apparatus of claim 23, wherein:
said initiator comprises a flexible region defined in a wall of said container;
said energizer comprises a piezoelectric element engaged with said flexible region; and
said radio frequency passive modulator, said first RF receiver, said LO generator, and said IF emitter are disposed in a wall of said container.

25. The apparatus of claim 1, wherein:
said remote is adapted to be fixedly engaged with said container.

26. The apparatus of claim 25, wherein:
said remote comprises a membrane fixedly adhered to said container;
said initiator comprises a flexible region defined in said membrane;
said energizer comprises a piezoelectric element engaged with said flexible region; and
said radio frequency passive modulator, said first RF receiver, said LO generator, and said IF emitter are disposed in said membrane.

27. The apparatus of claim 1, wherein:
said remote is adapted to be removably engaged with said container.

28. The apparatus of claim 27, wherein:
said remote comprises a sleeve with said container removably disposed therein;
said initiator comprises a flexible region defined in said sleeve;
said energizer comprises a piezoelectric element engaged with said flexible region; and
said radio frequency passive modulator, said first RF receiver, said LO generator, and said IF emitter are disposed in said sleeve.

29. A method, comprising:
in a base distal from a container, establishing an RF signal, comprising at least one of:
generating said RF signal and wirelessly emitting said RF signal from said base; and
wirelessly receiving said RF signal in said base;
in a remote engaged with said container, initiating an initiator responsive to an action associated with dispensing a contents from a container, such that initiating said initiator causes an energizer of said remote to energize said remote;
when energized:
wirelessly receiving said RF signal in said remote;
generating an LO signal in said remote;
modulating said RF signal and said LO signal in said remote to produce an IF signal;
wirelessly emitting said IF signal from remote;
in said base:
receiving said IF signal;
comparing said IF signal to an IF signal standard;
if said IF signal satisfies said IF signal standard, registering an event associated with said contents of said container, registering comprising at least one of storing said event and an event time thereof in said base, communicating said event and said event time from said base, and outputting said event and said event time from said base.

30. An apparatus, comprising:
RF modifying means for applying a frequency modification to an RF signal by frequency mixing an LO signal therewith so as to produce an IF signal;
first RF receiving means for wirelessly receiving said RF signal;

LO generating means for generating said LO signal;
IF emitting means for wirelessly emitting said IF signal;
energizing means for energizing said RF modifying means, said RF receiving means, said LO generating means, and said IF emitting means;
initiating means for initiating said energizing means responsive to an action associated with dispensing a contents from a container;
engaging means for engaging said RF modifying means, said RF receiving means, said LO generating means, said IF emitting means, said energizing means, and said initiating means with said container;
RF provision means comprising at least one of:
  RF generating means for generating said RF signal, and RF emitting means for wirelessly emitting said RF signal; and
  second RF receiving means for wirelessly receiving said RF signal;
IF receiving means for wirelessly receiving said IF signal;
comparing means for comparing said IF signal to an IF standard;
certifying means for certifying said IF signal as corresponding with an event associated with said contents of said container if said IF signal satisfies said IF standard;
timing means for determining an event time of said event;
registering means for registering said event, comprising at least one of:
  storing means for storing said event and said event time;
  communicating means for communicating said event and said event time; and
  outputting means for outputting said event and said event time;
wherein said RF provision means, said IF receiving means, said comparing means, said certifying means, said timing means, and said registering means are distal from said container.

* * * * *